United States Patent
Marziali et al.

(10) Patent No.: US 11,879,151 B2
(45) Date of Patent: **\*Jan. 23, 2024**

(54) LINKED LIGATION

(71) Applicant: NCAN Genomics, Inc., Vancouver (CA)

(72) Inventors: Andrea Marziali, North Vancouver (CA); Joel Pel, Vancouver (CA)

(73) Assignee: NCAN GENOMICS, INC., Vancouver (CA)

( * ) Notice: Subject to any disclaimer, the term of this patent is extended or adjusted under 35 U.S.C. 154(b) by 66 days.

This patent is subject to a terminal disclaimer.

(21) Appl. No.: 17/688,220

(22) Filed: Mar. 7, 2022

(65) Prior Publication Data
US 2022/0186298 A1   Jun. 16, 2022

Related U.S. Application Data

(63) Continuation of application No. 16/467,870, filed as application No. PCT/IB2017/057732 on Dec. 7, 2017, now Pat. No. 11,268,137.

(Continued)

(51) Int. Cl.
*C12Q 1/68* (2018.01)
*C12Q 1/6827* (2018.01)
(Continued)

(52) U.S. Cl.
CPC ............ *C12Q 1/6827* (2013.01); *C12Q 1/68* (2013.01); *C12Q 1/686* (2013.01); *C12Q 1/6806* (2013.01);
(Continued)

(58) Field of Classification Search
None
See application file for complete search history.

(56) References Cited

U.S. PATENT DOCUMENTS 4,683,195 A   7/1987   Mullis et al.
4,683,202 A   7/1987   Mullis
(Continued)

FOREIGN PATENT DOCUMENTS

CA   3048420 A1   6/2018
EP   2405017 A1   1/2012
(Continued)

OTHER PUBLICATIONS

Alazard, 2002, Sequencing of production-scale synthetic oligonucleotides by enriching for coupling failures using matrix-assisted laser desorption/ionization time of-flight mass spectrometry, Anal Biochem 301:57-64.
(Continued)

*Primary Examiner* — Aaron A Priest
(74) *Attorney, Agent, or Firm* — Withers Bergman LLP

(57) ABSTRACT

The invention generally relates to capturing, amplifying, and sequencing nucleic acids. In certain embodiments, copies of the sense and antisense strands of a duplex template nucleic acid are captured using linked capture probes and multiple binding and extension steps to improve specificity over traditional single binding target capture techniques. Methods of seeding sequencing clusters with sense and antisense strands of a target nucleic acid are also disclosed including identifying the strands using sense-specific barcodes and confirming base calls using two sense-specific sequencing reads. Linked adapters may be used to increase adapter ligation selectively or efficiency and yield.

11 Claims, 54 Drawing Sheets

Related U.S. Application Data

(60) Provisional application No. 62/569,824, filed on Oct. 9, 2017, provisional application No. 62/432,277, filed on Dec. 9, 2016.

(51) Int. Cl.
    *C12Q 1/6806* (2018.01)
    *C12Q 1/6855* (2018.01)
    *C12Q 1/686* (2018.01)
    *C12Q 1/6869* (2018.01)

(52) U.S. Cl.
    CPC ......... *C12Q 1/6855* (2013.01); *C12Q 1/6869* (2013.01); *C12Q 2521/501* (2013.01); *C12Q 2525/161* (2013.01); *C12Q 2525/191* (2013.01); *C12Q 2531/113* (2013.01); *C12Q 2535/122* (2013.01)

(56) References Cited

U.S. PATENT DOCUMENTS

| | | |
|---|---|---|
| 5,122,450 A | 6/1992 | Feizi et al. |
| 5,604,097 A | 2/1997 | Brenner |
| 5,636,400 A | 6/1997 | Young |
| 5,695,934 A | 12/1997 | Brenner |
| 5,846,719 A | 12/1998 | Brenner et al. |
| 5,863,722 A | 1/1999 | Brenner |
| 6,138,077 A | 10/2000 | Brenner |
| 6,150,516 A | 11/2000 | Brenner et al. |
| 6,172,214 B1 | 1/2001 | Brenner |
| 6,172,218 B1 | 1/2001 | Brenner |
| 6,210,891 B1 | 4/2001 | Nyren et al. |
| 6,235,475 B1 | 5/2001 | Brenner et al. |
| 6,235,501 B1 | 5/2001 | Gautsch et al. |
| 6,258,568 B1 | 7/2001 | Nyren |
| 6,274,320 B1 | 8/2001 | Rothberg et al. |
| 6,306,597 B1 | 10/2001 | Macevicz |
| 6,352,828 B1 | 3/2002 | Brenner |
| 6,719,449 B1 | 4/2004 | Laugharn, Jr. et al. |
| 6,818,395 B1 | 11/2004 | Quake et al. |
| 6,828,100 B1 | 12/2004 | Ronaghi |
| 6,833,246 B2 | 12/2004 | Balasubramanian |
| 6,911,345 B2 | 6/2005 | Quake et al. |
| 6,948,843 B2 | 9/2005 | Laugharn, Jr. et al. |
| 7,041,481 B2 | 5/2006 | Anderson et al. |
| 7,057,026 B2 | 6/2006 | Barnes et al. |
| 7,169,560 B2 | 1/2007 | Lapidus et al. |
| 7,232,656 B2 | 6/2007 | Balasubramanian et al. |
| RE39,793 E | 8/2007 | Brenner |
| 7,282,337 B1 | 10/2007 | Harris |
| 7,393,665 B2 | 7/2008 | Brenner |
| 7,537,897 B2 | 5/2009 | Brenner et al. |
| 7,544,473 B2 | 6/2009 | Brenner |
| 7,598,035 B2 | 10/2009 | Macevicz |
| 7,708,949 B2 | 5/2010 | Stone et al. |
| RE41,780 E | 9/2010 | Anderson et al. |
| 7,835,871 B2 | 11/2010 | Kain et al. |
| 7,960,120 B2 | 6/2011 | Rigatti et al. |
| 8,053,192 B2 | 11/2011 | Bignell et al. |
| 9,404,146 B2 | 8/2016 | Travers et al. |
| 9,752,188 B2 | 9/2017 | Schmitt et al. |
| 9,970,054 B2 | 5/2018 | Otwinowski et al. |
| 2002/0164629 A1 | 11/2002 | Quake et al. |
| 2003/0194706 A1 | 10/2003 | Brevnov |
| 2005/0112590 A1 | 5/2005 | Boom et al. |
| 2006/0024681 A1 | 2/2006 | Smith et al. |
| 2006/0292611 A1 | 12/2006 | Berka et al. |
| 2007/0070349 A1 | 3/2007 | Harris et al. |
| 2007/0114362 A1 | 5/2007 | Feng et al. |
| 2007/0166705 A1 | 7/2007 | Milton et al. |
| 2007/0254284 A1 | 11/2007 | Zhao |
| 2008/0003142 A1 | 1/2008 | Link et al. |
| 2008/0014589 A1 | 1/2008 | Link et al. |
| 2008/0081330 A1 | 4/2008 | Kahvejian |
| 2009/0026082 A1 | 1/2009 | Rothberg et al. |
| 2009/0118128 A1 | 5/2009 | Liu et al. |
| 2009/0127589 A1 | 5/2009 | Rothberg et al. |
| 2009/0191565 A1 | 7/2009 | Lapidus et al. |
| 2009/0233814 A1 | 9/2009 | Bashkirov et al. |
| 2010/0009353 A1 | 1/2010 | Barnes et al. |
| 2010/0035252 A1 | 2/2010 | Rothberg et al. |
| 2010/0081141 A1 | 4/2010 | Chen et al. |
| 2010/0111768 A1 | 5/2010 | Banerjee et al. |
| 2010/0137143 A1 | 6/2010 | Rothberg et al. |
| 2010/0137163 A1 | 6/2010 | Link et al. |
| 2010/0172803 A1 | 7/2010 | Stone et al. |
| 2010/0188073 A1 | 7/2010 | Rothberg et al. |
| 2010/0196890 A1 | 8/2010 | Wittwer et al. |
| 2010/0197507 A1 | 8/2010 | Rothberg et al. |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0003305 A1 | 1/2011 | Brentano et al. |
| 2011/0009278 A1 | 1/2011 | Kain et al. |
| 2011/0301042 A1 | 12/2011 | Steinmann et al. |
| 2013/0122814 A1 | 5/2013 | Shen et al. |
| 2013/0203123 A1 | 8/2013 | Nelson et al. |
| 2014/0134610 A1 | 5/2014 | Pham et al. |
| 2015/0099642 A1 | 4/2015 | Barany et al. |
| 2015/0105275 A1 | 4/2015 | Wong et al. |
| 2015/0152492 A1 | 6/2015 | Brown et al. |
| 2016/0067104 A1 | 3/2016 | Sarangapani et al. |
| 2016/0122814 A1 | 5/2016 | Despotovic et al. |
| 2016/0265042 A1 | 9/2016 | Schroeder et al. |
| 2016/0326578 A1 | 11/2016 | Bielas |
| 2018/0087104 A1 | 3/2018 | Joung et al. |
| 2018/0245132 A1 | 8/2018 | Jiang et al. |
| 2019/0024141 A1 | 1/2019 | Myllykangas et al. |
| 2019/0112654 A1 | 4/2019 | Pel et al. |
| 2019/0300939 A1 | 10/2019 | Chen et al. |

FOREIGN PATENT DOCUMENTS

| | | |
|---|---|---|
| WO | 2004/018497 A2 | 3/2004 |
| WO | 2007/123744 A2 | 11/2007 |
| WO | 2010/117817 A2 | 10/2010 |
| WO | 2012/040387 A1 | 3/2012 |
| WO | 2013/126741 A1 | 8/2013 |
| WO | 2015104302 A1 | 7/2015 |
| WO | 2016/149837 A1 | 9/2016 |
| WO | 2017/168331 A1 | 10/2017 |
| WO | 2017/168332 A1 | 10/2017 |
| WO | 2017168329 A1 | 10/2017 |
| WO | 2018104908 A2 | 6/2018 |
| WO | 2018108328 A1 | 6/2018 |
| WO | 2020039261 A1 | 2/2020 |

OTHER PUBLICATIONS

Barany, 1991, Genetic disease detection and DNA amplification using cloned thermostable ligase, PNAS 88:189-193.

Barany, 1991, The ligase chain reaction in a PCR World, PCR Methods and Applications, 1(1):5-16.

Bentzley, 1996, Oligonucleotide sequence and composition determined by matrix-assisted laser desorption/ionization, Anal Chem 68:2141-2146.

Bentzley, 1998, Base specificity of oligonucleotide digestion by calf spleen phosphodiesterase with matrix-assisted laser desorption ionization analysis, Anal Biochem 258:31-37.

Bickle, 1993, Biology of DNA Restriction, Microbiol Rev 57(2):434-50.

Boyer, 1971, DNA restriction and modification mechanisms in bacteria, Ann Rev Microbiol 25:153-76.

Braslavsky, 2003, Sequence information can be obtained from single DNA molecules, PNAS, 100:3960-3964.

Brown, 1979, Chemical synthesis and cloning of a tyrosine tRNA gene, Methods Enzymol 68:109-151.

Browne, 2002, Metal ion-catalyzed nucleic acid alkylation and fragmentation, Journal of American Chemical Society, 124(27)7950-62.

(56) References Cited

OTHER PUBLICATIONS

Chan, 2011, Natural and engineered nicking endonucleases-from cleavage mechanism to engineering of strand-specificity, Nucl Acids Res 39(1):1-18.

Dappritch, 2016, The Next Generation of Target Capture Technologies—Large DNA Fragment Enrichment and Sequencing Determines Regional Genomic Variation of High Complexity, BMC Genomics, 17:486 (14 pages).

Dieffenbach, 1995, PCR Primer, a Laboratory Manual, Cold Spring Harbor Press, Plainview, NY.

Extended European Search Report issued in European Application No. EP17773408.4, dated Mar. 30, 2019 (13 pages).

Extended European Search Report issued in European Patent Application No. 17877951.8, dated Sep. 30, 2020, 11 pages.

Faulstich, 1997, A sequencing method for RNA oligonucleotides based on mass spectrometry, Anal Chem 69:4349-4353.

Glover, 1995, Sequencing of oligonucleotides using high performance liquid chromatography and electrospray mass spectrometry, Rapid Com Mass Spec 9:897-901.

Gut, 1995, A procedure for selective DNA alkylation and detection by mass spectrometry, Nucl Acids Res 23 (8):1367-1373.

Harris, 2008, Single-Molecule DNA Sequencing of a Viral Genome, Science, 320:106-109.

International Preliminary Report on Patentability issued in International Patent Application No. PCT/IB2019/000962, dated Mar. 4, 2021, 7 pages.

International Search Report and Written Opinion issued in International Application No. PCT/IB2017/051776, dated Jun. 13, 2017 (12 Pages).

International Search Report and Written Opinion issued in International Application No. PCT/IB2017/051778, dated Jun. 23, 2017 for (12 Pages).

International Search Report and Written Opinion issued in International Application No. PCT/IB2017/051779, dated Jun. 15, 2017 (14 Pages).

International Search Report and Written Opinion issued in International Application No. PCT/IB2017/057732, dated Jul. 10, 2018 (7 Pages).

International Search Report and Written Opinion issued in International Application No. PCT/IB2019/000962, dated Jan. 21, 2020, 9 pages.

International Search Report and Written Opinion issued in International Application No. PCT/US2020/36910, dated Sep. 18, 2020 (14 pages).

Kirpekar, 1994, Matrix assisted laser desorption/ionization mass spectrometry of enzymatically synthesized RNA up to 150 kDa, Nucl Acids Res 22:3866-3870.

Kolb, 2001, Click Chemistry: Diverse Chemical Function from a Few Good Reactions, Angew Chem Int. Ed. Engl., 40 (1):2004-2021.

Kumar, 2012, PEG-Labeled Nucleotides and Nanopore Detection for Single Molecule DNA Sequencing by Synthesis, Scientific Reports 2, Article 684 (8 pages).

Lee, 1984, Antibodies to Nucleic Acids, Biochemical Education 12(3):98-101.

Lou, 2013, High-Throughput DNA Sequencing Errors are Reduced by Orders fo Magnitude Using Circle Sequencing, PNAS, 110(49):19872-19877.

Margulies, 2005, Genome sequencing in micro-fabricated high-density picotiter reactors, Nature, 437:376-380.

Maxam, 1977, A new method for Sequencing DNA, Proc. Natl. Acad. Sci., 74:560-564.

Mirkin, 1996, A DNA-based method for rationally assembling nanoparticles into macroscopic materials, Nature, 382:607-609.

Narang, 1979, Improved phosphotriester method for the synthesis of gene fragments, Methods Enzymol, 68:90-98.

Non-Final Office Action issued in U.S. Appl. No. 16/088,717, dated Jul. 30, 2020 (8 pages).

Non-Final Office Action issued in U.S. Appl. No. 16/088,720, dated Aug. 5, 2020 (9 pages).

Non-Final Office Action issued in U.S. Appl. No. 16/239,100, dated Aug. 5, 2020 (9 pages).

Nordhoff, 1993, Ion stability of nucleic acids in infrared matrix-assisted laser desorption/ ionization mass spectrometry, Nucl Acid Res 21(15):3347-57.

Oefner, 1996, Efficient random sub-cloning of DNA sheared in a recirculating point-sink flow system, Nucleic Acids Res 24(20):3879-3886.

Ordahl, 1976, Sheared DNA fragment sizing: comparison of techniques, Nucleic Acids Res 3:2985-2999.

Owens, 1998, Aspects of oligonucleotide and peptide sequencing with MALDI and electrospray mass spectrometry, Bioorg Med Chem 6:1547-1554.

Partial Supplementary European Search Report issued in European Application No. 17877951.8, dated Jun. 29, 2020 (13 pages).

Pel, 2017, Duplex Proximity Sequencing (Pro-Seq): A Method to Improve DNA Sequencing Accuracy Without the Cost of Molecular Barcoding Redundancy, BioRxiv, Retrieved from <doi:http://dx.doi.org/10.1101/16344> (33 Pages).

Pel, 2018, Abstract 425: Linked Target Capture: Rapid and high-performance NGS target enrichment for clincal sequencing applications, Molecular and Cellular Biology/Genetics (6 pages).

Pieles, 1993, Matrix-assisted laser desorption ionization time-of-flight mass spectrometry: A powerful tool for the mass and sequence analysis of natural and modified oligonucleotides, Nucleic Acids Res 21:3191-3196.

Quail, 2010, DNA: Mechanical Breakage, In Encyclopedia of Life Sciences, John Wiley & Sons Ltd, Chicester (5 pages).

Roberts, 1980, Restriction and modification enzymes and their recognition sequences, Nucleic Acids Res 8(1):r63-180.

Sargent, 1987, Isolation of differentially expressed genes, Meth Enzym 152:423-432.

Satterfield, 2014, Cooperative Primers, The Journal of Molecular Diagnostics; 16(2) (11 pages).

Schlingman, 2011, A New Method for the Covalent Attachment of DNA to a Surface for Single-Molecule Studies, Colloids and Surfaces B: Biointerfaces 83:91-95.

Schmitt, 2012, Detection of ultra-rare mutations by the next generation sequencing, Proc. Natl. Acad. Sci., 109:14508-14513.

Schmitt, 2015, Sequencing small genomic targets with high efficiency and extreme accuracy, 12(5):423-426.

Schuette, 1995, Sequence analysis of phosphorothioate oligonucleotides via matrix-assisted laser desorption ionization time-of-flight mass spectrometry, J Pharm Biomed Anal 13:1195-1203.

Smirnov, 1996, Sequencing oligonucleotides by exonuclease digestion and delayed extraction matrix-assisted laser desorption ionization time-of-flight mass spectrometry, Anal Biochem 238:19-25.

Soni, 2007, Progress toward Ultrafast DNA Sequencing Using Solid-State Nanopores, Clinical Chemistry 53:1996-2001.

Thorstenson, 1998, An Automated Hydrodynamic Process for Controlled, Unbiased DNA Shearing, Genome Res 8(8): 848-855.

Tijssen, 1993, Hybridization with Nucleic Acid Probes—Laboratory Techniques in Biochemisrt and Molecular Biology (Parts I and II), Elsevier.

Vold, 1979, Radioimmunoassays for the modified nucleosides N-[9-(ß-D-ribofuranosyl)purin-6-ylcarbamoyl]-L-threonine and 2-methylthioadenosine, Nucleic Acid Research, 7(1):193-204.

Williams, 2003, Restriction endonucleases classification, properties, and applications, Mol Biotechnol 23(3):225-43.

Wu, 1998, Sequencing regular and labeled oligonucleotides using enzymatic digestion and ionspray mass spectrometry, Anal Biochem 263:129-138.

Wu, 2001, Improved oligonucleotide sequencing by alkaline phosphatase and exonuclease digestions with mass spectrometry, Anal Biochem 290:347-352.

Yuan, 1981, Structure and mechanism of multifunctional restriction endonucleases, Ann Rev Biochem 50:285-319.

Ansorge, 2009, Next-generation DNA sequencing techniques, New Biotechnology, Elsevier BV, NL, 25(4):195-203.

Extended European Search Report issued in European Application No. 20736149.4, dated Mar. 4, 2022, 11 pages.

(56) References Cited

OTHER PUBLICATIONS

Salk, 2018, Enhancing the accuracy of next-generation sequencing for detecting rare and subclonal mutations, Nature Reviews Genetics, 19(5):269-285.
Schmitt, 2012, Detection of ultra-rare mutations by the next-generation sequencing, Proceedings of the National Academy of Sciences, 109(36):14508-14513.
Schmitt, 2013, Detection of ultra-rare mutations by the next-generation sequencing, Proceedings of the National Academy of Sciences, 109(36): Supporting Information, 3 pages.
International Search Report dated Jun. 3, 2020 for International Application No. PCT/IB2020/000027 (4 pages).
Notice of Allowance issued in U.S. Appl. No. 17/417,995, dated Apr. 18, 2022, 10 pages.
Search Report and Written Opinion dated Sep. 18, 2020, from corresponding international application No. PCT/US2020/036910, and references cited therein, 5 pages.
Written Opinion dated Jun. 3, 2020 for International Application No. PCT/IB2020/000027 (4 pages).

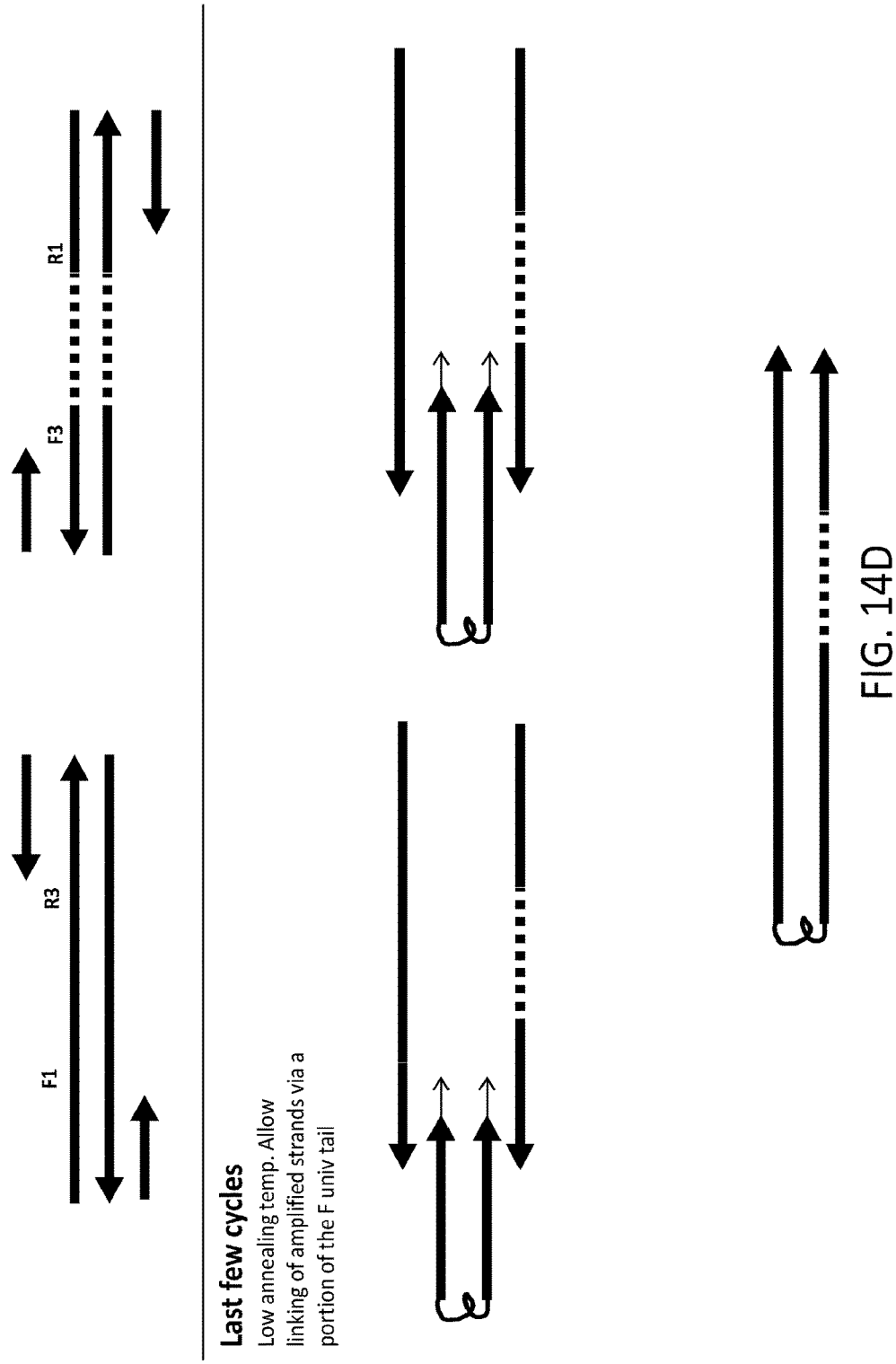

LINKED LIGATION

RELATED APPLICATIONS

This application is a continuation of U.S. Nonprovisional application Ser. No. 16/467,870, filed on Jun. 7, 2019, which is a 371 U.S. National Stage of International Application No. PCT/IB2017/057732, filed on Dec. 7, 2017, which claims the benefit of and priority to U.S. Provisional Application Nos. 62/432,277 filed on Dec. 9, 2016, and 62/569,824 filed Oct. 9, 2017, the content of each of which is incorporated by reference herein in its entirety.

FIELD OF THE INVENTION

The invention generally relates to capturing, amplifying, and sequencing nucleic acids.

BACKGROUND

High-throughput genomic sequencing platforms generate large amounts of data at affordable prices, but they are not sufficiently accurate. Even the best sequencing techniques have error rates around 1 percent. That translates to hundreds of thousands of errors in the sequence of a single human genome. Inaccurate base calling leads to sequence misalignment and the misidentification of mutations. Although base calling and alignment algorithms are available, quality is negatively impacted by amplification and sequencing errors.

Current methods of isolating target nucleic acids from a sample for sequencing are complicated and can benefit from increased accuracy. Additionally, once target nucleic acids are captured and sequenced, base calling and alignment remain riddled with errors. For example, in the currently leading sequencing platform, DNA fragments are attached to a solid support, such as a channel wall. Once a fragment is attached to the solid support, the fragment is amplified and the amplification products attach to the solid support proximate to the seeding fragment. The process repeats until a cluster of amplification products that should be identical to the seeding fragments forms. However, only one fragment seeds a cluster. If there is an error in the seeding fragment, or an error is made in the amplification of the cluster the error is repeated in the all or part of cluster. This error leads to misidentifying a base and complicating sequencing alignment.

To catch these types of errors, standard barcode sequencing methods use tens to hundreds of copies of the same template, or ten to hundreds of clusters to create a sample pool for comparison. By drastically increasing the number of copies or clusters, an error can be determined. However, this strategy is expensive and consumes sequencing bandwidth.

SUMMARY

The invention provides linked ligation adapters and methods allowing for increased ligation yields and simplified workflows in many capture and sequencing techniques. By linking sequencing or universal priming site adapters to sequence specific probes, target sequence selection and capture can be combined with adapter ligation to reduce steps and increase target selectivity. Target specific probes bring adapters linked thereto into close proximity to the target sequence at which point the linked adapters may be ligated to the target sequence. Because adapters are selectively ligated to the target sequence, subsequent amplification with universal primers complimentary to sites in the ligated adapters will only amplify the target sequence, preparing a targeted library ready for sequencing. Linked ligation techniques may be used to capture nucleic acid fusions where only one side of the breakpoint is known. By linking the adapters to sequence specific probes complimentary to the known portion of the fusion, methods may still be used to selectively ligate adapters and amplify only the target fusion nucleic acid for sequencing. In certain embodiments, one of the linked ligation adapter and probe molecules may be bound to a flow cell such that target nucleic acids may be captured and prepared for flow cell amplification or sequencing through adapter ligation at the same time, simplifying existing workflows.

Methods of the invention contemplate double stranded linked ligation. By using isothermal recombinase and single stranded binding proteins to generate strand invasion of double stranded DNA (dsDNA) with the ligation probe (similar to Recombinase Polymerase Amplification (RPA)) methods provide targeted ligation of adapters onto dsDNA.

The invention provides linked ligation adapters and methods allowing for ligation of two different adapters to a single DNA template, and increased ligation yields. By linking two different adapters prior to ligation, reaction kinetics are such that once one adapter is ligated, the second different (linked) adapter is brought into close proximity to the unligated end of the DNA for subsequent ligation. Linked adapter ligation may be used on single or double stranded DNA, in applications where it is desirable to ensure two different adapters are ligated to each template.

The invention provides methods of linked target capture for single stranded or duplex DNA molecules. Solution-based target capture methods as well as droplet-based target capture methods are provided. The solution and droplet based methods use linked target capture probes including a universal probe and a target specific probe wherein the reactions occur under conditions that require the target specific probe to bind in order to permit binding of the universal probe. Because multiple binding and extension steps are involved, specificity is improved over traditional single binding target capture. The bound universal probe is then extended using strand displacing polymerase to produce copies of the target strands which can then be amplified using PCR with universal primers. Methods of the invention replace PCR-capture-PCR workflows with a single PCR and capture step. Linked capture probes can be used in one or both senses of DNA where higher specificity and duplex information are required. Multiple linker types are possible as discussed below. Similar to solution-based target capture methods of the invention provide for droplet based methods that allow a user to perform target capture in droplets, rather than being restricted to multiplexed PCR in droplets. Capture methods may be combined with linked primers as described herein to create linked, duplex molecules from droplets. In certain embodiments, nanoparticles comprising target capture probes as well as universal primers can be used to capture targeted regions from a pool of 5'-linked molecules, converting only the targeted molecules into duplex seeds for sequencing clusters.

The invention also provides methods for increasing base calling accuracy by physically linking fragments representing both the sense and antisense strands of a duplex DNA molecule. By linking both strands into a single read, information density is increased and error rates are reduced as the duplex data permits ready differentiation between true variants and errors introduced in amplification or sequencing (e.g., errors that a polymerase might make in one sense are not likely to be repeated in both strands while a true variant would be). Sense specific barcodes may be used to confirm the presence of both sense and antisense template copies in a cluster. Dedicated sense and antisense sequencing reads may be used to differentiate between introduced errors and true variants.

Methods of the present invention have applications in sample preparation and sequencing. In sample preparation methods, the present invention allows for fragments of both sense and antisense strands of a duplex nucleic acid to be joined together. A linking molecule joins the fragments, creating a complex. The complex can include adapters, primers, and binding molecules in addition to at least the two strands. In samples having low target DNA content such as cancer samples, by linking both strands together, fragments can be amplified and sequenced with increased accuracy with ready identification of sequencing and amplification errors.

Linked fragments may be created through amplification of a nucleic acid fragment with linked amplification primers. In certain embodiments, universal priming sites may be ligated onto the target fragment to create a template molecule. Methods may include droplet workflows and non-droplet workflows and produce linked molecules representing both strands at about at least a 50% rate. In droplet amplification methods, the template molecule may be added to a droplet along with multiplexed gene specific forward and reverse amplification primers and linked universal primers. The droplet can then be subjected to emulsion or digital PCR amplification. The amplified products should be linked copies of the sense and antisense strands of the original fragment. Two or more primers or nucleic acid fragments may be linked by a polyethylene glycol derivative, an oligosaccharide, a lipid, a hydrocarbon, a polymer, or a protein. In certain embodiments, four or more biotinylated primers or nucleic acid fragments may be linked with a streptavidin molecule, or a functionalized nanoparticle. Linked primers of the invention may also include unique cluster identifier sequences to ensure that all cluster reads originate from the same template molecule.

Methods of the invention include duplex identification strategies for droplet formed linked duplex molecules. As noted, droplet based methods of the invention may result in at least a 50% rate of linked duplex fragment formation (linked molecules that contain representations from each side of the DNA duplex) so, identification of those products becomes important in order to omit data from non-duplex products and reap the accuracy increasing benefits of the duplex products. Duplex identification methods may include, for example, a two-stage PCR approach using two sets of primers with different annealing temperatures where several initial cycles are performed at low temperature with gene-specific barcoding primers to amplify and identify each sense of the duplex, while adding a universal tail for subsequent cycles. The number of barcoding cycles is limited to prevent labeling each sense of the duplex with multiple barcodes.

Subsequent cycles may then be performed at high temperature via universal primers because the barcoding primers are unable to bind under those conditions. Duplex products may then be identified by the presence of their sense specific barcodes during sequencing analysis and distinguished from non-duplex clusters. The higher fidelity of duplex cluster seeding can therefore be appreciated.

In non-droplet embodiments, a single amplification cycle may be used to create a linked duplex molecule having both the sense and antisense strands of the original fragment. The linked duplex molecule may then be directly loaded in a flow cell for sequencing, thereby avoiding amplification induced sequence or length biases or (e.g., in whole genome sequencing) as well as avoiding amplification introduced errors and nucleic acid losses from poor loading efficiency. For example, where loading efficiency of a sequencer can be defined as: (number of output reads)/(number of input molecules able to form reads), the loading efficiency for the Illumina MiSeq is <0.1%, and is similar for other Illumina instruments. This is largely due to fluidic losses, since over 600 uL of sample is loaded into the sequencer, while only ~7 uL is retained inside the flow cell for binding, resulting in large losses of starting material. The non-droplet, direct load methods described herein remedy these inefficiencies.

Linked duplex molecule formation may be created by ligating linking adapters to template molecule and extending with strand displacing polymerase to create a linked duplex template with sequencing adapters. In various embodiments, the linking adapters may be linked to an adapter to be ligated to the other end of the template to help ensure that two different adapters are ligated to each molecule, nearly eliminating molecules having two of the same adapters ligated thereto. The linked adapters may include a single linking adapter or may be made up of two linked linking adapters. Linked ligation techniques may be applied to Y-adapters and hairpin adapters as well. Ligation efficiency is improved because binding of one adapter increases the likelihood that the second, linked adapter will bind to the other end of the template molecule. Linkers may comprise PEG, nucleotides, inverted nucleotides, or any of a variety of molecular spacers and linkers known in the art. Linkers may be cleavable (e.g., through UV exposure, uracil, or other digestion) or be bound together through complementary sequences having a binding affinity allowing for denaturing at a selected temperature ($T_m$) allowing for release of the link after ligation.

For direct loading embodiments as well as other applications where the yield of flow cell loading and target capture yield are important, it may be beneficial to combine flow cell loading with targeted sequencing, to minimize loss. Such a combination additionally simplifies the workflow by eliminating an extra step. While methods exist for target capture on the flow cell, they suffer from at least two downsides. First, they are not able to sequence the region that is captured on the flow cell. For short fragments such as cell free DNA, this can amount to a large loss of signal. Secondly, they are unable to capture linked duplex molecules, as described in the invention, for sequencing. Accordingly, methods of the invention include flow cell based target capture of duplex molecules. According to methods of the invention, the flow cell contains one sense of oligos having target regions, while the other sense are hair-pinned and not immediately available for binding. After one sense of linked molecules is captured on the flow cell, the other flow cell oligos are activated to capture the other sense of the linked fragments (e.g., using a uracil digest, enzyme digestion, or light). The template may then be extended and cluster generation may continue as normal.

Methods of the present invention improve base calling when incorporated into amplification techniques. In traditional amplification methods, amplicons are created from a single template. If an error exists in the fragment, the error is propagated through the amplification products. Instead of using a single template, multiple templates (representing each sense of a duplex nucleic acid fragment) are used to create the amplification products. In the event that there is an error developed in one of the strands, the use of both strands, as opposed to a single one, allows such an error to be identified at the sequencing step and differentiated from true variants which are likely to be found in both strands. In certain techniques of the invention, by seeding with multiple templates, errors can be differentiated from true variants through a drop in sequencing quality in a single read at the position where the bases are not the same (a true variant would be present on all reads, providing a strong signal). In embodiments seeding a cluster with a sense and antisense strand, true variants and errors may be identified by comparing results of a first sense read to a second antisense read to confirm the presence of the variant on both template strands.

Methods of the present invention improve amplification on a solid support, such as in the Illumina platform (Illumina, Inc. San Diego, CA) or the Ion Torrent platform (Thermo Fisher Scientific Inc., Waltham, MA). In the Illumina technique, using bridge amplification, clusters of amplicons are formed. If an error exists in the fragment, the error is repeated in the cluster. However, with the present invention, linked duplex fragments are contacted to the solid support. The fragments representing both sense and antisense strands of the original duplex molecule seed the cluster, resulting in a fraction of the total amplicons being derived from each of the strand fragments. This technique allows for an error to be readily determined at the sequencing step as well as aiding in calling true variants and differentiating them from sequencing or amplification (e.g., PCR) errors.

Methods of the invention improve multiplexing amplification processes. In some embodiments of the present invention, linked fragments can be formed in or introduced into a droplet for subsequent amplification. If an error exists in some of the fragments, the error is determinable with the raw sequencing data. In some embodiments, the linked fragments can be bound to a microsphere and then with amplification, the fragments seed the microsphere with amplicons. By providing the advantage of forming a plurality of amplicons using multiple copies of the same fragment, the present invention improves base calling in a variety of applications.

Methods of the invention can be incorporated into multiple sequencing platforms. For example, in traditional sequencing by synthesis, each base is determined sequentially. An error is not determined until bioinformatics techniques are used to analyze the data. However, the present invention allows for duplex fragments of nucleic acids to be linked together during sequencing methodologies. By analyzing multiple fragments simultaneously, agreement between the bases indicates accuracy, while disagreement between the bases would signal an error. With the present invention, errors are determinable from the raw sequencing data, without the application of bioinformatics. This technique uses fewer copies or clusters, increases sequencing throughput, and decreases costs.

BRIEF DESCRIPTION OF THE FIGURES

FIGS. 14A-14D illustrate duplex identification methods according to certain embodiments.

FIG. 38A shows creation of a ligation complex generation of strand invasion of a genomic template using the ligation complex and sing stranded binding protein. FIG. 38B shows subsequent targeted double stranded ligation of the ligation adapter to the genomic template. FIG. 38C shows the results of various second ligations performed on the opposite end of the genomic template. FIG. 38D shows PCR amplification performed on the ligated genomic template using adapter-specific primers.

DETAILED DESCRIPTION

Figure 1:
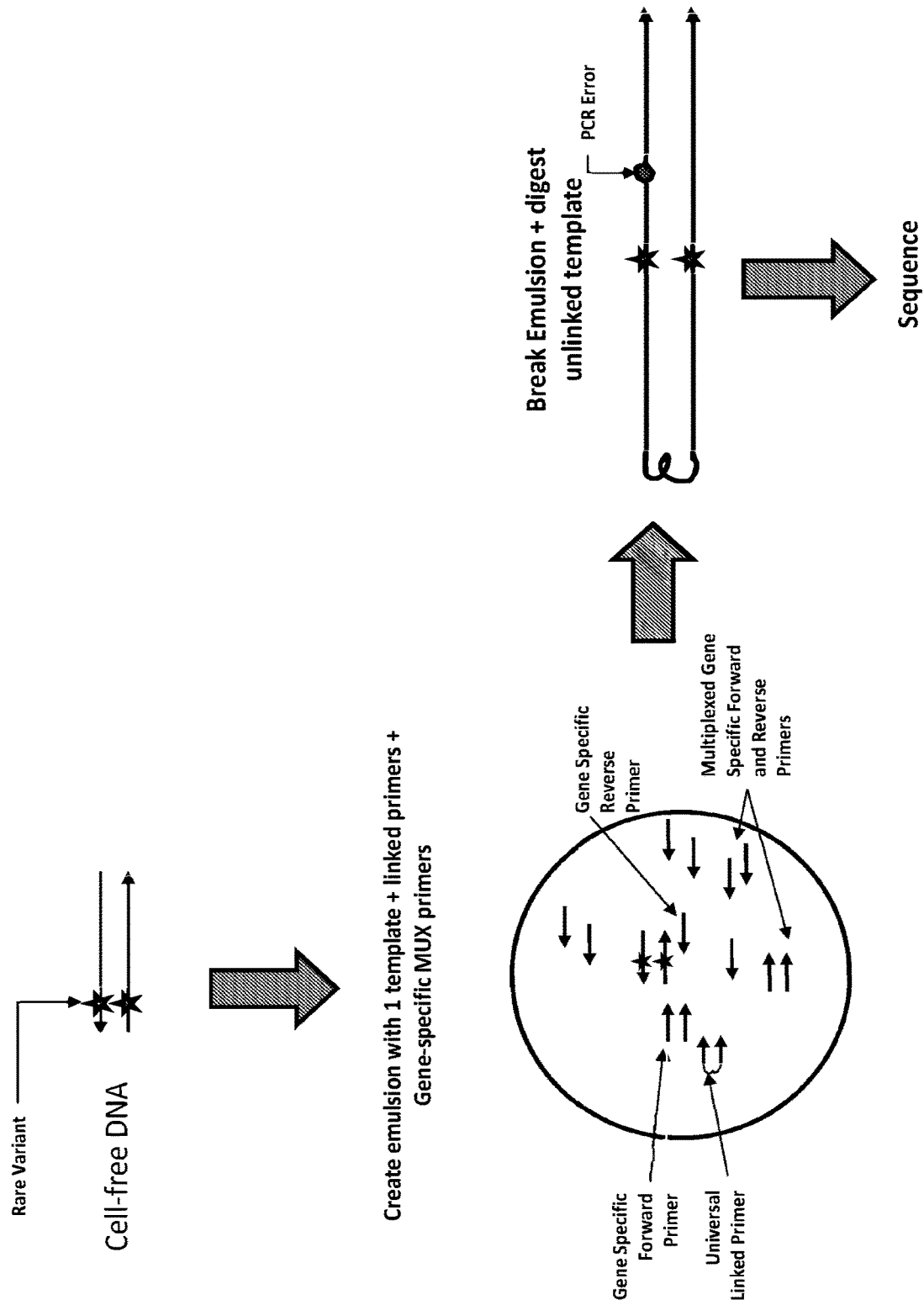
FIG. 1 illustrates a droplet based method of the invention for creating linked duplex nucleic acids.

Methods and compositions of the invention include linked adapter ligation for improving ligation efficiency and target sequence capture while simplifying sequencing workflows. In certain embodiments, the invention relates to methods for amplifying and sequencing nucleic acids by joining both strands of a duplex nucleic acid fragment. The use of both strands reduces error rates, increases efficiency in alignment, and reduces sequencing costs.

Nucleic acid generally is acquired from a sample or a subject. Target molecules for labeling and/or detection according to the methods of the invention include, but are not limited to, genetic and proteomic material, such as DNA, genomic DNA, RNA, expressed RNA and/or chromosome(s). Methods of the invention are applicable to DNA from whole cells or to portions of genetic or proteomic material obtained from one or more cells. Methods of the invention allow for DNA or RNA to be obtained from non-cellular sources, such as viruses. For a subject, the sample may be obtained in any clinically acceptable manner, and the nucleic acid templates are extracted from the sample by methods known in the art. Generally, nucleic acid can be extracted from a biological sample by a variety of techniques such as those described by Maniatis, et al. (Molecular Cloning: A Laboratory Manual, Cold Spring Harbor, N.Y., pp. 280-281, 1982), the contents of which are incorporated by reference herein in their entirety.

Nucleic acid templates include deoxyribonucleic acid (DNA) and/or ribonucleic acid (RNA). Nucleic acid templates can be synthetic or derived from naturally occurring sources. Nucleic acids may be obtained from any source or sample, whether biological, environmental, physical or synthetic. In one embodiment, nucleic acid templates are isolated from a sample containing a variety of other components, such as proteins, lipids and non-template nucleic acids. Nucleic acid templates can be obtained from any cellular material, obtained from an animal, plant, bacterium, fungus, or any other cellular organism. Samples for use in the present invention include viruses, viral particles or preparations. Nucleic acid may also be acquired from a microorganism, such as a bacteria or fungus, from a sample, such as an environmental sample.

In the present invention, the target material is any nucleic acid, including DNA, RNA, cDNA, PNA, LNA and others that are contained within a sample. Nucleic acid molecules include deoxyribonucleic acid (DNA) and/or ribonucleic acid (RNA). Nucleic acid molecules can be synthetic or derived from naturally occurring sources. In one embodiment, nucleic acid molecules are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain embodiments, the nucleic acid molecules are obtained from a single cell. Biological samples for use in the present invention include viral particles or preparations. Nucleic acid molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid molecules can also be isolated from cultured cells, such as a primary cell culture or a cell line. The cells or tissues from which template nucleic acids are obtained can be infected with a virus or other intracellular pathogen. In addition, nucleic acids can be obtained from non-cellular or non-tissue samples, such as viral samples, or environmental samples.

A sample can also be total RNA extracted from a biological specimen, a cDNA library, viral, or genomic DNA. In certain embodiments, the nucleic acid molecules are bound as to other target molecules such as proteins, enzymes, substrates, antibodies, binding agents, beads, small molecules, peptides, or any other molecule and serve as a surrogate for quantifying and/or detecting the target molecule. Generally, nucleic acid can be extracted from a biological sample by a variety of techniques such as those described by Sambrook and Russell, Molecular Cloning: A Laboratory Manual, Third Edition, Cold Spring Harbor, N.Y. (2001). Nucleic acid molecules may be single-stranded, double-stranded, or double-stranded with single-stranded regions (for example, stem- and loop-structures). Proteins or portions of proteins (amino acid polymers) that can bind to high affinity binding moieties, such as antibodies or aptamers, are target molecules for oligonucleotide labeling, for example, in droplets.

Nucleic acid templates can be obtained directly from an organism or from a biological sample obtained from an organism, e.g., from blood, urine, cerebrospinal fluid, seminal fluid, saliva, sputum, stool and tissue. In a particular embodiment, nucleic acid is obtained from fresh frozen plasma (FFP). In a particular embodiment, nucleic acid is obtained from formalin-fixed, paraffin-embedded (FFPE) tissues. Any tissue or body fluid specimen may be used as a source for nucleic acid for use in the invention. Nucleic acid templates can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA.

A biological sample may be homogenized or fractionated in the presence of a detergent or surfactant. The concentration of the detergent in the buffer may be about 0.05% to about 10.0%. The concentration of the detergent can be up to an amount where the detergent remains soluble in the solution. In a preferred embodiment, the concentration of the detergent is between 0.1% to about 2%. The detergent, particularly a mild one that is non-denaturing, can act to solubilize the sample. Detergents may be ionic or nonionic. Examples of nonionic detergents include triton, such as the Triton X series (Triton X-100 t-Oct-C6H4-(OCH2-CH2)xOH, x=9-10, Triton X-100R, Triton X-114 x=7-8), octyl glucoside, polyoxyethylene(9)dodecyl ether, digitonin, IGEPAL CA630 octylphenyl polyethylene glycol, n-octylbeta-D-glucopyranoside (betaOG), n-dodecyl-beta, Tween 20 polyethylene glycol sorbitan monolaurate, Tween 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14E06), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3[(3-cholamidopropyl)dimethylammonio]-1-propanesulf-onate. It is contemplated also that urea may be added with or without another detergent or surfactant.

Lysis or homogenization solutions may further contain other agents, such as reducing agents. Examples of such reducing agents include dithiothreitol (DTT), beta.-mercaptoethanol, DTE, GSH, cysteine, cysteamine, tricarboxyethyl phosphine (TCEP), or salts of sulfurous acid. Once obtained, the nucleic acid is denatured by any method known in the art to produce single stranded nucleic acid templates and a pair of first and second oligonucleotides is hybridized to the single stranded nucleic acid template such that the first and second oligonucleotides flank a target region on the template.

In some embodiments, nucleic acids may be fragmented or broken into smaller nucleic acid fragments. Nucleic acids, including genomic nucleic acids, can be fragmented using any of a variety of methods, such as mechanical fragmenting, chemical fragmenting, and enzymatic fragmenting. Methods of nucleic acid fragmentation are known in the art and include, but are not limited to, DNase digestion, sonication, mechanical shearing, and the like (J. Sambrook et al., "Molecular Cloning: A Laboratory Manual", 1989, 2.sup.nd Ed., Cold Spring Harbour Laboratory Press: New York, N.Y.; P. Tijssen, "Hybridization with Nucleic Acid Probes—Laboratory Techniques in Biochemistry and Molecular Biology (Parts I and II)", 1993, Elsevier; C. P. Ordahl et al., Nucleic Acids Res., 1976, 3: 2985-2999; P. J. Oefner et al., Nucleic Acids Res., 1996, 24: 3879-3889; Y. R. Thorstenson et al., Genome Res., 1998, 8: 848-855). U.S. Patent Publication 2005/0112590 provides a general overview of various methods of fragmenting known in the art.

Genomic nucleic acids can be fragmented into uniform fragments or randomly fragmented. In certain aspects, nucleic acids are fragmented to form fragments having a fragment length of about 5 kilobases or 100 kilobases. In a preferred embodiment, the genomic nucleic acid fragments can range from 1 kilobases to 20 kilobases. Preferred fragments can vary in size and have an average fragment length of about 10 kilobases. However, desired fragment length and ranges of fragment lengths can be adjusted depending on the type of nucleic acid targets one seeks to capture. The particular method of fragmenting is selected to achieve the desired fragment length. A few non-limiting examples are provided below.

Chemical fragmentation of genomic nucleic acids can be achieved using a number of different methods. For example, hydrolysis reactions including base and acid hydrolysis are common techniques used to fragment nucleic acid. Hydrolysis is facilitated by temperature increases, depending upon the desired extent of hydrolysis. Fragmentation can be accomplished by altering temperature and pH as described below. The benefit of pH-based hydrolysis for shearing is that it can result in single-stranded products. Additionally, temperature can be used with certain buffer systems (e.g. Tris) to temporarily shift the pH up or down from neutral to accomplish the hydrolysis, then back to neutral for long-term storage etc. Both pH and temperature can be modulated to affect differing amounts of shearing (and therefore varying length distributions).

Other methods of hydrolytic fragmenting of nucleic acids include alkaline hydrolysis, formalin fixation, hydrolysis by metal complexes (e.g., porphyrins), and/or hydrolysis by hydroxyl radicals. RNA shears under alkaline conditions, see, e.g. Nordhoff et al., Nucl. Acid. Res., 21 (15):3347-57 (2003), whereas DNA can be sheared in the presence of strong acids.

An exemplary acid/base hydrolysis protocol for producing genomic nucleic acid fragments is described in Sargent et al. (1988) Methods Enzymol., 152:432. Briefly, 1 g of purified DNA is dissolved in 50 mL 0.1 N NaOH. 1.5 mL concentrated HCl is added and the solution is mixed quickly. DNA will precipitate immediately, and should not be stirred for more than a few seconds to prevent formation of a large aggregate. The sample is incubated at room temperature for 20 minutes to partially depurinate the DNA. Subsequently, 2 mL 10 N NaOH (OH— concentration to 0.1 N) is added, and the sample is stirred until the DNA re-dissolves completely. The sample is then incubated at 65 degrees C. for 30 minutes in order to hydrolyze the DNA. Resulting fragments typically range from about 250-1000 nucleotides but can vary lower or higher depending on the conditions of hydrolysis.

In one embodiment, after genomic nucleic acid has been purified, it is re-suspended in a Tris-based buffer at a pH between 7.5 and 8.0, such as Qiagen's DNA hydrating solution. The re-suspended genomic nucleic acid is then heated to 65 C and incubated overnight. Heating shifts the pH of the buffer into the low- to mid-6 range, which leads to acid hydrolysis. Over time, the acid hydrolysis causes the genomic nucleic acid to fragment into single-stranded and/or double-stranded products.

Chemical cleavage can also be specific. For example, selected nucleic acid molecules can be cleaved via alkylation, particularly phosphorothioate-modified nucleic acid molecules (see, e.g., K. A. Browne, "Metal ion-catalyzed nucleic Acid alkylation and fragmentation," J. Am. Chem. Soc. 124(27):7950-7962 (2002)). Alkylation at the phosphorothioate modification renders the nucleic acid molecule susceptible to cleavage at the modification site. See I. G. Gut and S. Beck, "A procedure for selective DNA alkylation and detection by mass spectrometry," Nucl. Acids Res. 23(8): 1367-1373 (1995).

Methods of the invention also contemplate chemically shearing nucleic acids using the technique disclosed in Maxam-Gilbert Sequencing Method (Chemical or Cleavage Method), Proc. Natl. Acad. Sci. USA. 74:560-564. In that protocol, the genomic nucleic acid can be chemically cleaved by exposure to chemicals designed to fragment the nucleic acid at specific bases, such as preferential cleaving at guanine, at adenine, at cytosine and thymine, and at cytosine alone.

Mechanical shearing of nucleic acids into fragments can occur using any method known in the art. For example, fragmenting nucleic acids can be accomplished by hydroshearing, trituration through a needle, and sonication. See, for example, Quail, et al. (November 2010) DNA: Mechanical Breakage. In: eLS. John Wiley & Sons, Chichester. doi: 10.1002/9780470015902.a0005 333.pub2.

The nucleic acid can also be sheared via nebulization, see (Roe, B A, Crabtree. J S and Khan, A S 1996); Sambrook & Russell, Cold Spring Harb Protoc 2006. Nebulizing involves collecting fragmented DNA from a mist created by forcing a nucleic acid solution through a small hole in a nebulizer. The size of the fragments obtained by nebulization is determined chiefly by the speed at which the DNA solution passes through the hole, altering the pressure of the gas blowing through the nebulizer, the viscosity of the solution, and the temperature. The resulting DNA fragments are distributed over a narrow range of sizes (700-1330 bp). Shearing of nucleic acids can be accomplished by passing obtained nucleic acids through the narrow capillary or orifice (Oefner et al., Nucleic Acids Res. 1996; Thorstenson et al., Genome Res. 1995). This technique is based on point-sink hydrodynamics that result when a nucleic acid sample is forced through a small hole by a syringe pump.

In HydroShearing (Genomic Solutions, Ann Arbor, Mich., USA), DNA in solution is passed through a tube with an abrupt contraction. As it approaches the contraction, the fluid accelerates to maintain the volumetric flow rate through the smaller area of the contraction. During this acceleration, drag forces stretch the DNA until it snaps. The DNA fragments until the pieces are too short for the shearing forces to break the chemical bonds. The flow rate of the fluid and the size of the contraction determine the final DNA fragment sizes.

Sonication is also used to fragment nucleic acids by subjecting the nucleic acid to brief periods of sonication, i.e. ultrasound energy. A method of shearing nucleic acids into fragments by sonication is described in U.S. Patent Publication 2009/0233814. In the method, a purified nucleic acid is obtained placed in a suspension having particles disposed within. The suspension of the sample and the particles are then sonicated into nucleic acid fragments.

An acoustic-based system that can be used to fragment DNA is described in U.S. Pat. Nos. 6,719,449, and 6,948, 843 manufactured by Covaris Inc. U.S. Pat. No. 6,235,501 describes a mechanical focusing acoustic sonication method of producing high molecular weight DNA fragments by application of rapidly oscillating reciprocal mechanical energy in the presence of a liquid medium in a closed container, which may be used to mechanically fragment the DNA.

Another method of shearing nucleic acids into fragments uses ultrasound energy to produce gaseous cavitation in liquids, such as shearing with Diagonnode's BioRuptor (electrical shearing device, commercially available by Diagenode, Inc.). Cavitation is the formation of small bubbles of dissolved gases or vapors due to the alteration of pressure in liquids. These bubbles are capable of resonance vibration and produce vigorous eddying or microstreaming. The resulting mechanical stress can lead to shearing the nucleic acid in to fragments.

Enzymatic fragmenting, also known as enzymatic cleavage, cuts nucleic acids into fragments using enzymes, such as endonucleases, exonucleases, ribozymes, and DNAzymes. Such enzymes are widely known and are available commercially, see Sambrook, J. Molecular Cloning: A Laboratory Manual, 3rd (2001) and Roberts R J (January 1980). "Restriction and modification enzymes and their recognition sequences," Nucleic Acids Res. 8 (1): r63-r80. Varying enzymatic fragmenting techniques are well-known in the art, and such techniques are frequently used to fragment a nucleic acid for sequencing, for example, Alazard et al, 2002; Bentzley et al, 1998; Bentzley et al, 1996; Faulstich et al, 1997; Glover et al, 1995; Kirpekar et al, 1994; Owens et al, 1998; Pieles et al, 1993; Schuette et al, 1995; Smirnov et al, 1996; Wu & Aboleneen, 2001; Wu et al, 1998a.

The most common enzymes used to fragment nucleic acids are endonucleases. The endonucleases can be specific for either a double-stranded or a single stranded nucleic acid molecule. The cleavage of the nucleic acid molecule can occur randomly within the nucleic acid molecule or can cleave at specific sequences of the nucleic acid molecule. Specific fragmentation of the nucleic acid molecule can be accomplished using one or more enzymes in sequential reactions or contemporaneously.

Restriction endonucleases recognize specific sequences within double-stranded nucleic acids and generally cleave both strands either within or close to the recognition site in order to fragment the nucleic acid. Naturally occurring restriction endonucleases are categorized into four groups (Types I, II III, and IV) based on their composition and enzyme cofactor requirements, the nature of their target sequence, and the position of their DNA cleavage site relative to the target sequence. Bickle T A, Kruger D H (June 1993), "Biology of DNA restriction," Microbiol. Rev. 57 (2): 434-50; Boyer H W (1971). "DNA restriction and modification mechanisms in bacteria". Annu. Rev. Microbiol. 25: 153-76; Yuan R (1981). "Structure and mechanism of multifunctional restriction endonucleases". Annu. Rev. Biochem. 50: 285-319. All types of enzymes recognize specific short DNA sequences and carry out the endonucleolytic cleavage of DNA to give specific fragments with terminal 5'-phosphates. The enzymes differ in their recognition sequence, subunit composition, cleavage position, and cofactor requirements. Williams R J (2003). "Restriction endonucleases: classification, properties, and applications". Mol. Biotechnol. 23 (3): 225-43.

Where restriction endonucleases recognize specific sequencings in double-stranded nucleic acids and generally cleave both strands, nicking endonucleases are capable of cleaving only one of the strands of the nucleic acid into a fragment. Nicking enzymes used to fragment nucleic acids can be naturally occurring or genetically engineered from restriction enzymes. See Chan et al., Nucl. Acids Res. (2011) 39 (1): 1-18.

In some embodiments, DNA is sheared in biological processes within an organism, or a biological medium. Such DNA, or cell-free DNA, circulates freely in the blood stream. For example, cell-free tumor DNA (ctDNA) is tumor DNA that circulates freely in the blood stream. Some embodiments use fragmented or sheared DNA, however, the DNA is obtained in fragmented form.

In preferred embodiments of the present invention, the strands of duplex nucleic acid fragments are joined together in a complex, for example, see FIG. 1. Any linking molecule may be used to join the molecules. The linker used in the present invention may be synthesized or obtained commercially from various companies, for example, Integrated DNA Technologies, Inc., Gene Link, Inc., and TriLink Biotechnologies, Inc. The linker may be any molecule to join two primers or two nucleic acid fragments. The linking molecule may also join multiple fragments together. Any number of fragments may be incorporated to the complex.

FIG. 1 illustrates a droplet based method of the invention for creating linked duplex nucleic acids from the sense and antisense strands of a nucleic acid fragment. As shown, a double stranded cell-free DNA (cfDNA) having a rare variant on represented on both strands can be obtained. The double stranded template may then be added to an emulsion with one or more gene specific forward primers (e.g., the emulsion may contain multiplexed forward and reverse primers specific to more than one gene or part of a gene), one or more gene specific reverse primers, a universal linked primer. The emulsion may be subjected to emulsion PCR to create linked, duplex products. The emulsion can then be broken and unlinked template digested. The remaining, linked duplex products may then be sequenced. Because double stranded product enters droplet, with forward and reverse gene-specific primers, duplex sequence information may be obtained. The linked products of the emulsion PCR contain both template senses at least about 50% of time, which lowers average error rate. As shown in FIG. 1, a PCR error is introduced into the duplex product during the emulsion PCR but, because the PCR error is only present on one strand and the true variant is present on both, the two can be easily differentiated from each other during sequencing.

Figure 2:
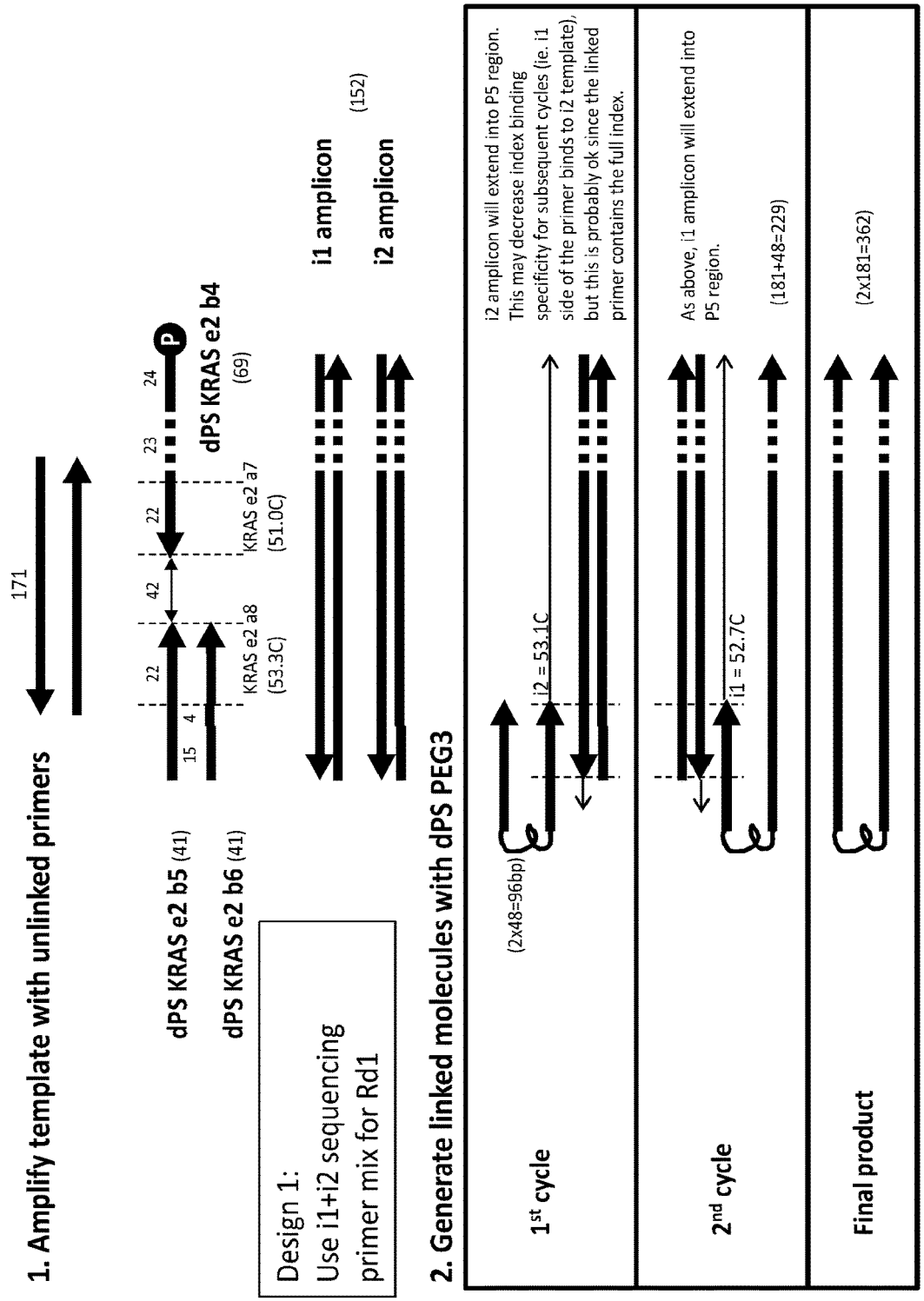
FIG. 2 depicts an exemplary linked primer and forward and reverse gene specific primers and their use according to one method of the invention.
Figure 3:
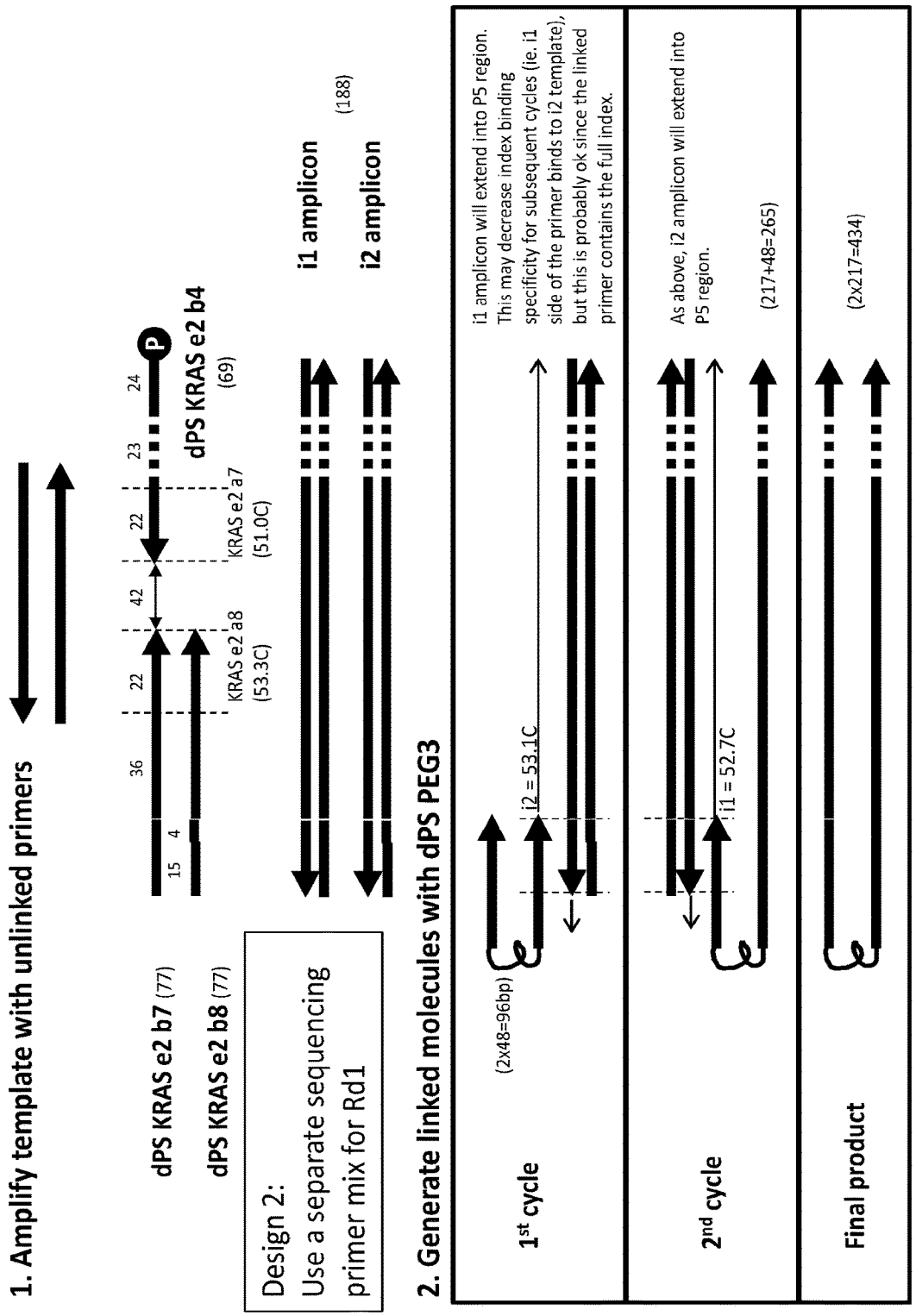
FIG. 3 depicts an exemplary linked primer and forward and reverse gene specific primers and their use according to one method of the invention.
Figure 4:
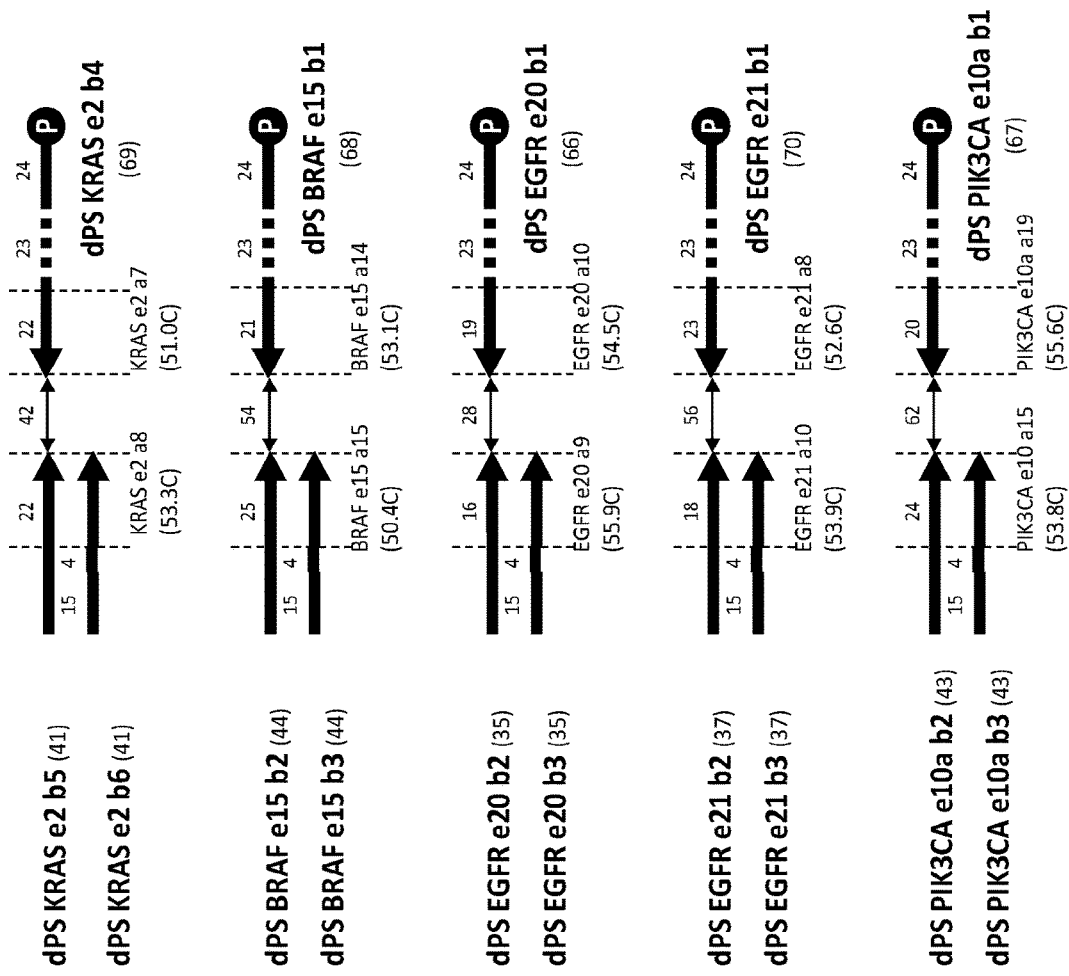
FIG. 4 shows gene specific primers of the invention.

FIGS. 2 and 3 show exemplary universal linked primers and forward and reverse gene specific primers and methods for their use in PCR amplification to create linked duplex products. Preferably, the amplicon length is kept short to improve sensitivity. In the examples, the target region between primers is about 86 bp. Additional gene specific primers are shown in FIG. 4.

Figure 5:
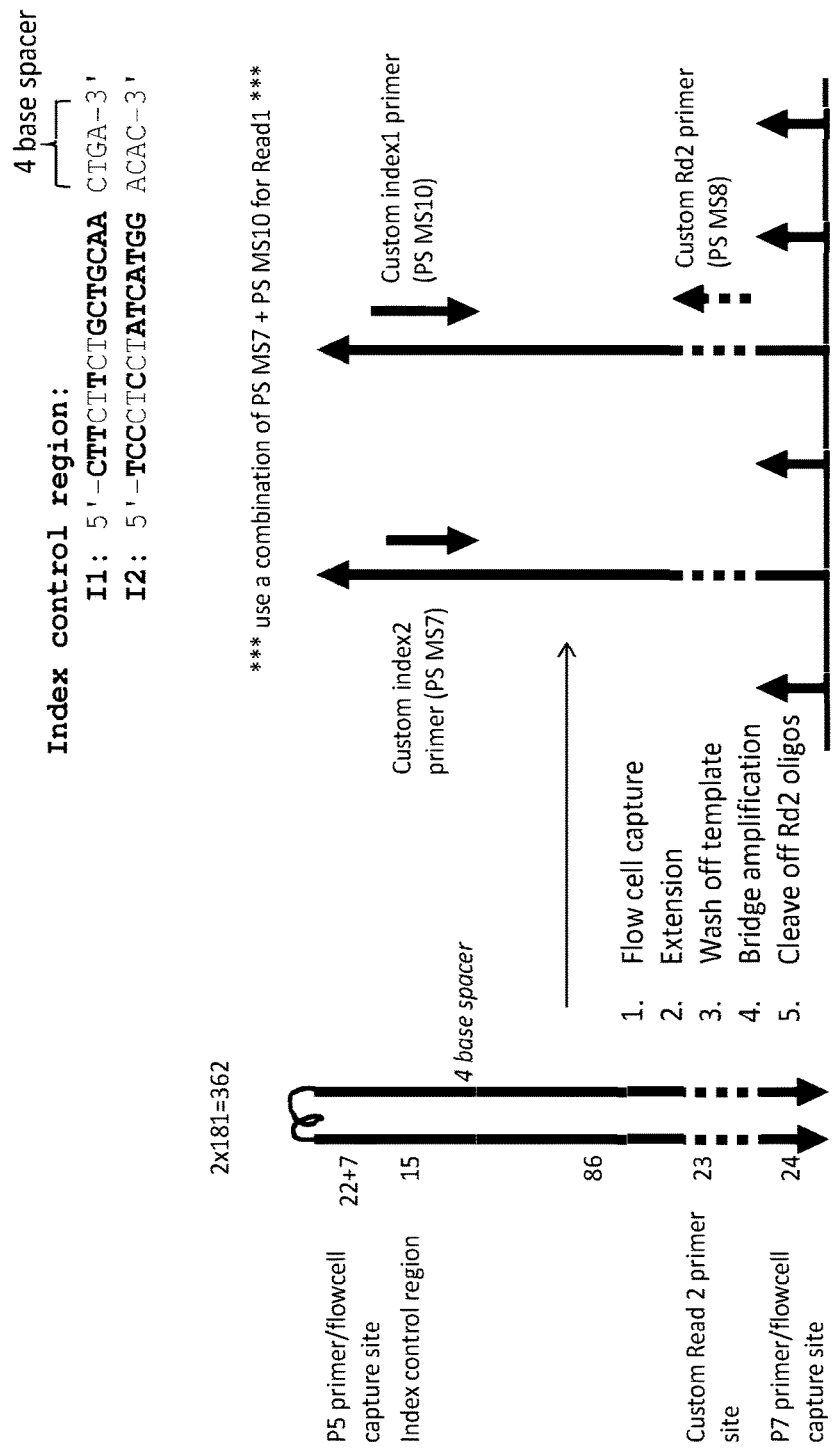
FIG. 5 depicts a sequencing method of the invention with products methods shown in FIG. 2.
Figure 6:
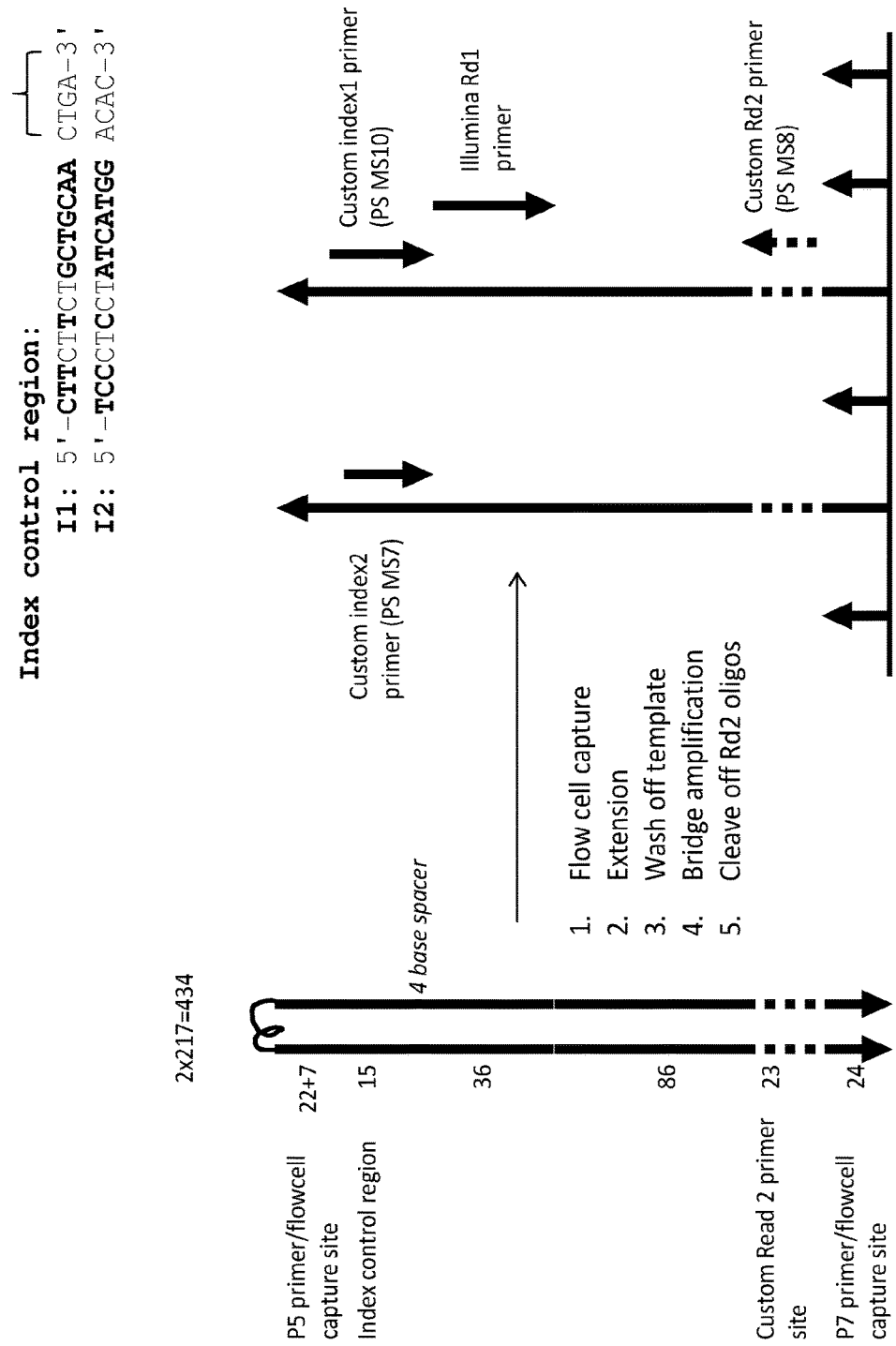
FIG. 6 depicts a sequencing method of the invention with products methods shown in FIG. 3.

FIGS. 5 and 6 illustrate sequencing methods of the invention using the products derived from FIGS. 2 and 3 respectively. The linked primers may contain two or more sites and may be made of PEG, Traptavidin bound to biotinylated DNA, DNA coated beads, DNA-coated nanoparticles, DNA-linked to gel based beads (e.g., acrylamide). Beads may be polystyrene, latex, magnetic, silica, ferromagnetic or similar materials. Attachment can be by conventional methods and preferably by a combination of amino and carboxyl groups.

Methods of the invention may include duplex identification strategies for droplet formed linked duplex molecules. As noted, droplet based methods of the invention may result in at least a 50% rate of linked duplex fragment formation (linked molecules that contain representations from each side of the DNA duplex) so, identification of those products becomes important in order to omit data from non-duplex products and reap the accuracy increasing benefits of the duplex products. Duplex identification methods may include, for example, a two-stage PCR approach using two sets of primers with different annealing temperatures where several initial cycles are performed at low temperature with gene-specific barcoding primers to amplify and identify each sense of the duplex, while adding a universal tail for subsequent cycles. The number of barcoding cycles is limited to prevent labeling each sense of the duplex with multiple barcodes.

Subsequent cycles may then be performed at high temperature via universal primers because the barcoding primers are unable to bind under those conditions. Duplex products may then be identified by the presence of their sense specific barcodes during sequencing analysis.

FIGS. 14A-D illustrate duplex identification methods according to certain embodiments of the invention. In the illustrated example, the following may be added to the droplet: a linking primer; a universal forward primer and a universal reverse primer, each having a high Tm (Tm may be increased using LNA); a barcoded forward gene specific primer and a barcoded reverse gene specific primer, each having a lower Tm and at a lower concentration than the universal forward primer; and the duplex template. Emulsion PCR may then be run with a first cycle having a low annealing temperature to allow the barcoded primers to bind the template followed by a second low annealing temperature cycle to produce the products shown in FIG. 14B. A third low annealing temperature cycle allows the first cycle of universal primer binding. In this cycle, barcoded primers will still bind [A+B] to form more or the C and D products, and may also bind C and D products to form more E and F products.

Figure 14A:
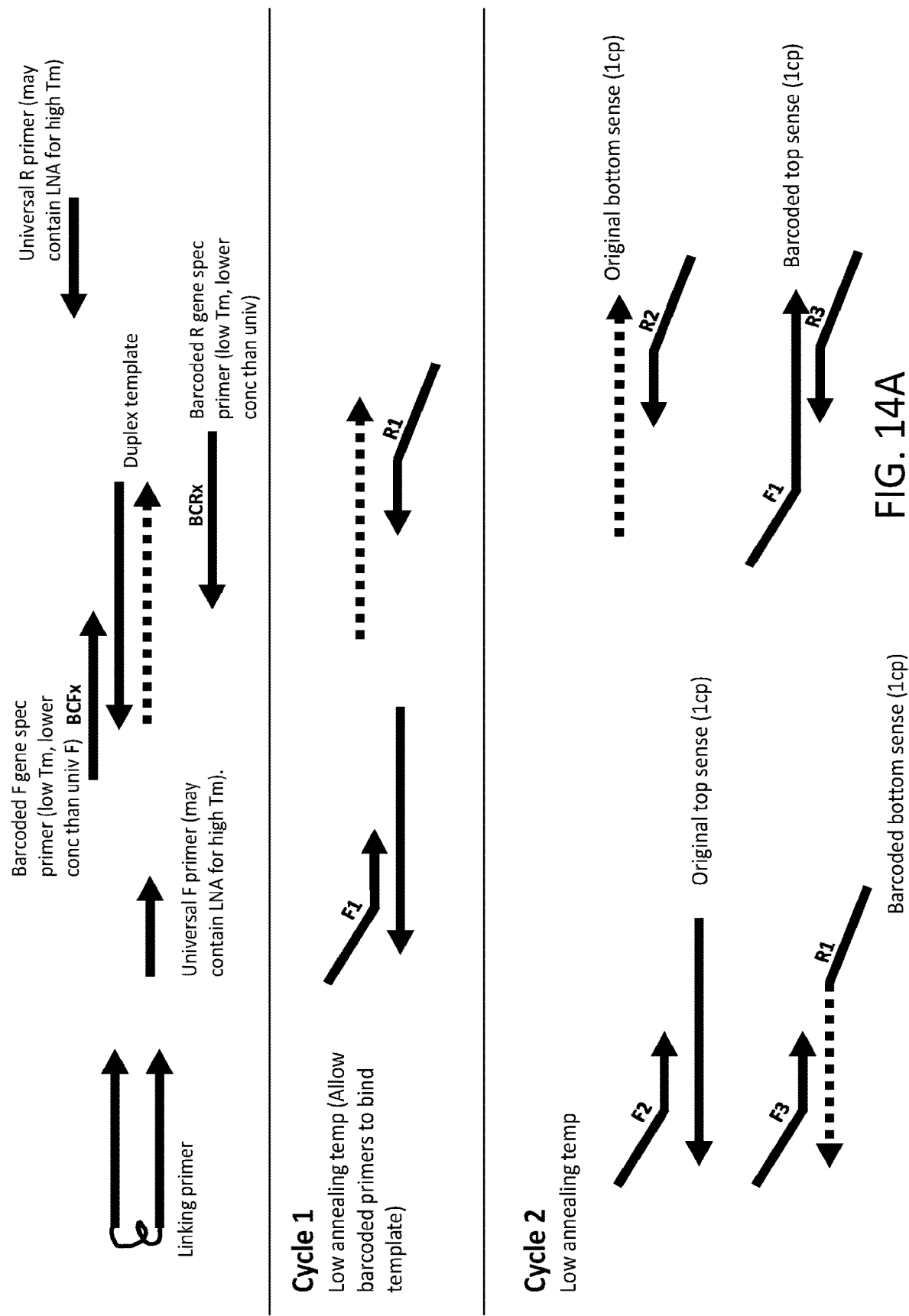
Figure 14B:
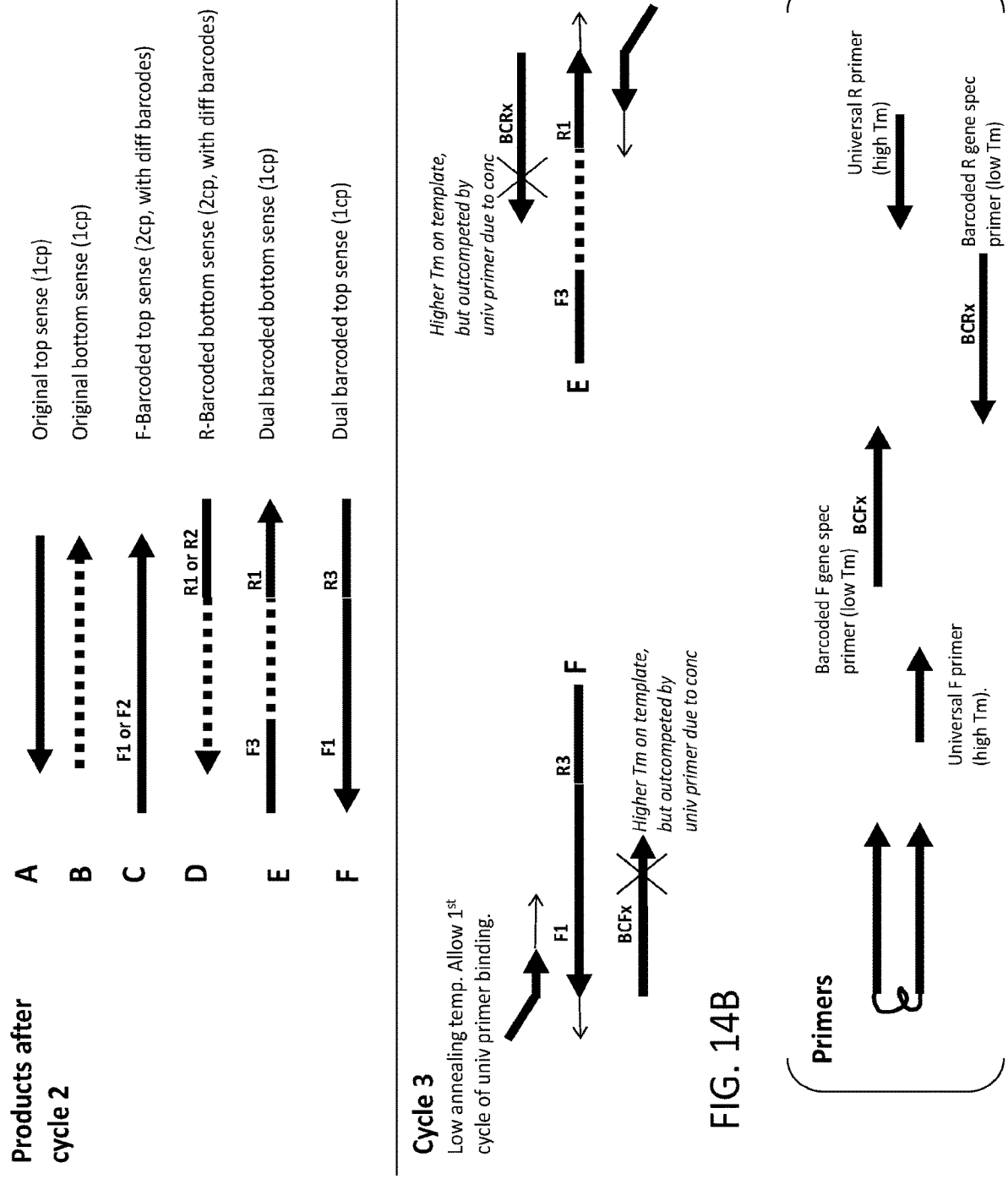
Figure 14C:
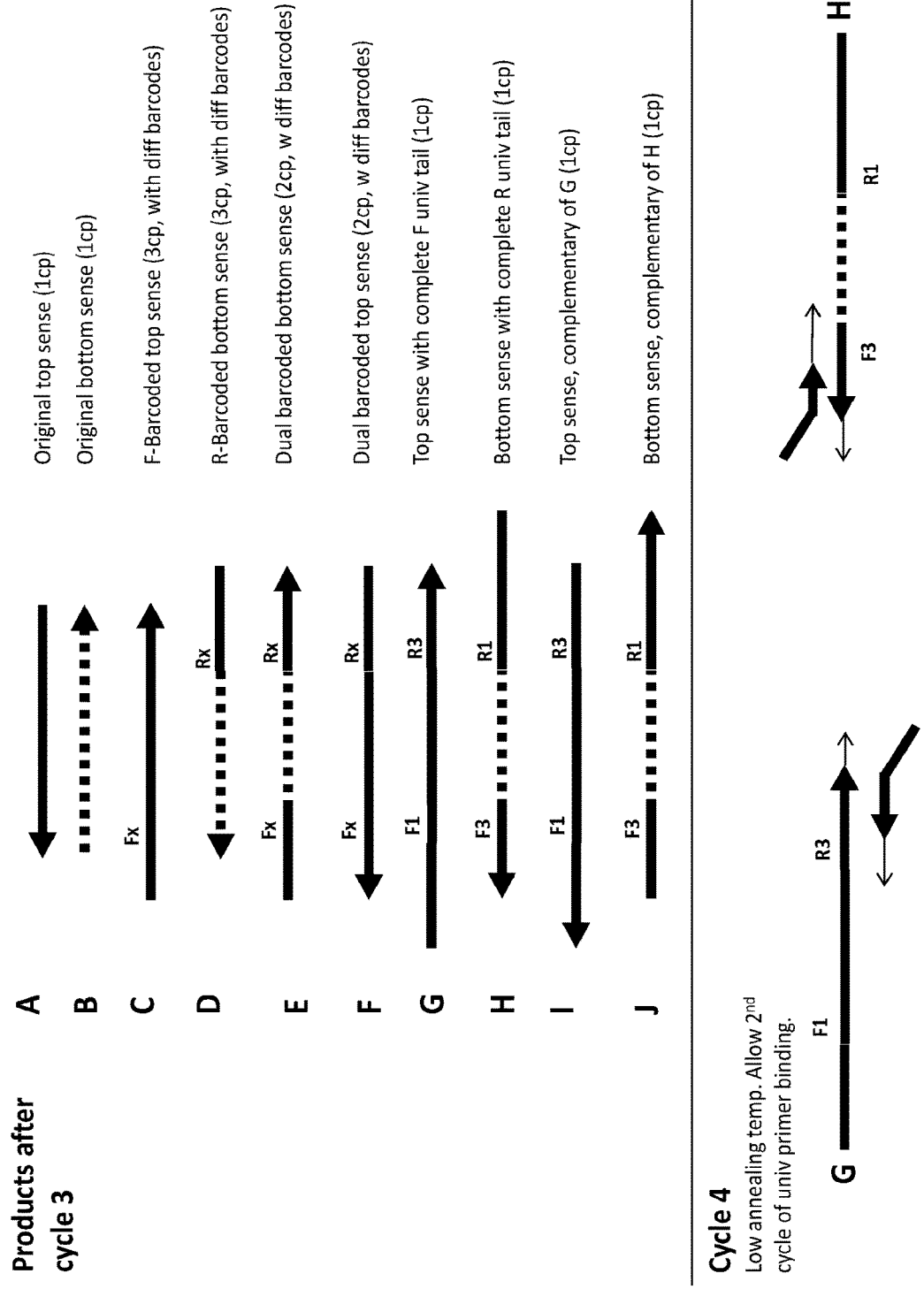

After the third cycle, the products shown in FIG. 14C may be present in the emulsion, which may then be subjected to a 4th low annealing temperature cycle to allow a second cycle of universal primer binding. At the end of cycle 4, molecules with the full forward and reverse universal tails may be obtained as shown in FIG. 14C. The annealing temperature may be increased for subsequent cycles. There may be some I and J type products having different barcodes (e.g., they have the full universal tails on either the forward or reverse side). They can only amplify linearly at a higher annealing temp.

The subsequent PCR cycles (5+) may have an increased annealing temperature only allowing binding of universal primers to amplicons with a full universal tail as shown in FIG. 14D. The last few cycles may be at a low annealing temperature to allow the linking of amplified strands via a portion of the forward universal tail. Alternatively, a longer linked primer may be used with the full forward universal tail which allows linking at higher annealing temperatures but is harder to synthesize and may be less efficient in linking. Linking top or bottom sense occurs at random so 50% of linked molecules using this linked primer should have 1 of each (duplex info). Linked primers with more than 2 sites, for example 100 sites on a nanoparticle, on average contain duplex information nearly 100% of the time.

In certain embodiments, linked duplex molecules may be created without the use of emulsion PCR. In non-droplet embodiments, a single amplification cycle may be used to create a linked duplex molecule having both the sense and antisense strands of the original fragment. The linked duplex molecule may then be directly loaded in a flow cell for sequencing, thereby avoiding amplification induced sequence or length biases or (e.g., in whole genome sequencing) as well as avoiding amplification introduced errors and nucleic acid losses from poor loading efficiency. For example, where loading efficiency of a sequencer can be defined as: (number of output reads)/(number of input molecules able to form reads), the loading efficiency for the Illumina MiSeq is <0.1%, and is similar for other Illumina instruments. This is largely due to fluidic losses, since over 600 uL of sample is loaded into the sequencer, while only ~7 uL is retained inside the flow cell for binding, resulting in large losses of starting material. The non-droplet, direct load methods described herein remedy these inefficiencies. Methods of the invention may include a simplified workflow that creates duplex molecule with one cycle of PCR. The duplex molecules can then be used to seed a single cluster and provide high accuracy sequencing reads. By loading the flow cell directly and then sequencing, DNA losses through loading are minimized.

Direct load, non-droplet methods of the invention have applications including whole genome sequencing where a small mass of DNA is present, but high accuracy is desired, such as tissue biopsy, needle aspirates, or small volume blood draws. Additional applications may include those where DNA is degraded or damaged, such as in formalin-fixed, paraffin-embedded (FFPE) samples.

Figure 7A:
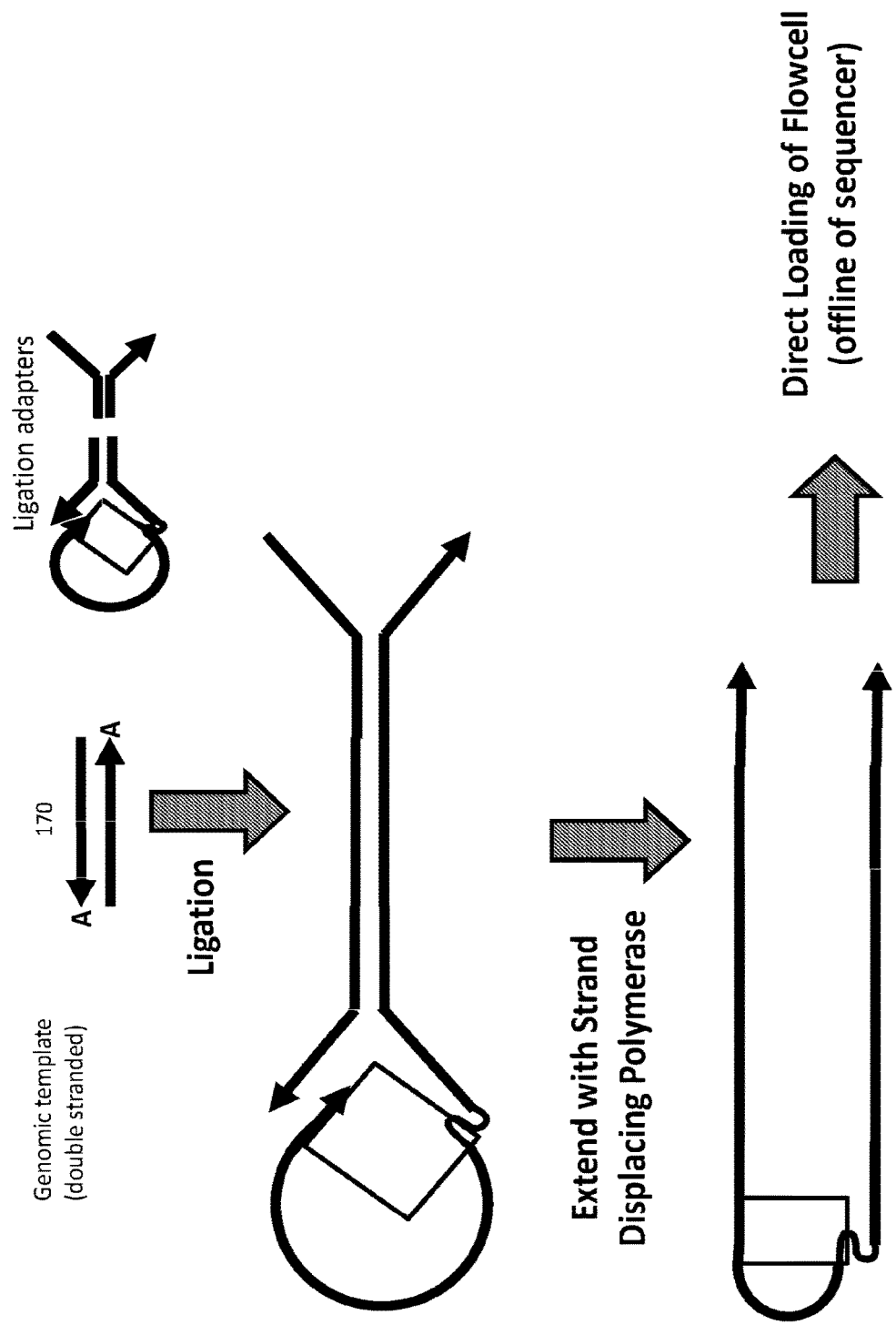
FIGS. 7A and 7B show a non-droplet linked duplex formation method using one linking adapter.
Figure 7B:
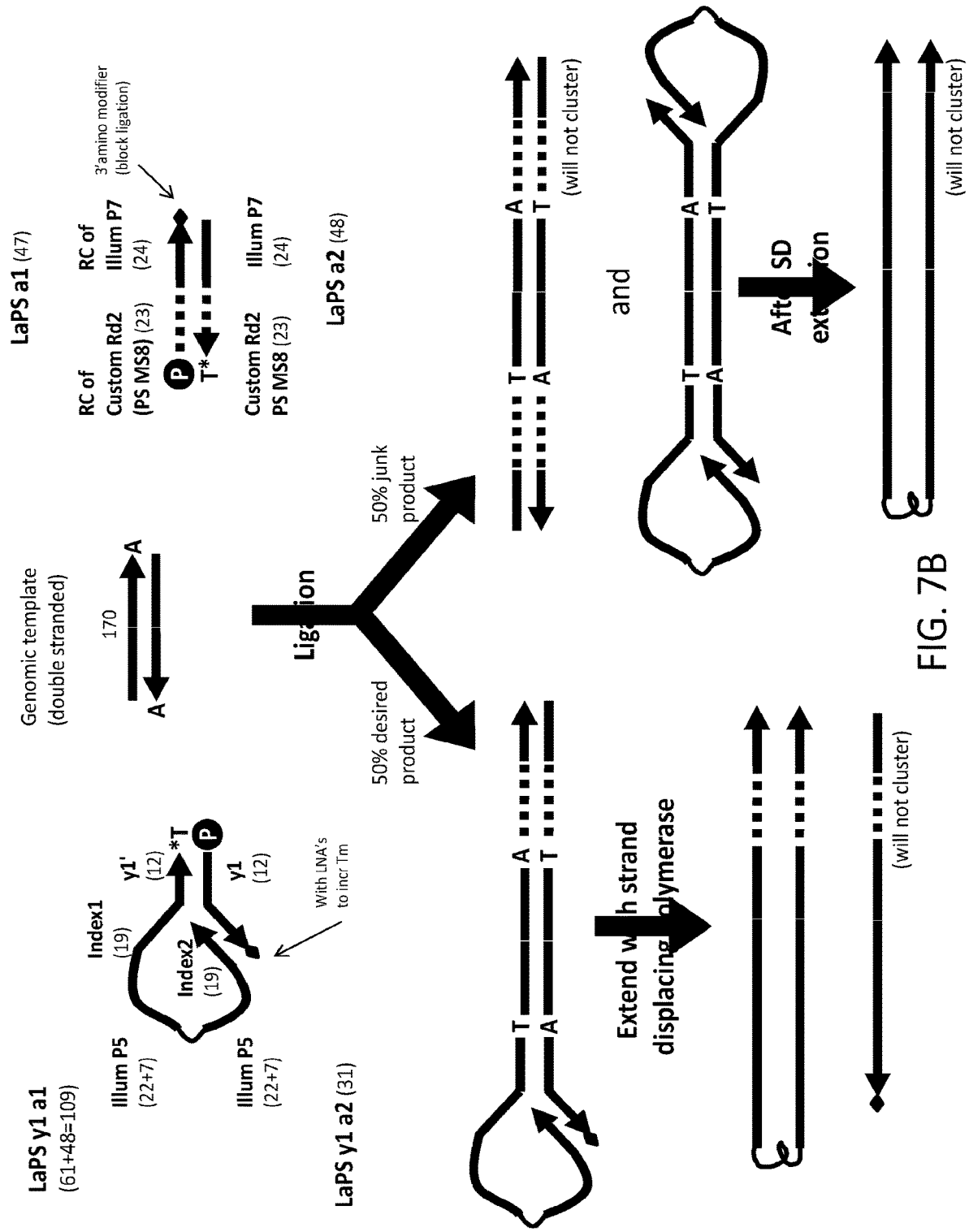
Figure 8A:
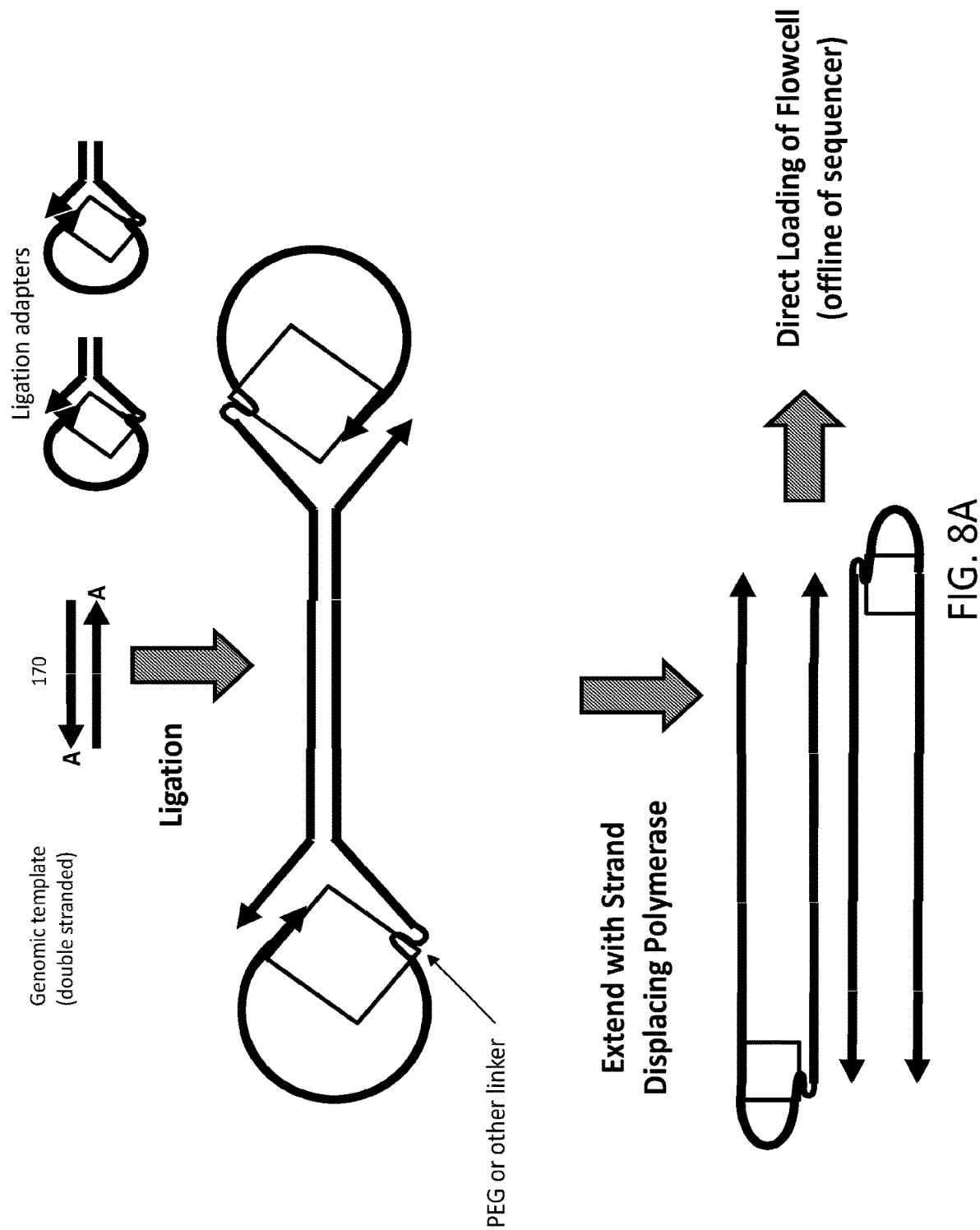
FIGS. 8A and 8B show a non-droplet linked duplex formation method using two linking adapters.
Figure 8B:
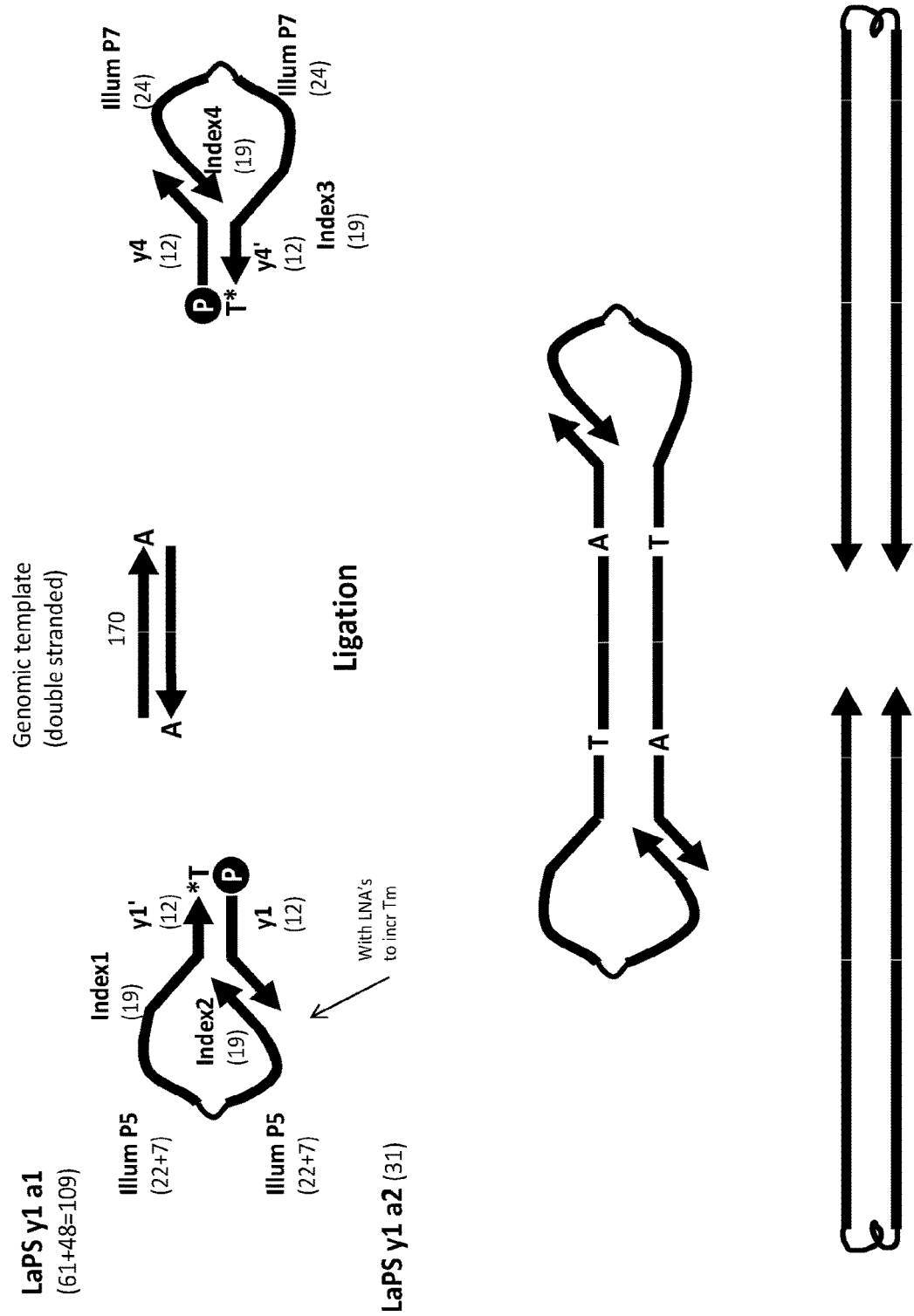

FIGS. 7A, 7B, 8A, and 8B show non-droplet linked duplex formation methods according to certain embodiments of the invention. One (FIG. 7) or two (FIG. 8) linking adapters are ligated onto the double stranded genomic template and then extended using a strand displacing polymerase to create the linked duplex molecule. The linked duplex may then be directly loaded to a flow cell for sequencing. In two linking adapter applications such as illustrated in FIG. 8, linked fragments may be formed in two orientations (i.e., linked fragments having the linker on one end and linked fragments having the linker on the opposite end). As shown in FIGS. 7B and 8B, ligation may result in about 50% the desired, linked duplex product where other undesired products will not form clusters.

In various embodiments, the linked adapter ligation techniques described herein may be applied to double stranded adapters as shown in FIGS. 7A and 8A to help ensure that two different adapters ligate to a single DNA molecule where ligation of the first adapter to one end of the genomic template brings the second adapter into close proximity, increasing the probability of the second adapter ligating onto the other end of the template.

Figure 34:
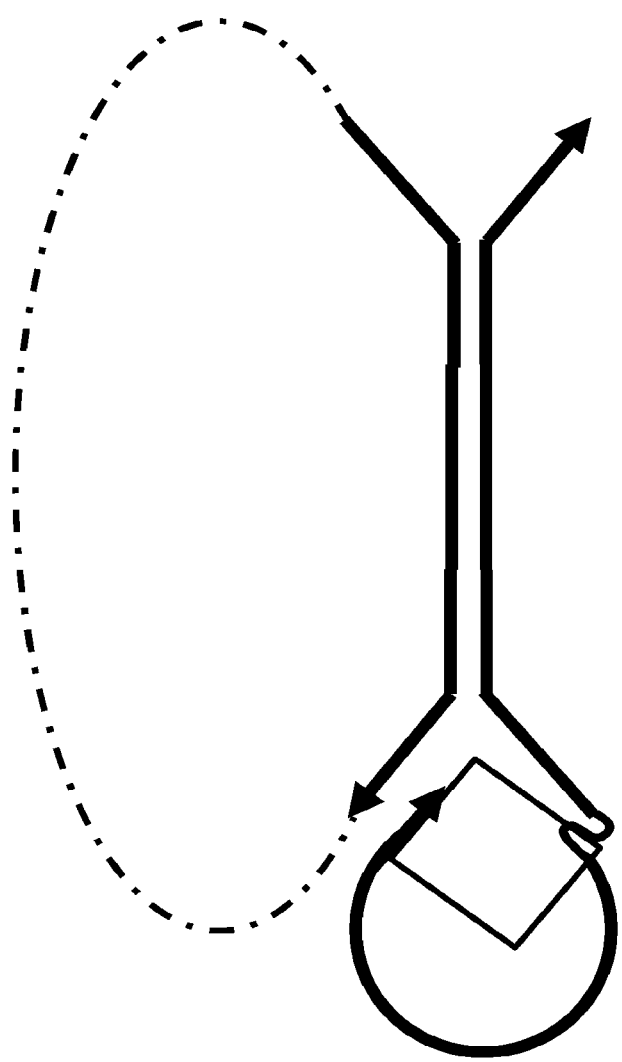
FIG. 34 shows an exemplary configuration of linked adapters including one linking adapter.
Figure 35:
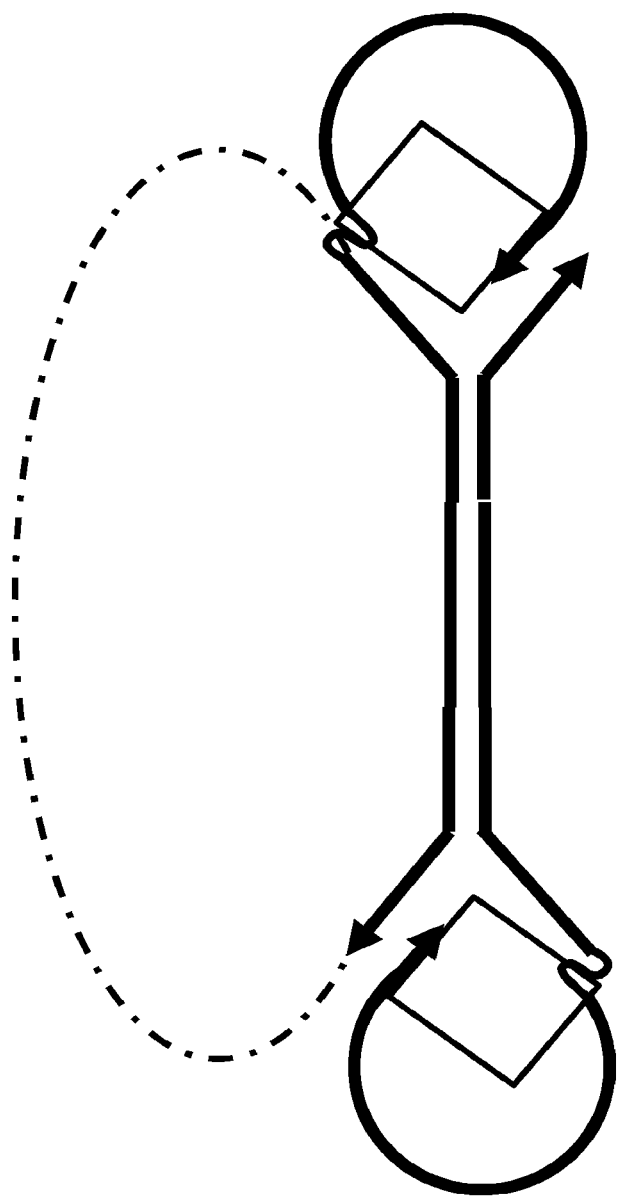
FIG. 35 shows one exemplary configuration of linked adapters including two linking adapters.
Figure 36:
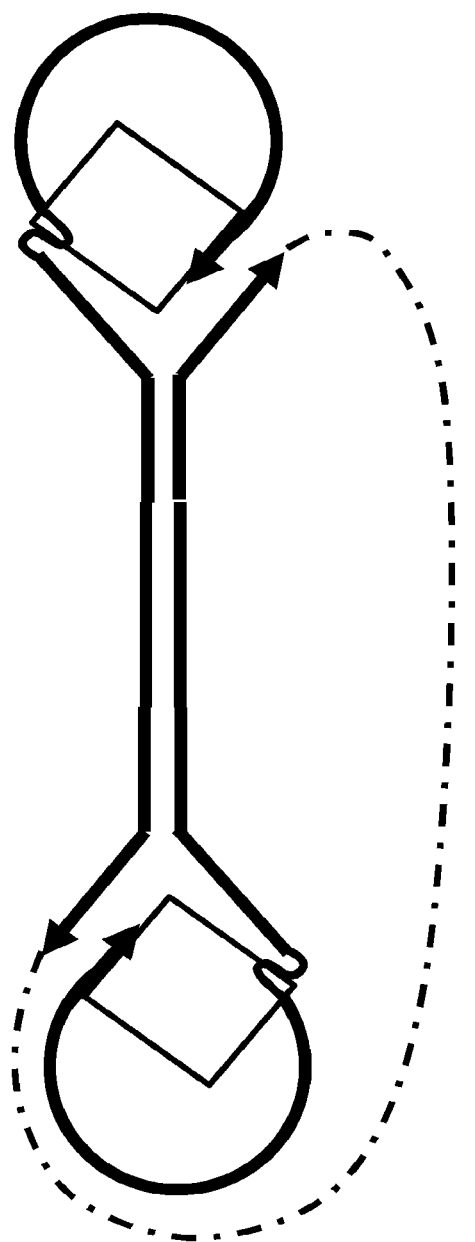
FIG. 36 shows another exemplary configuration of linked adapters including two linking adapters.

FIG. 34 illustrates linked double stranded adapters ligated to a template where one of the double stranded adapters is a linking-type adapter as used in FIG. 7A to create a linked template molecule through strand displacement. FIGS. 35 and 36 show linked double stranded adapters including two linking adapters as shown in FIGS. 8A and 8B for creating two linked template molecules through strand displacement. FIGS. 35 and 36 show alternative connection points for linkers connecting the two double stranded adapters.

Figure 37:
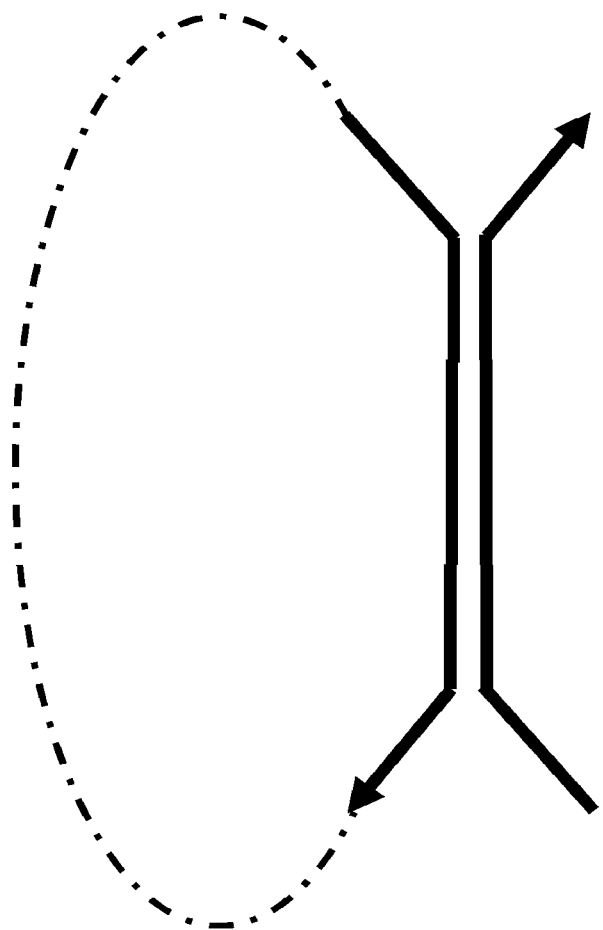
FIG. 37 shows an exemplary configuration of linked Y-adapters.

Linked adapter ligation methods may be used to increase ligation efficiency over traditional ligation methods. FIG. 37 depicts linked Y-adapters ligated to template DNA. Even when ligating two of the same Y-adapters, because one side binding brings the second adapter into close proximity with the other side of the template, both ends of the template are likely to bind the Y-adapters. Linked adapter ligation may also be used on single stranded DNA.

Figure 9A:
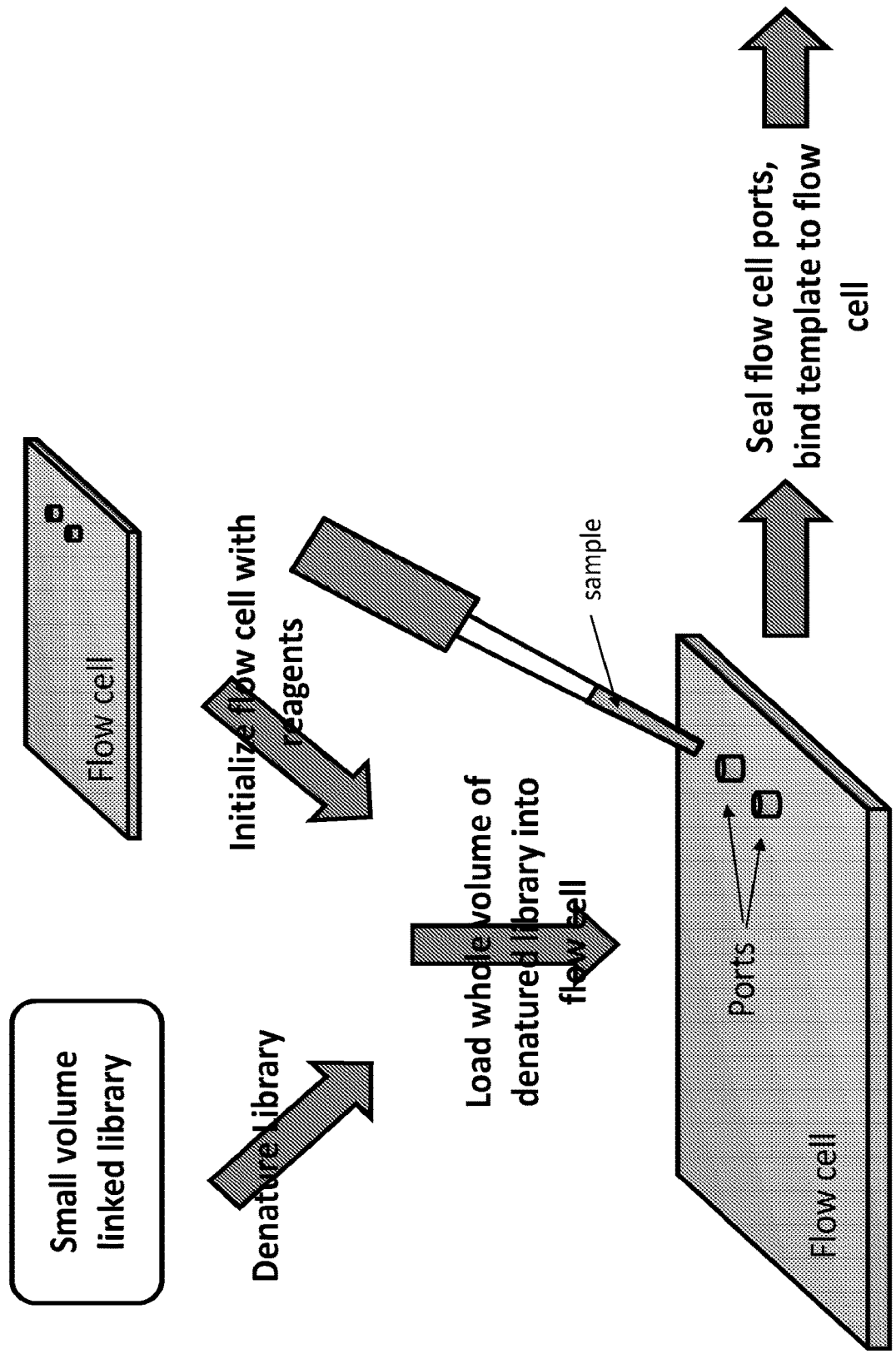
FIGS. 9A and 9B illustrate steps of a direct loading sequencing method using linked duplex molecules.
Figure 9B:
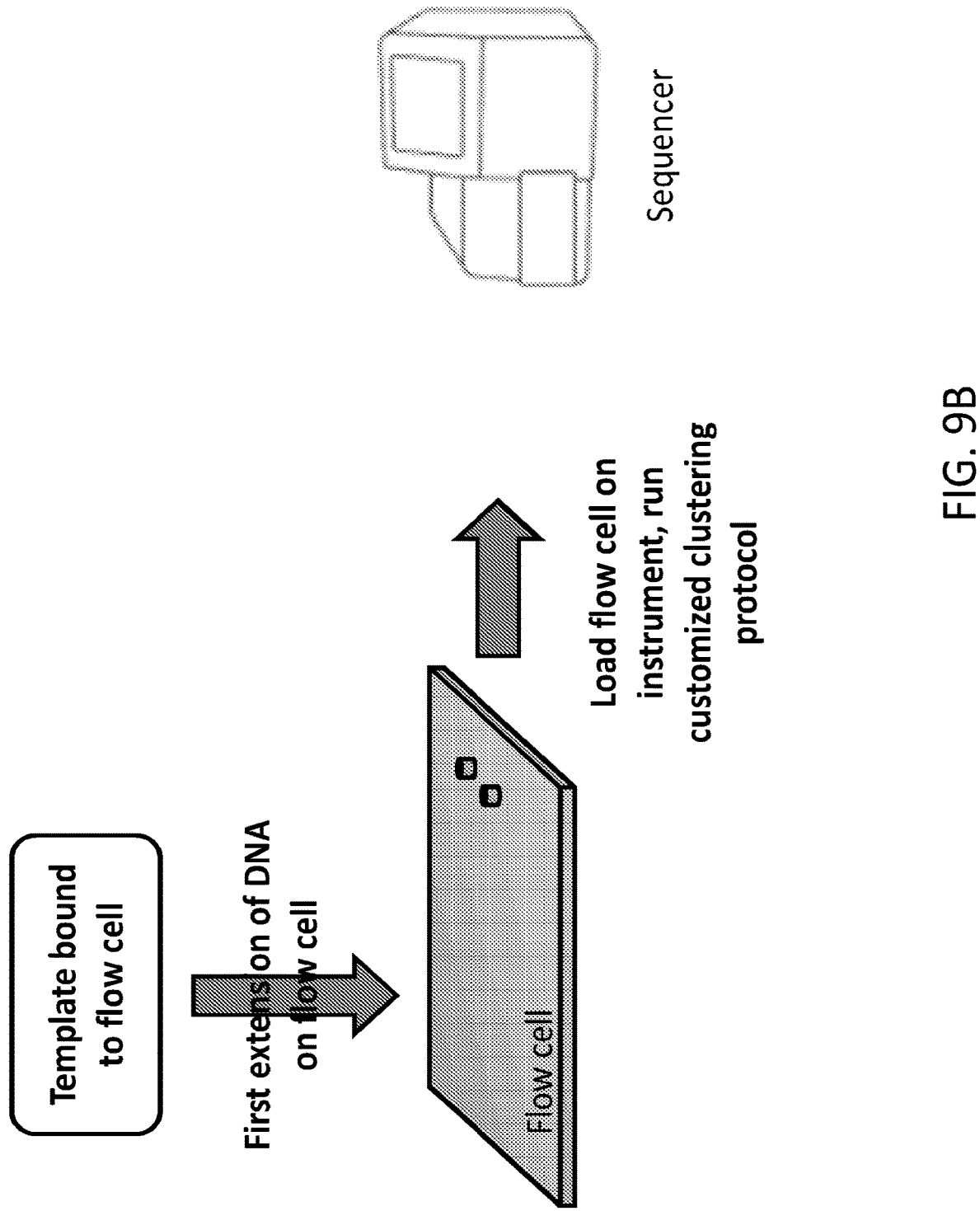
Figure 10:
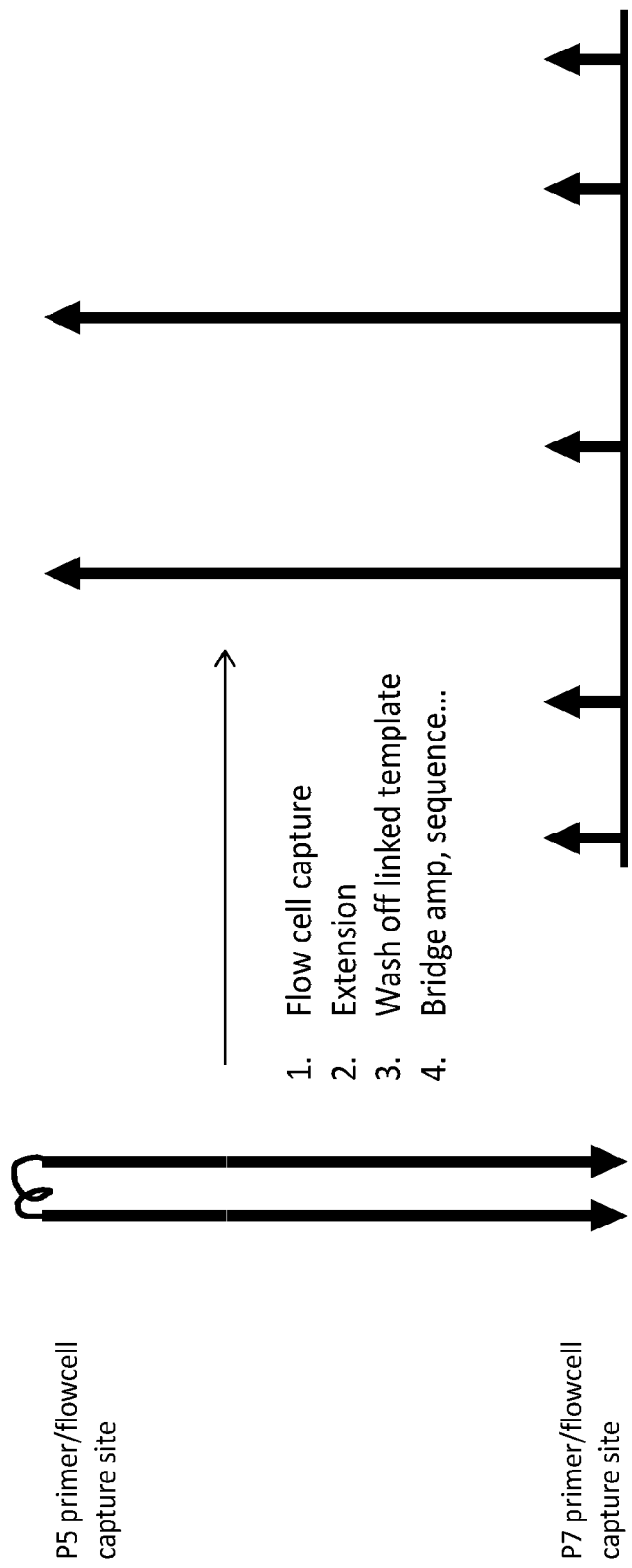
FIG. 10 shows exemplary steps of a flow cell binding method.

FIGS. 9A and 9B illustrate steps of a direct loading sequencing method using linked duplex molecules. In the exemplary method of FIGS. 9A and 9B, a flow cell is initialized with reagents. A small volume linked library is then denatured and the whole volume loaded onto the initialized flow cell. The flow cell ports are then sealed and the template such as created in the methods illustrated in FIGS. 7 and 8, is bound to the flow cell. The DNA on the flow cell is extended and then the flow cell is loaded on the flow cell sequencing instrument. Exemplary flow cell binding is illustrated in FIG. 10 including the steps of flow cell capture, extension, washing off of linked template, bridge amplification, and sequencing. Binding for the other sense strand of linked duplex template is analogous to that illustrated in FIG. 10.

Figure 11:
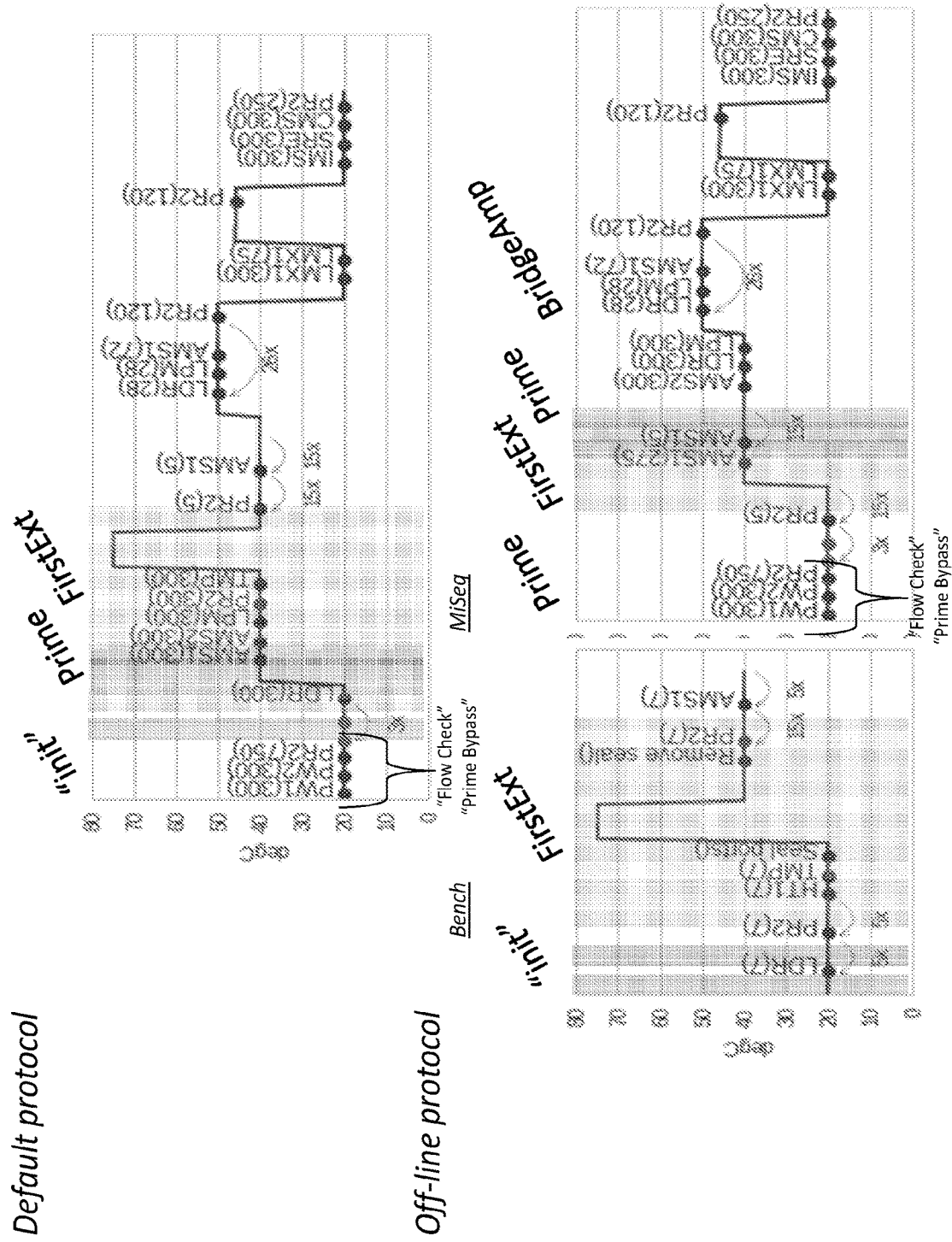
FIG. 11 depicts an exemplary off-line flow cell preparation protocol.

FIG. 11 illustrates an exemplary off-line seeding protocol compared to a default protocol. In certain embodiments, steps of the off-line seeding protocol may include performing the following steps at the bench at room temperature: flush with LDR×5, flush with PR2×5, flush with HT1, load TMP, and seal ports with PCR tape, where flush means filling the flow cell with the specified reagent, waiting about 10 seconds, and then emptying the flow cell. After sealing the ports with PCR tape, the flow cell is incubated in a bead bath at 75 degrees Celsius for 10 minutes, followed by incubation at 40 degrees Celsius for 10 minutes. Returning the flow cell to the bench at room temperature, the seal is removed, and the flow cell is flushed with PR2 at 40 degrees Celsius 5 times, flushed with AMS1 2 times, flushed with AMS1 with a two minute incubation at 40 degrees Celsius 3 times, filled with AMS1, and transferred to a MiSeq instrument (commercially available from Illumnia, Inc, San Diego, CA) for sequencing. Additional steps in the preparation protocol may include taking the flow cell out from its plastic housing, pre-cutting PCR tape for sealing ports, and protecting the flow cell from scratches from bead bath, with PCR tape or scotch tape on both sides.

Figure 30:
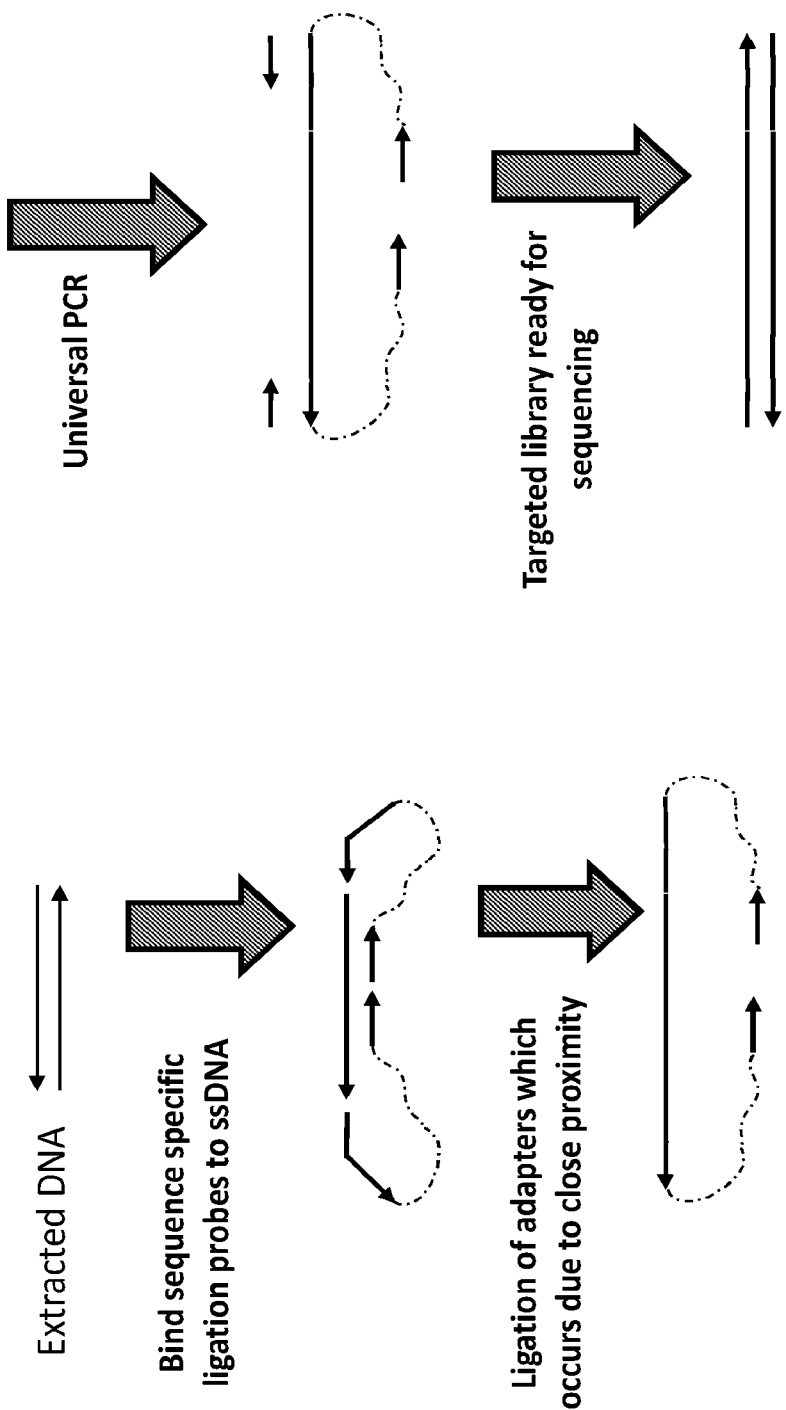
FIG. 30 shows exemplary steps of solution-based linked ligation.

Linked ligation adapters of the invention may be used for target capture and selective amplification of target templates. Linked ligation adapters may be used with single stranded DNA (ssDNA) or, in certain embodiments, may be used with double stranded DNA (dsDNA). FIG. 30 shows an exemplary use of linked ligation adapters of the invention. Linked ligation adapters include adapters that may be sequencing adapters or comprise universal priming sites and are linked to target sequence specific probes. The probes are complimentary to at least a portion of the target template ssDNA. The probes bind the template ssDNA strand, bringing their linked adapter into close proximity to the template and allowing for ligation of the adapters to the ends of the ssDNA template. The universal priming sites in the ligated adapters then allow for PCR amplification of the target template using universal PCR without amplifying off target nucleic acids. This results in a targeted library including sequencing adapters and ready for sequencing.

Figure 38A:
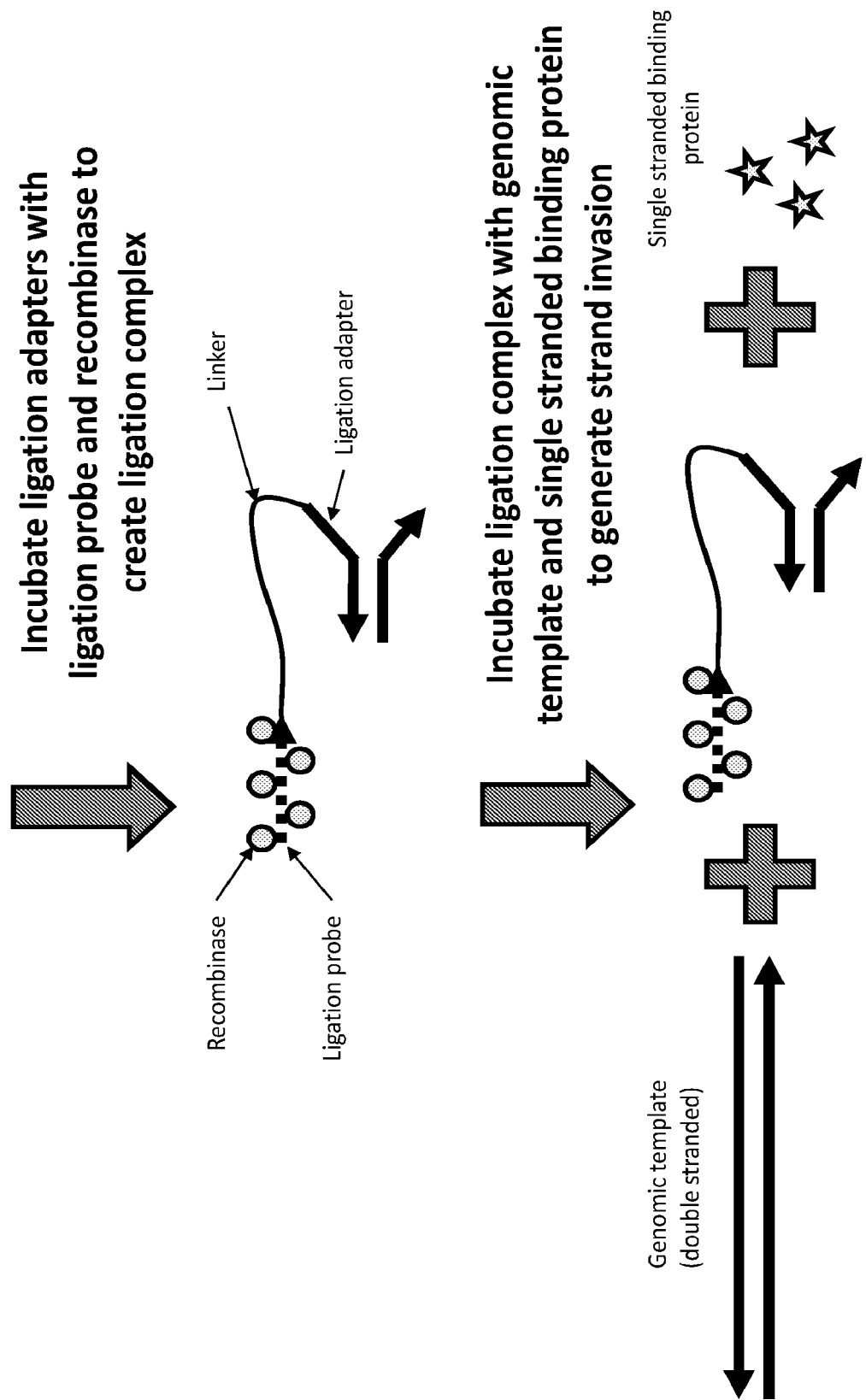
FIGS. 38A-D show exemplary methods of double stranded linked ligation.
Figure 38B:
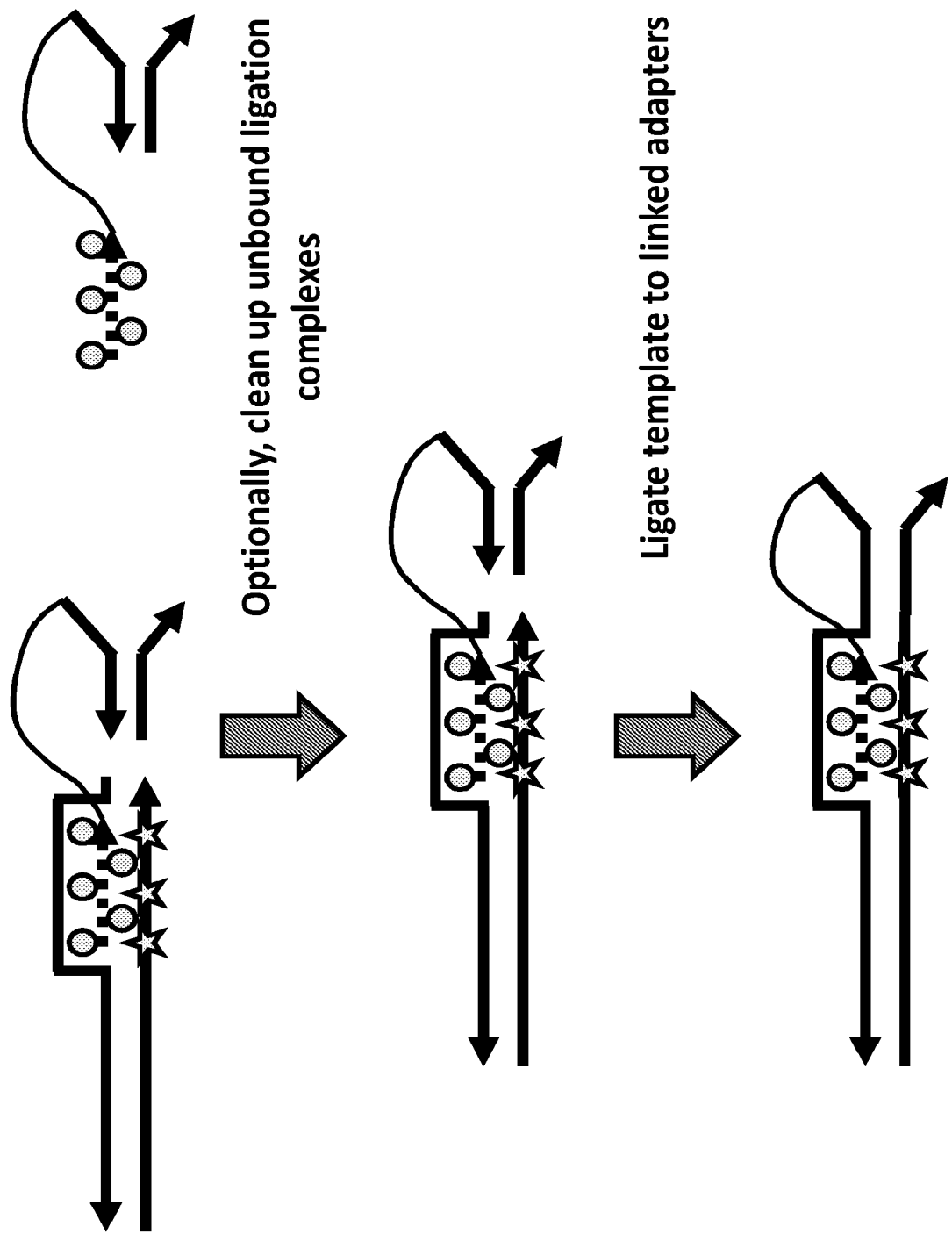
Figure 38C:
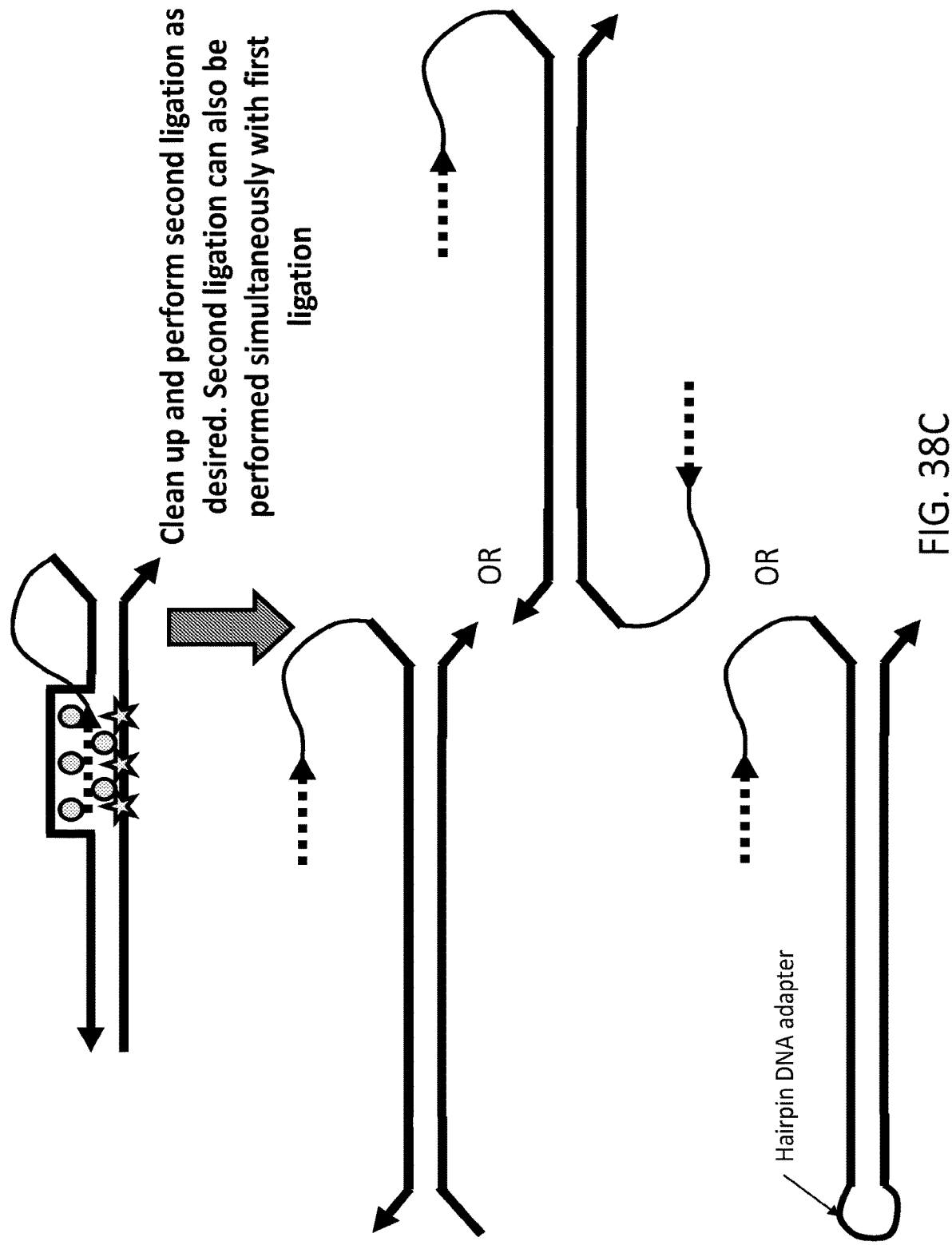
Figure 38D:
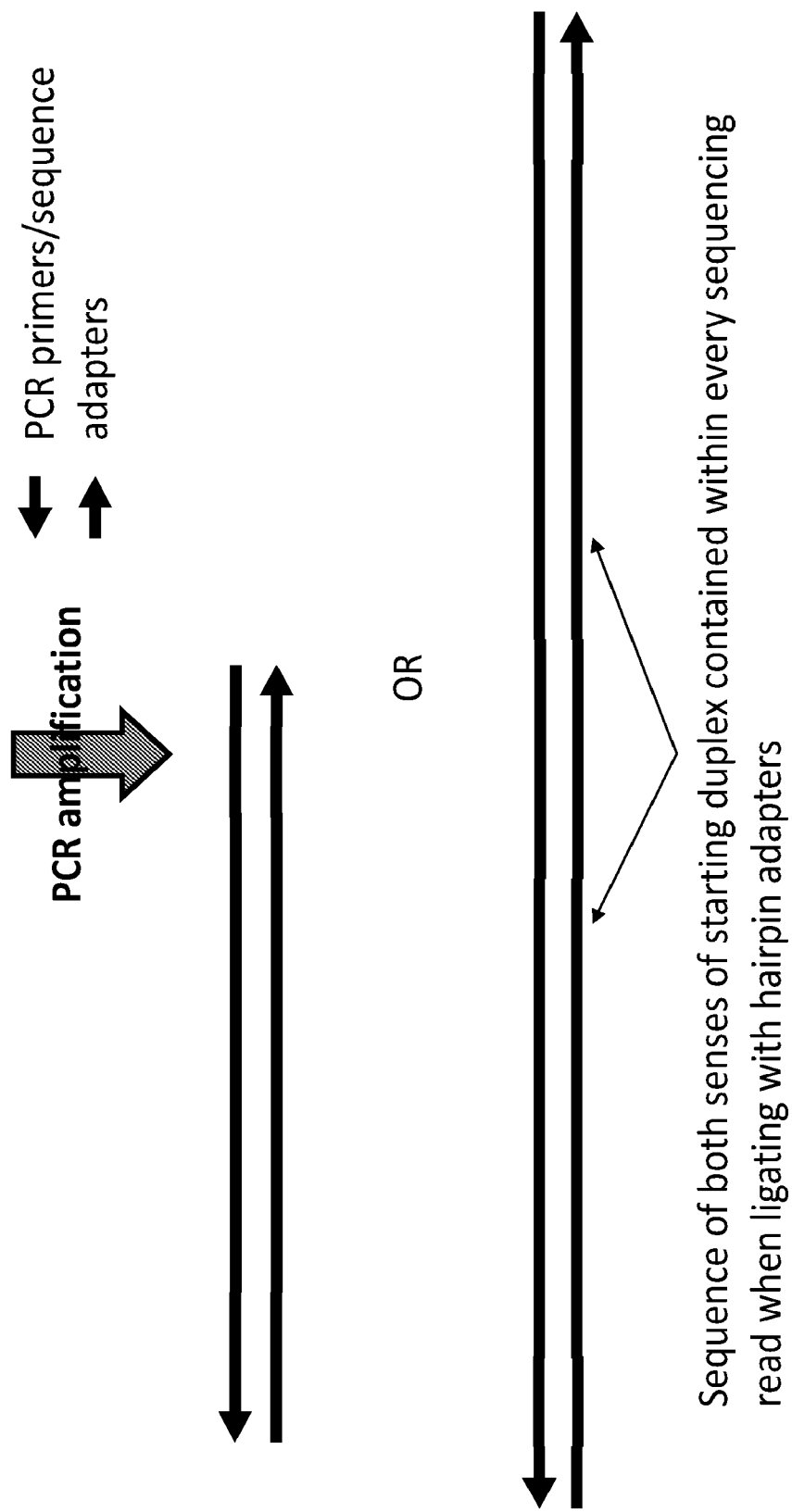

FIGS. 38A-D show an exemplary method of double stranded linked ligation. Double stranded linked ligation takes advantage of isothermal recombinase and single stranded binding proteins to generate strand invasion of dsDNA allowing primers or probes to pair with complementary sequences in the dsDNA with the single stranded binding proteins then binding to displaced DNA strands to prevent the primer or probe from being displaced. The process is similar to that used in Recombinase Polymerase Amplification (RPA) as described in Piepenburg, O., et al., 2006, DNA Detection Using Recombination Proteins, PLoS Biol 4(7): e204, incorporated herein by reference. Methods allow for ligation of specific DNA targets based on recognition sequence. Target capture can be integrated directly into ligation steps and makes for a simple targeted next generation sequencing workflow. The dsDNA methods described herein directs ligation to a desired end of the DNA, allowing different adapters to be added to each end. The methods allow for ligation of two different adapters to a single template with high efficiency. For example, a y adapter and a hairpin could be ligated (one option shown in FIG. 38C), so that duplex information could be integrated with every sequencing read (as shown in FIG. 38D).

As shown in FIG. 38A, ligation adapters may be incubated with ligation probes and recombinase to create a ligation complex. Ligation complexes can be made as separate parts and then linked together. For example, the ligation probe can be linked to the ligation adapter before incubating with recombinase. Linkers may comprise, for example, PEG, regular DNA bases, modified DNA bases, or inverted DNA bases. The linker may be non-extendable to prevent extension of the ligation probe. The ligation probe may be blocked to prevent extension. Linking can occur through click chemistry, biotin/streptavidin binding, or other DNA linking chemistries.

When the ligation complex is incubated with single stranded binding protein and a dsDNA genomic template comprising a target sequence complementary to the ligation probe, the ligation complex can bind the target sequence without requiring denaturing of the dsDNA as shown in FIG. 38B. Unbound ligation complexes may be optionally removed before the linked ligation adapters of the bound ligation complex are ligated to the dsDNA template. The dsDNA template with ligated adapters can then be cleaned up and additional ligations may be performed as shown in FIG. 38C. Additional ligations may be sequence specific, or standard, as sequence specific binding sites should be ligated with high efficiency, and ligation will only occur at unligated ends. Second ligation adapters can be the same or different from the first. Additionally, ligation of adapters to each end of a target can also happen in a single step. Ligation can also be multiplexed to cover desired target regions. If increased target specificity is desired, target capture, such as linked target capture, can be performed after ligation.

After adapter ligation to the target dsDNA, primers corresponding to sequences in the adapters (e.g., universal primers) may be used to amplify the target sequence for NGS using PCR amplification. Where a hairpin adapter has been ligated on one end of the dsDNA, duplex information can be obtained with each sequencing read as shown in FIG. 38D. In high mass samples, PCR may not be required allowing for PCR-free targeted ligation.

Linked adapters allow for ligation based on sequence recognition for double stranded or single stranded DNA targets. They further allow for targeting of a single sense of DNA at a time. The linked adapters described herein allow for ligation to be directed to a desired end of the DNA. Linked adapters may find application in simple targeted sequencing and barcoding workflows, fusion detection, targeted PCR-free library preparation, and droplet ligation and amplification.

Figure 31:
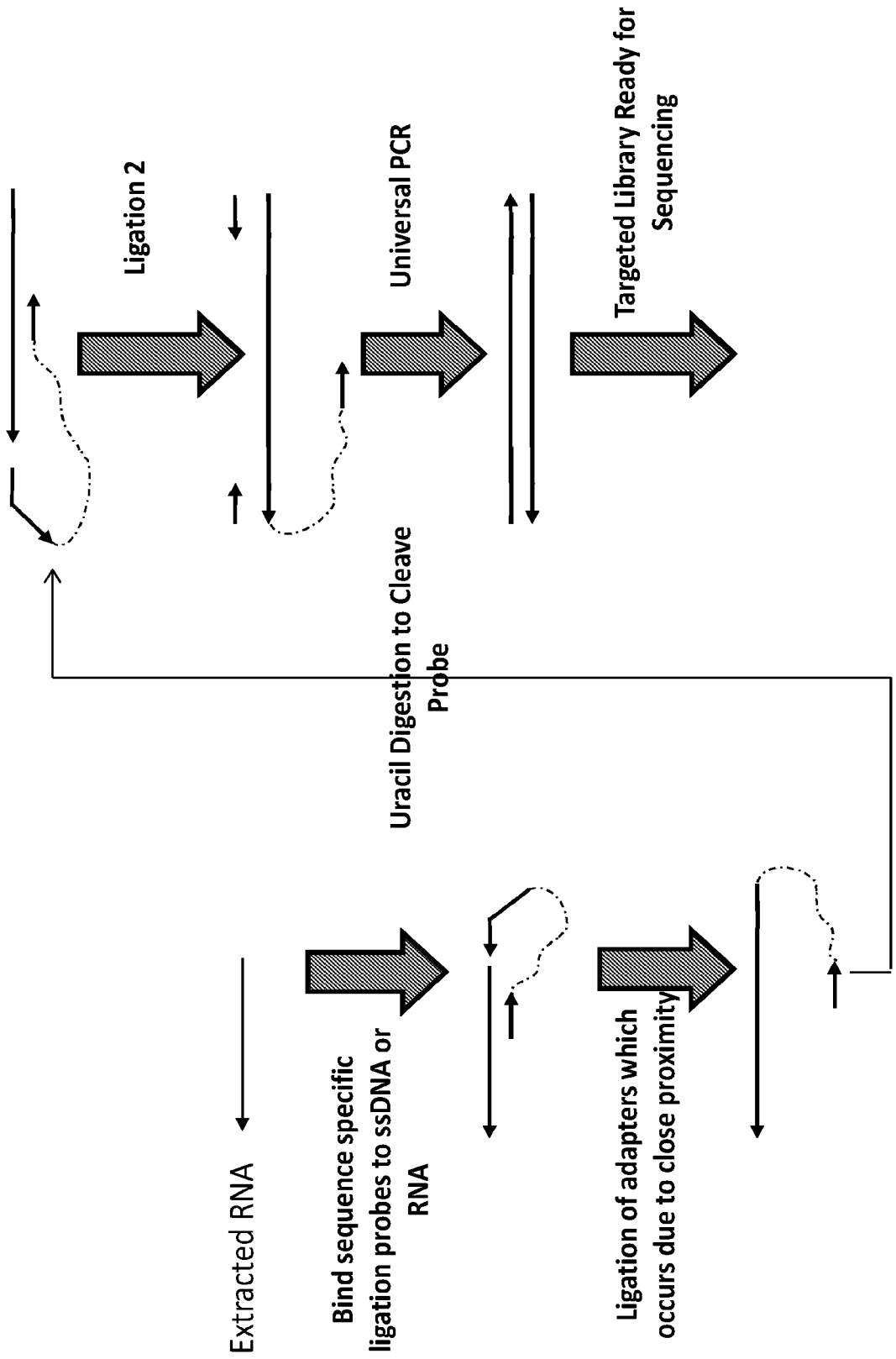
FIG. 31 shows linked ligation of adapters to fusion nucleic acids.

FIG. 31 shows application of linked adapters to selectively capture and amplify fusion nucleic acids for fusion detection. Fusion genes result from genomic rearrangements, such as deletions, amplifications and translocations. Such rearrangements can also frequently be observed in cancer and have been postulated as driving event in cancer development. Accordingly, characterizing these fusion genes can provide important information for personalized cancer diagnosis and treatment.

As shown in FIG. 31, an adapter is linked to a sequence specific probe complementary to a portion of the fusion nucleic acid (ssDNA or RNA) that is known. The probe binds the target sequence, allowing the adapter to ligate to the end of the target sequence. The linker may be cleavable, for example using a uracil digestion, and may be cleaved at this stage. A second adapter linked to a probe complementary to the same or a different portion of the known part of the fusion nucleic acid can then be introduced allowing the probe to bind the target nucleic acid and bring the linked adapter into close proximity to ligate onto the other end of the fusion even though the sequence is unknown. The adapter ligated template may then be amplified using universal primers and PCR to create a library for sequencing. This is useful in identifying and characterizing fusions where potentially only one side of the break point is known. The described method is faster and cheaper than traditional target capture and works better with RNA.

Figure 32A:
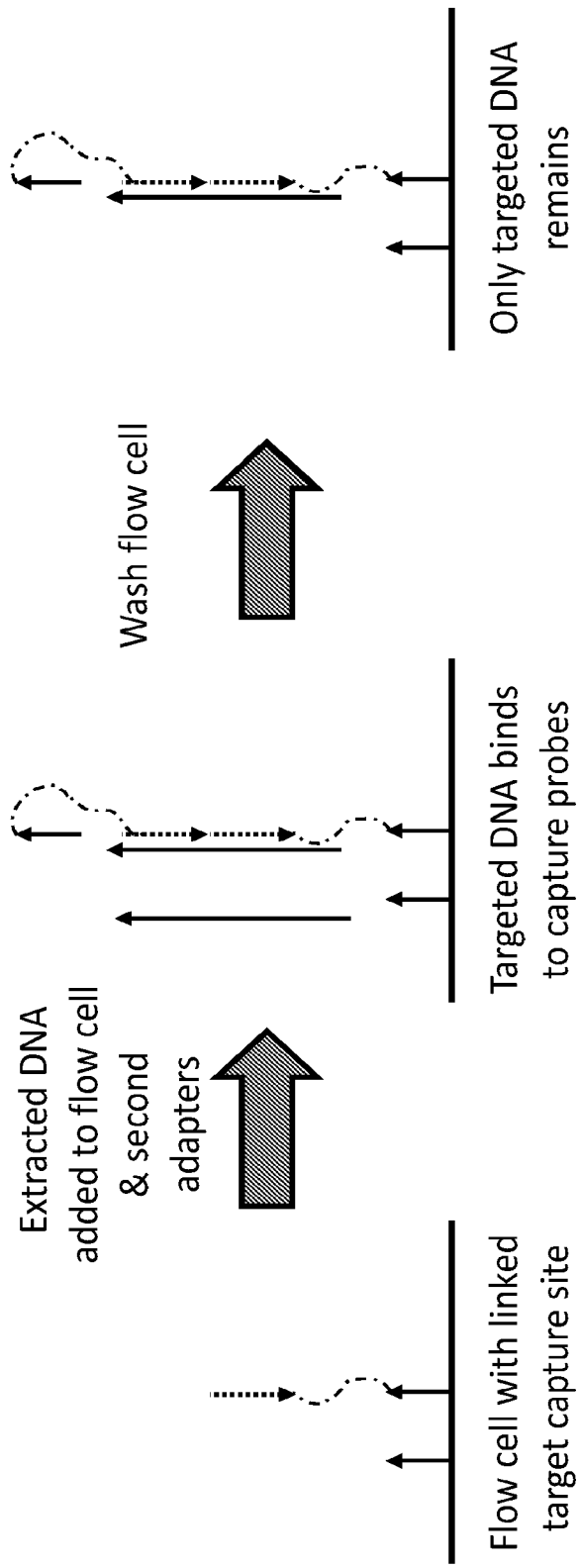
FIGS. 32A and 32B illustrate steps of a linked ligation surface capture technique according to certain embodiments.
Figure 32B:
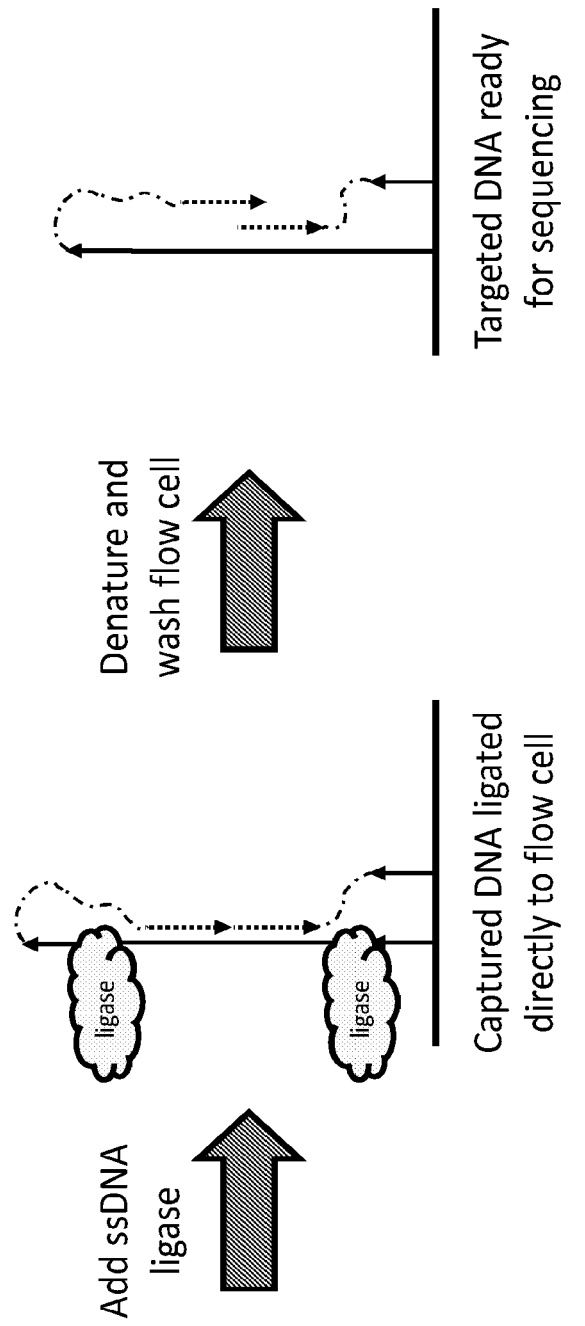

Linked ligation techniques may be used for surface capture as well to prepare flow cells for sequencing analysis. These techniques allow for capturing of target molecules based on sequence followed by ligation to the surface of the flow cell or other solid support. FIGS. 32A and 32B illustrate such a method. A flow cell is provided having an adapter bound to its surface in close proximity to surface bound and/or linked target specific probe complementary to a portion of the target template sequence. Additional free floating linked adapter/probe molecules are added to the flow cell along with a sample including strands of the target DNA. The targeted DNA binds to the capture probe on the flow cell and the free floating linked adapter/probe molecule. Unbound DNA and contaminants can then be washed away from the flow cell leaving just the target or targeted DNA. ssDNA ligase can then be added and, due to the close proximity of the surface bound adapter and the free floating probe linked adapter, the two adapters will ligate to the ends of the target DNA leaving a flow cell surface bound target DNA with sequencing adapters that is ready for flow cell sequencing after denaturing the probes and washing. Workflows are simplified by combining the ligation, target capture, and flow cell binding steps into one. A whole fragment can be sequenced as capture probes do not block sequencing. These methods can be used with single molecule sequencers such as those available from Direct Genomics (Shenzhen, China) or NanoString technologies (Seattle, Washington).

Figure 33A:
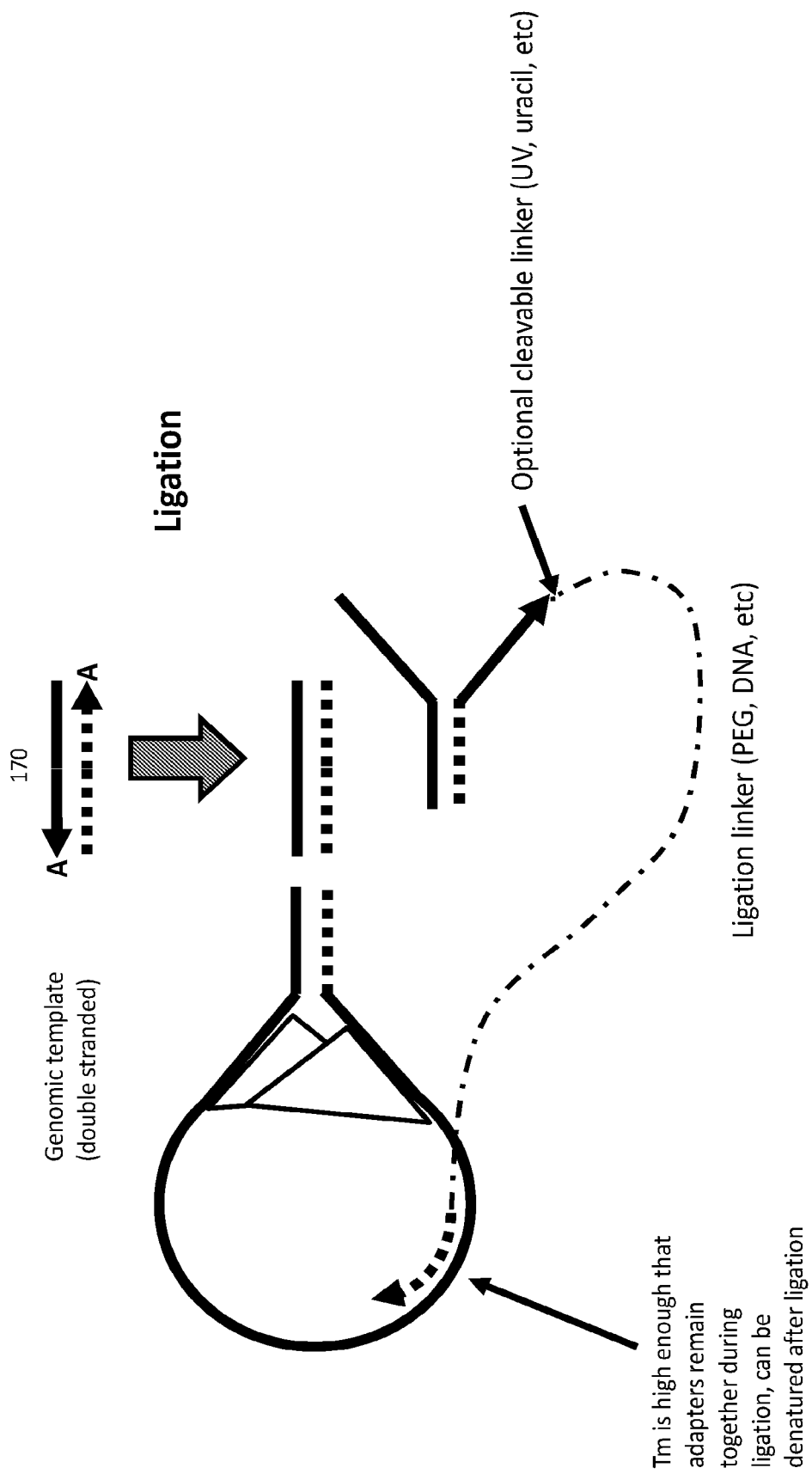
FIGS. 33A-33C illustrate linked adapter ligation according to certain embodiments.
Figure 33B:
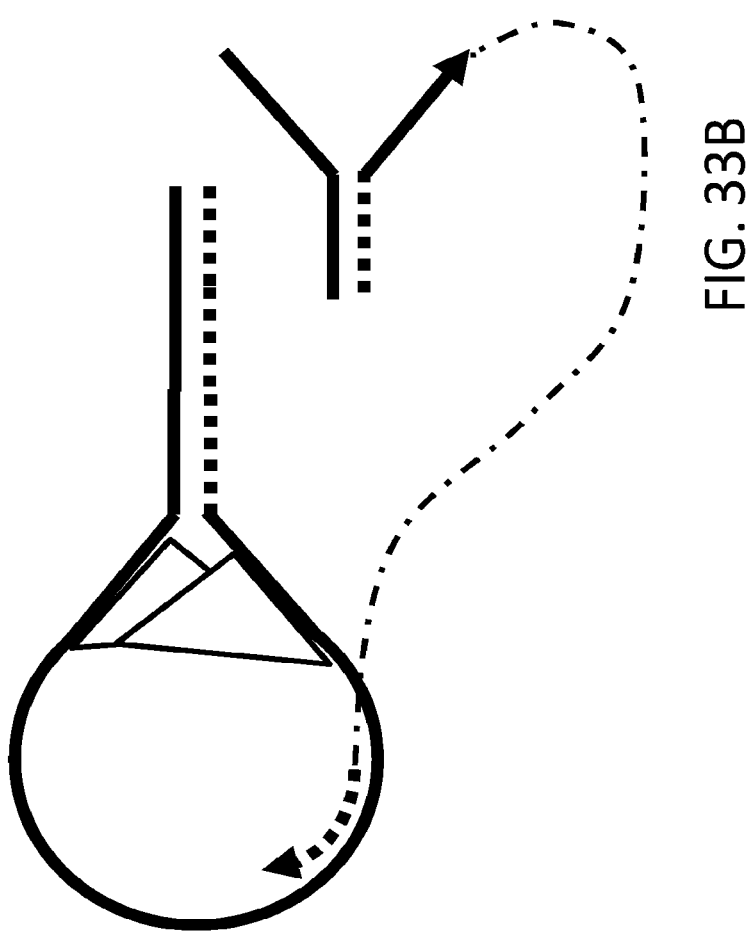
Figure 33C:
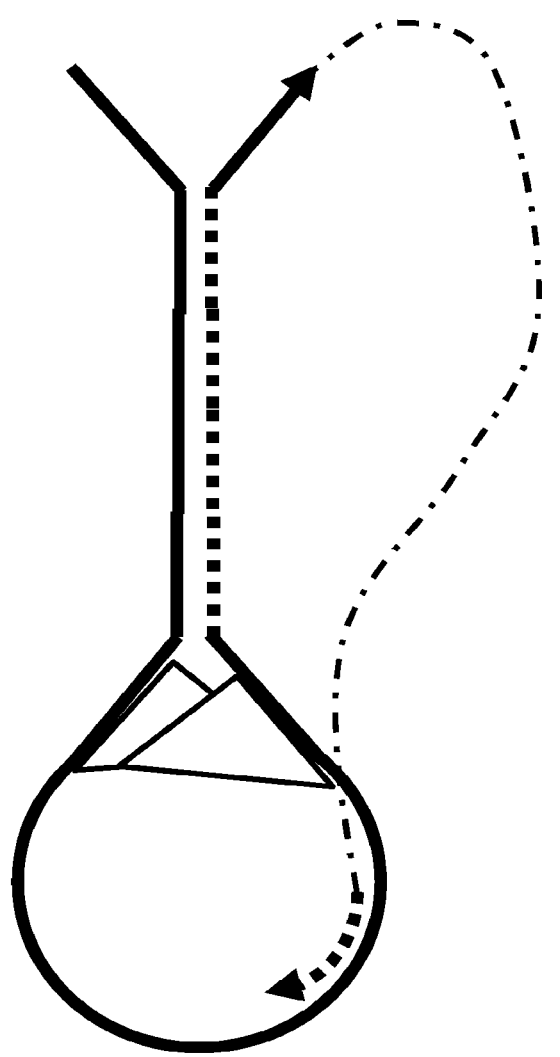

In certain embodiments, two adapters may be linked together to increase ligation efficiency and to help ensure that two different adapters are ligated to a single DNA molecule (as opposed to a DNA molecule with two of the same adapters ligated). FIGS. 33A-33C illustrate a method of ligating linked adapters to a DNA molecule. A double stranded genomic template is provided and exposed to two double stranded adapters that are linked together by, for example, PEG, nucleic acids, or other means. The linker may optionally be cleavable. The adapters may be joined by bound complementary sequences having a melting temperature ($T_m$) that is high enough that the adapters remain linked during ligation but can be denatured after ligation to separate the link. Once one adapter has ligated to the genomic template, the likelihood of the second, linked adapter binding the other end of the template is very high due to its close proximity as shown in FIG. 33B. As shown in FIG. 33C, the second adapter is ligated, ensuring that two different adapters ligate to the same double stranded DNA molecule. The ligation linker can be optionally cleaved at this point for subsequent PCR amplification using, for example, universal primers corresponding to primer sites included in the ligated adapters.

Figure 12:
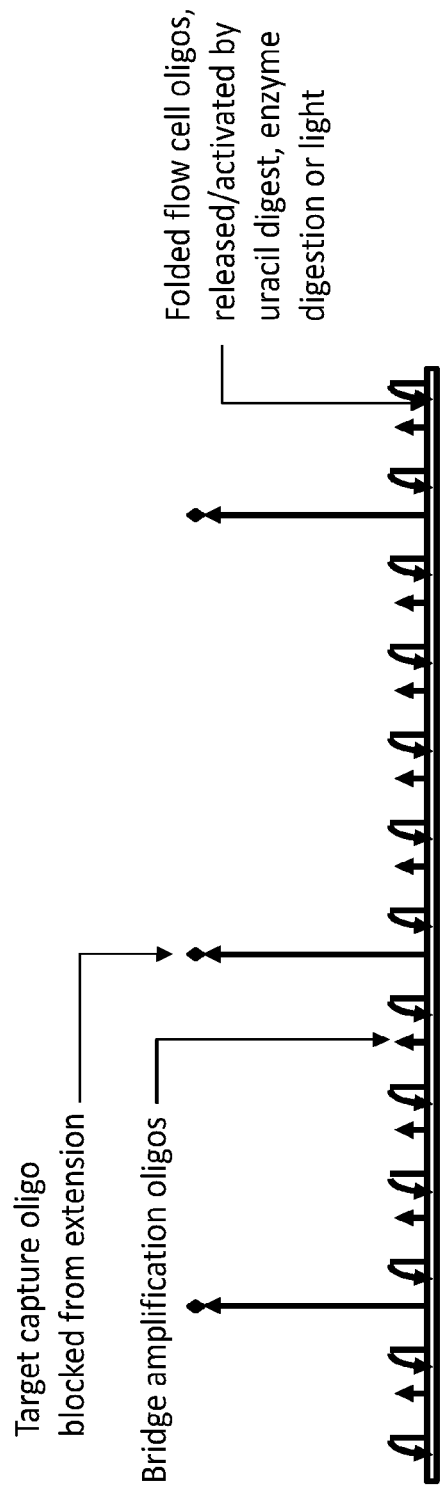
FIG. 12 illustrates flow cell based target capture methods for duplex molecules

For direct loading embodiments as well as other applications where the yield of flow cell loading and target capture yield are important, it may be beneficial to combine flow cell loading with targeted sequencing, to minimize loss. Such a combination additionally simplifies the workflow by eliminating an extra step. While methods exist for target capture on the flow cell, they suffer from at least two downsides. First, they are not able to sequence the region that is captured on the flow cell. For short fragments such as cell free DNA, this can amount to a large loss of signal. Secondly, they are unable to capture linked duplex molecules, as described in the invention, for sequencing. Accordingly, methods of the invention include flow cell based target capture of duplex molecules. According to methods of the invention, the flow cell contains one sense of oligonucleotides (oligos) having target regions, while the other sense are hair-pinned and not immediately available for binding. See FIG. 12. After one sense of linked molecules is captured on the flow cell, the other flow cell oligos are activated to capture the other sense of the linked fragments (e.g., using a uracil digest, enzyme digestion, or light). The template may then be extended and cluster generation may continue as normal. In certain embodiments the one set of oligos may be complementary to the sense or antisense strand of the duplex nucleic acid while the another set is complementary to a universal adapter that has been attached to both the sense and antisense strands and the universal adapter oligos may be hair-pinned to prevent binding in an initial exposure step.

Figure 13A:
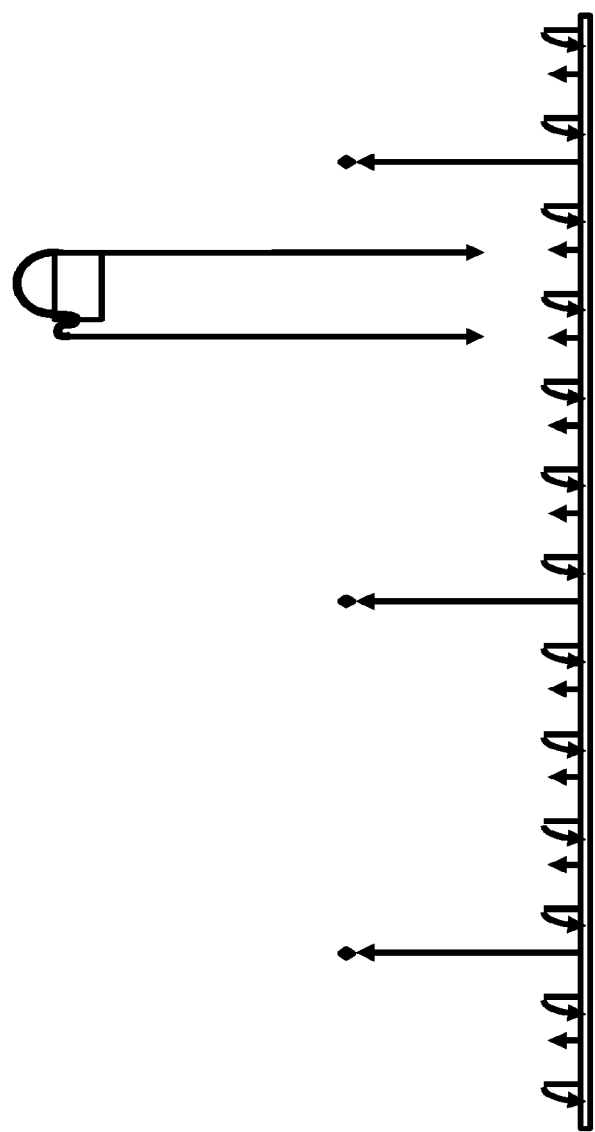
FIGS. 13A-13E depict steps in an exemplary flow cell based target capture and sequencing method for duplex molecules.
Figure 13B:
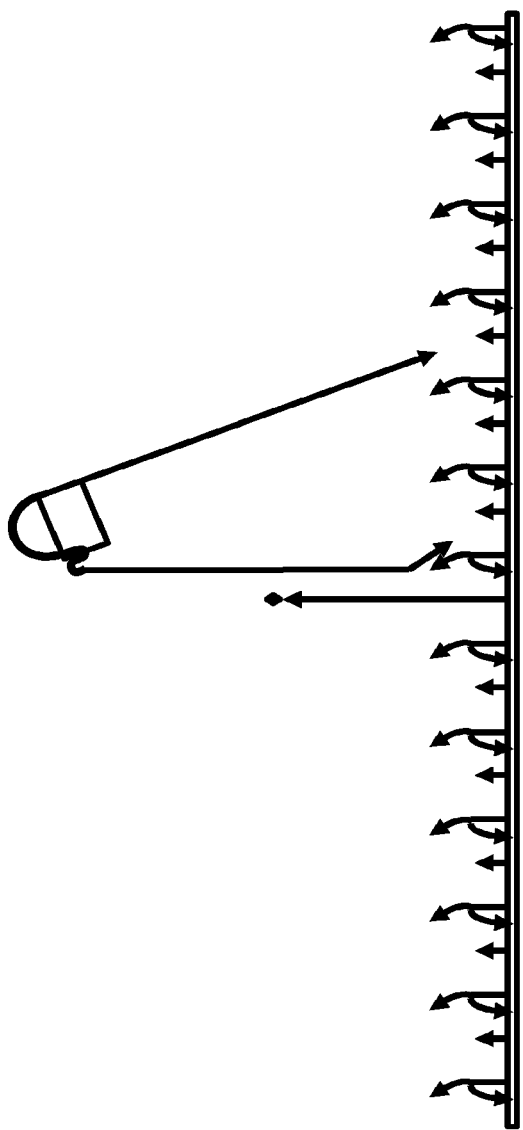
Figure 13C:
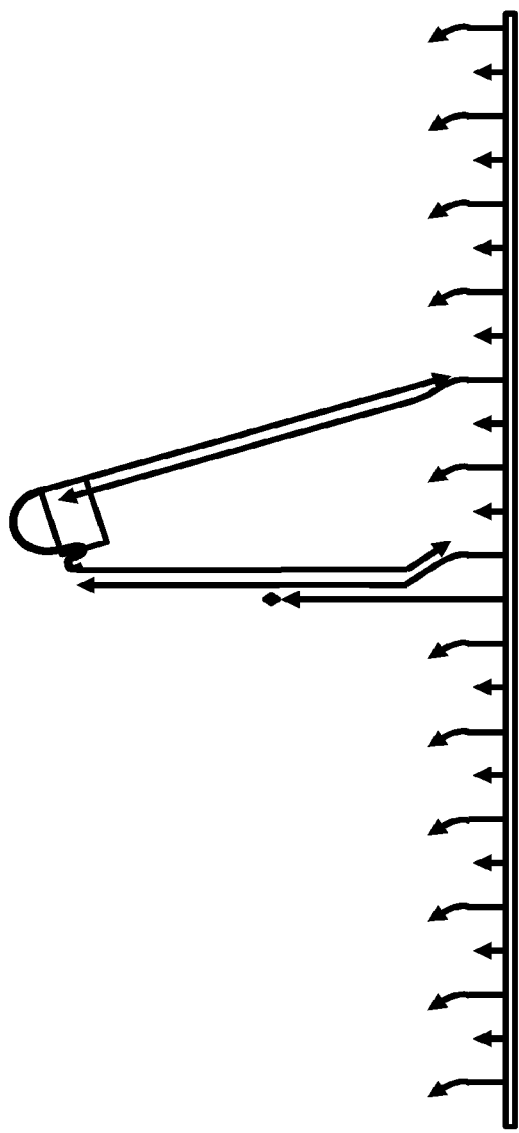
Figure 13D:
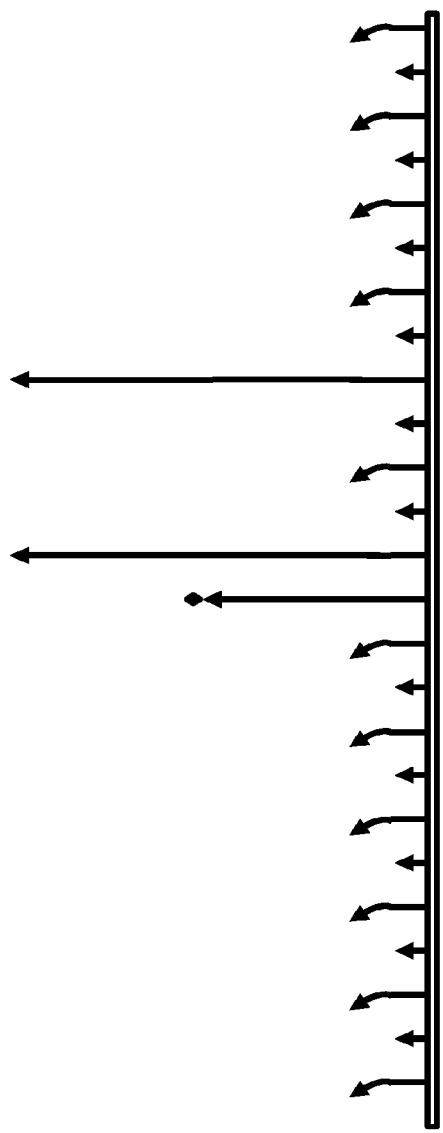
Figure 13E:
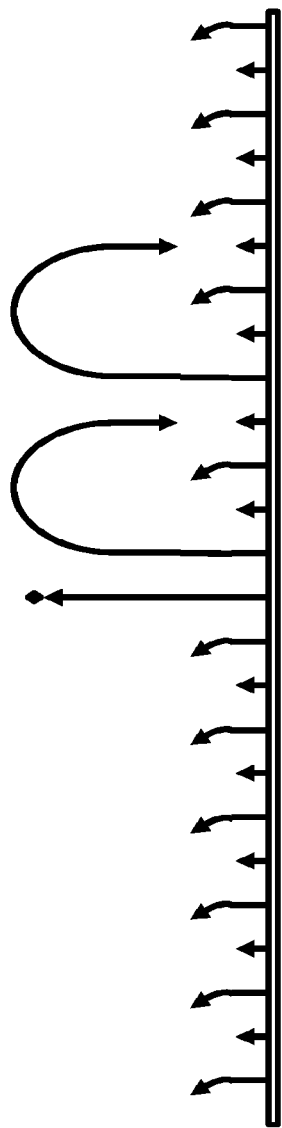

FIGS. 13A-E illustrate steps of an exemplary method for flow cell based target capture of duplex molecules. FIG. 13A shows an exemplary target capture step where a linked molecule is loaded onto a flow cell, either directly or by conventional methods. FIG. 13B shows an exemplary step of binding the template to the flow cell where the linked molecule binds to a complementary capture region, and the other sense of flow cell oligos are released to bind both free ends of linked fragment. FIG. 13C shows an exemplary strand displacement step where strand displacing polymerase is used to extend both fragment to create a doubly-seeded cluster. The linked template may then be denatured and removed from the flow cell as shown in FIG. 13D. Bridge amplification may then occur as normal, but with two molecules seeding the cluster as shown in FIG. 13E.

Direct loading techniques of the invention may be used in whole genome sequencing applications without flow cell target capture steps with one or two linking adapters. In targeted sequencing applications, after ligation with one or two linked adapters, a tube-based target capture technique may be used that is optimized for yield (e.g., having poor off-target rejection but high yield). The linked duplex template may then be directly loaded into the flow cell as described above with or without the target capture steps described in FIGS. 13A-E. In certain embodiments the intermediate tube-based target capture step may be omitted.

In certain embodiments, the linking molecule may be a streptavidin molecule and the fragments to be linked may comprise biotinylated nucleic acid. In embodiments where linked primers are used to create the linked nucleic acid fragments through amplification, the primers may be biotinylated and joined together on a streptavidin molecule. For example, 4 fragments may be joined together on a tetramer streptavidin. More than four molecules could be joined through the formation of concatemers, for example. In certain methods of the invention, two or more nucleic acid fragments may be linked through click chemistry reactions. See Kolb, et al., Click Chemistry: Diverse Chemical Function from a Few Good Reactions, Angew Chem Int Ed Engl. 2001 Jun. 1; 40(11):2004-2021, incorporated herein by reference.

Linking molecules, for example and of several known nanoparticles, may link large numbers of fragments including hundreds or thousands of fragments in a single linked molecule. One example of a linking nanoparticle may be polyvalent DNA gold nanoparticles comprising colloidal gold modified with thiol capped synthetic DNA sequences on their surface. See, Mirkin, et al., 1996, A DNA-based method for rationally assembling nanoparticles into macroscopic materials, Nature, 382:607-609, incorporated herein by reference. The surface DNA sequences may be complimentary to the desired template molecule sequences or may comprise universal primers.

The linking molecule may also serve to separate the nucleic acid fragments. In preferred embodiments, the fragments are oriented to prevent binding there between. With the linker creating spatial separation and orientation of the fragments controlled, collapsing or binding between the fragments can be avoided and prevented.

In some embodiments the linkers may be polyethylene glycol (PEG) or a modified PEG. A modified PEG, such as DBCO-PEG$_4$, or PEG-11 may be used to join the two adapters or nucleic acids. In another example, N-hydroxysuccinimide (NETS) modified PEG is used to join the two adapters. See Schlingman, et al., Colloids and Surfaces B: Biointerfaces 83 (2011) 91-95. Any oligonucleotide or other molecule may be used to join adapters or nucleic acids.

In some embodiments, aptamers are used to bind two adapters or nucleic acids. Aptamers can be designed to bind to various molecular targets, such as primers or nucleic acids. Aptamers may be designed or selected by the SELEX (systematic evolution of ligands by exponential enrichment) method. Aptamers are nucleic acid macromolecules that specifically bind to target molecules. Like all nucleic acids, a particular nucleic acid ligand, i.e., an aptamer, may be described by a linear sequence of nucleotides (A, U, T, C and G), typically 15-40 nucleotides long. In some preferred embodiments, the aptamers may include inverted bases or modified bases. In some embodiments, aptamers or modified apatmers, include at least one inverted base or modified base.

It should be appreciated that the linker may be composed of inverted bases, or comprise at least one inverted base. Inverted bases or modified bases may be acquired through any commercial entity. Inverted bases or modified bases are developed and commercially available. Inverted bases or modified bases may be incorporated into other molecules. For example, 2-Aminopurine can be substituted in an oligonucleotide. 2-Aminopurine is a fluorescent base that is useful as a probe for monitoring the structure and dynamics of DNA. 2,6-Diaminopurine (2-Amino-dA) is a modified base can form three hydrogen bonds when base-paired with dT and can increase the Tm of short oligos. 5-Bromo-deoxyuridine is a photoreactive halogenated base that can be incorporated into oligonucleotides to crosslink them to DNA, RNA or proteins with exposure to UV light. Other examples of inverted bases or modified bases include deoxyUridine (dU), inverted dT, dideoxycytidine (ddC), 5-methyl deoxyCytidine, or 2'-deoxyInosine (dI). It should be appreciated that any inverted or modified based can be used in linking template nucleic acids.

In preferred embodiments, the linker comprises a molecule for joining two primers or two nucleic acid fragments. The linker may be a single molecule, or a plurality of molecules. The linker may comprise a few inverted bases or modified bases, or entirely inverted bases or modified bases. The linker may comprise a both Watson-Crick bases and inverted or modified bases.

It should be appreciated that any spacer molecule or linking molecule may be used in the present invention. In some embodiments, the linker or spacer molecule may be a lipid or an oligosaccharide, or an oligosaccharide and a lipid. See U.S. Pat. No. 5,122,450. In this example, the molecule is preferably a lipid molecule and, more preferably, a glyceride or phosphatide which possesses at least two hydrophobic polyalkylene chains.

The linker may be composed of any number of adapters, primers, and copies of fragments. A linker may include two identical arms, where each arm is composed of binding molecules, amplification primers, sequencing primers, adapters, and fragments. A linker may link together any number of arms, such as three or four arms. It should be appreciated that in some aspects of the invention, nucleic acid templates are linked by a spacer molecule. The linker in the present invention may be any molecule or method to join two fragments or primers. In some embodiments, polyethylene glycol or a modified PEG such as DBCO-PEG$_4$ or PEG-11 is used. In some embodiments the linker is a lipid or a hydrocarbon. In some embodiments a protein may join the adapters or the nucleic acids. In some embodiments, an oligosaccharide links the primers or nucleic acids. In some embodiments, aptamers link the primers or nucleic acids. When the fragments are linked, the copies are oriented to be in phase so to prevent binding there between.

In certain embodiments, a linker may be an antibody. The antibody may be a monomer, a dimer or a pentamer. It should be appreciated that any antibody for joining two primers or nucleic acids may be used. For example, it is known in the art that nucleoside can be made immunogenic by coupling to proteins. See Void, B S (1979), Nucl Acids Res 7, 193-204. In addition, antibodies may be prepared to bind to modified nucleic acids. See Biochemical Education, Vol. 12, Issue 3.

The linker may stay attached to the complex during amplification. In some embodiments, the linker is removed prior to amplification. In some embodiments, a linker is attached to a binding molecule, and the binding molecule is then attached to an amplification primer. When the linker is removed, the binding molecule or binding primer is exposed. The exposed binding molecule also attaches to a solid support and an arch is formed. The linker may be removed by any known method in the art, including washing with a solvent, applying heat, altering pH, washing with a detergent or surfactant, etc.

Methods of the invention provide for nucleic acids to be linked together with a linker molecule. In samples with low genetic material, nucleic acids can be linked together in order to ensure that the duplex fragments amplified simultaneously or sequentially. Samples such as prenatal samples have low genetic content and amplifying duplex fragments increases the detectable content. This method reduces the signal to noise ratio, improving the detection of the target sequence.

Methods of the invention utilize amplification to amplify a target nucleic acid, such as a fragment, to a detectable level. It should be appreciated that any known amplification technique can be used in the present invention. Further, the amplified segments created by an amplification process may be themselves, efficient templates for subsequent amplifications.

Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, ligase chain reaction (Barany F. (1991) PNAS 88:189-193; Barany F. (1991) PCR Methods and Applications 1:5-16), ligase detection reaction (Barany F. (1991) PNAS 88:189-193), transcription based amplification system, nucleic acid sequence-based amplification, rolling circle amplification, and hyper-branched rolling circle amplification.

In some embodiments, multiple displacement amplification (MDA), a non-PCR based DNA amplification technique, rapidly amplifies minute amounts of DNA samples for genomic analysis. The reaction starts by annealing random hexamer primers to the template: DNA synthesis is carried out by a high fidelity enzyme at a constant temperature. However, it should be appreciated that any amplification method may be used with the current invention.

In certain embodiments of the invention, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence.

In some aspects of the invention, PCR primers are joined by a linker molecule and through the PCR process, copies of both strands of a duplex fragment are linked to the primers. In other embodiments, adapters are added to the primers or copies of the fragments. The resulting complex includes, generally, one sense and one antisense strand of a duplex fragment directly or indirectly joined by a linking molecule. It should be appreciated that one or both of the linked strand copies may include an error. However, there is a low probability that each fragment will have a matching error at the exact same base. Disagreement between the two fragments at a base would indicate an error as opposed to a true variant. The base could then be identified as an unknown, just from the raw sequencing data.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. The simplest equation for determining the melting temperature of primers smaller than 25 base pairs is the Wallace Rule ($Td=2(A+T)+4(G+C)$). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Oligo Design, available from Invitrogen Corp.

In some embodiments, to effect amplification, a mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one cycle; there can be numerous cycles) to obtain a high concentration of an amplified segment of a desired target sequence. The length of the amplified segment of the desired target sequence is determined by relative positions of the primers with respect to each other, and therefore, this length is a controllable parameter.

In some embodiments, to create complexes of the invention, primers are linked by a linking molecule or a spacer molecule to create two linked copies of the fragment. In other embodiments, two fragments are linked together following at least one PCR step. It should be appreciated that PCR can be applied to fragments before or after the fragments are joined via a linking molecule. In some embodiments, when the fragments are joined, PCR can be implemented on the joined fragments. In some embodiments, the linked copies undergo amplification. The amplification step includes linked primers. The result is that after a cycle of PCR, linked complexes comprising copies of the fragments are produced.

With PCR, it is possible to amplify a single copy of a specific target sequence in genomic DNA to a level that can be detected by several different methodologies (e.g., staining, hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences can be used to obtain segments of DNA (e.g., genes) for insertion into recombinant vectors.

Other amplification methods and strategies can also be utilized in the present invention. For example, another approach would be to combine PCR and the ligase chain reaction (LCR). Since PCR amplifies faster than LCR and requires fewer copies of target DNA to initiate, PCR can be used as first step followed by LCR. The amplified product could then be used in a LCR or ligase detection reaction (LDR) in an allele-specific manner that would indicate if a mutation was present. Another approach is to use LCR or LDR for both amplification and allele-specific discrimination. The later reaction is advantageous in that it results in linear amplification. Thus the amount of amplified product is a reflection of the amount of target DNA in the original specimen and therefore permits quantitation.

LCR utilizes pairs of adjacent oligonucleotides which are complementary to the entire length of the target sequence (Barany F. (1991) PNAS 88:189-193; Barany F. (1991) PCR Methods and Applications 1:5-16). If the target sequence is perfectly complementary to the primers at the junction of these sequences, a DNA ligase will link the adjacent 3' and 5' terminal nucleotides forming a combined sequence. If a thermostable DNA ligase is used with thermal cycling, the combined sequence will be sequentially amplified. A single base mismatch at the junction of the oligonucleotides will preclude ligation and amplification. Thus, the process is allele-specific. Another set of oligonucleotides with 3' nucleotides specific for the mutant would be used in another reaction to identify the mutant allele. A series of standard conditions could be used to detect all possible mutations at any known site. LCR typically utilizes both strands of genomic DNA as targets for oligonucleotide hybridization with four primers, and the product is increased exponentially by repeated thermal cycling.

Amplification or sequencing adapters or barcodes, or a combination thereof, may be attached to the fragmented nucleic acid. Such molecules may be commercially obtained, such as from Integrated DNA Technologies (Coralville, IA). In certain embodiments, such sequences are attached to the template nucleic acid molecule with an enzyme such as a ligase. Suitable ligases include T4 DNA ligase and T4 RNA ligase, available commercially from New England Biolabs (Ipswich, MA). The ligation may be blunt ended or via use of complementary overhanging ends.

In certain embodiments, following fragmentation, the ends of the fragments may be repaired, trimmed (e.g. using an exonuclease), or filled (e.g., using a polymerase and dNTPs) to form blunt ends. In some embodiments, end repair is performed to generate blunt end 5' phosphorylated nucleic acid ends using commercial kits, such as those available from Epicentre Biotechnologies (Madison, WI).

Upon generating blunt ends, the ends may be treated with a polymerase and dATP to form a template independent addition to the 3'-end and the 5'-end of the fragments, thus producing a single A overhanging. This single A can guide ligation of fragments with a single T overhanging from the 5'-end in a method referred to as T-A cloning. Alternatively, because the possible combination of overhangs left by the restriction enzymes are known after a restriction digestion, the ends may be left as-is, i.e., ragged ends. In certain embodiments double stranded oligonucleotides with complementary overhanging ends are used.

In certain embodiments, one or more bar code is attached to each, any, or all of the fragments. A bar code sequence generally includes certain features that make the sequence useful in sequencing reactions. The bar code sequences are designed such that each sequence is correlated to a particular portion of nucleic acid, allowing sequence reads to be correlated back to the portion from which they came. Methods of designing sets of bar code sequences is shown for example in U.S. Pat. No. 6,235,475, the contents of which are incorporated by reference herein in their entirety. In certain embodiments, the bar code sequences are attached to the template nucleic acid molecule, e.g., with an enzyme. The enzyme may be a ligase or a polymerase, as discussed above. Attaching bar code sequences to nucleic acid templates is shown in U.S. Pub. 2008/0081330 and U.S. Pub. 2011/0301042, the content of each of which is incorporated by reference herein in its entirety. Methods for designing sets of bar code sequences and other methods for attaching bar code sequences are shown in U.S. Pat. Nos. 7,537,897; 6,138,077; 6,352,828; 5,636,400; 6,172,214; and 5,863,722, the content of each of which is incorporated by reference herein in its entirety. After any processing steps (e.g., obtaining, isolating, fragmenting, amplification, or barcoding), nucleic acid can be sequenced.

Exemplary methods for designing sets of barcode sequences and other methods for attaching barcode sequences are shown in U.S. Pat. Nos. 6,138,077; 6,352,828; 5,636,400; 6,172,214; 6,235,475; 7,393,665; 7,544,473; 5,846,719; 5,695,934; 5,604,097; 6,150,516; RE39,793; 7,537,897; 6172,218; and 5,863,722, the content of each of which is incorporated by reference herein in its entirety.

The barcode sequence generally includes certain features that make the sequence useful in sequencing reactions. For example the barcode sequences can be designed to have minimal or no homopolymer regions, i.e., 2 or more of the same base in a row such as AA or CCC, within the barcode sequence. The barcode sequences can also be designed so that they do not overlap the target region to be sequence or contain a sequence that is identical to the target.

The first and second barcode sequences are designed such that each pair of sequences is correlated to a particular sample, allowing samples to be distinguished and validated. Methods of designing sets of barcode sequences is shown for example in Brenner et al. (U.S. Pat. No. 6,235,475), the contents of which are incorporated by reference herein in their entirety. In certain embodiments, the barcode sequences range from about 2 nucleotides to about 50; and preferably from about 4 to about 20 nucleotides. Since the barcode sequence is sequenced along with the template nucleic acid or may be sequenced in a separate read, the oligonucleotide length should be of minimal length so as to permit the longest read from the template nucleic acid attached. Generally, the barcode sequences are spaced from the template nucleic acid molecule by at least one base.

Methods of the invention involve attaching the barcode sequences to the template nucleic acids. Template nucleic acids are able to be fragmented or sheared to desired length, e.g. generally from 100 to 500 bases or longer, using a variety of mechanical, chemical and/or enzymatic methods. DNA may be randomly sheared via sonication, exposed to a DNase or one or more restriction enzymes, a transposase, or nicking enzyme. RNA may be fragmented by brief exposure to an RNase, heat plus magnesium, or by shearing. The RNA may be converted to cDNA before or after fragmentation.

Barcode sequence is integrated with template using methods known in the art. Barcode sequence is integrated with template using, for example, a ligase, a polymerase, Topo cloning (e.g., Invitrogen's topoisomerase vector cloning system using a topoisomerase enzyme), or chemical ligation or conjugation. The ligase may be any enzyme capable of ligating an oligonucleotide (RNA or DNA) to the template nucleic acid molecule. Suitable ligases include T4 DNA ligase and T4 RNA ligase (such ligases are available commercially, from New England Biolabs). Methods for using ligases are well known in the art. The polymerase may be any enzyme capable of adding nucleotides to the 3' and the 5' terminus of template nucleic acid molecules. Barcode sequence can be incorporated via a PCR reaction as part of the PCR primer. Regardless of the incorporation of molecular barcodes or the location of the barcodes in the event that they are incorporated, sequencing adaptors can be attached to the nucleic acid product in a bi-directional way such that in the same sequencing run there will be sequencing reads from both the 5' and 3' end of the target sequence. In some cases it is advantage to use the location of the barcode on the 5' or 3' end of the target sequence to indicate the direction of the read. It is well known to one skilled in the art how to attach the sequencing adaptors using techniques such as PCR or ligation.

Figure 15:
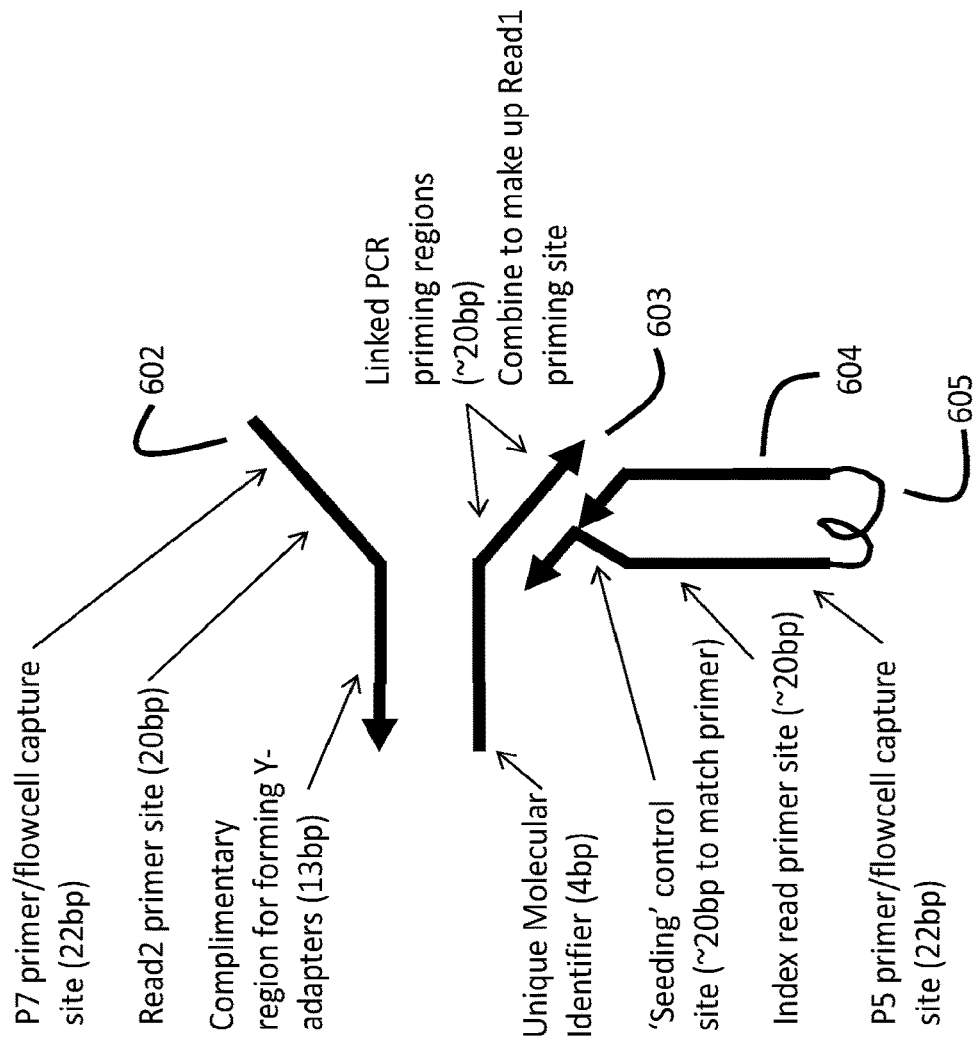
FIG. 15 shows examples of possible configurations of adapters and primers.

FIG. 15 shows examples of possible configurations of adapters and primers. As shown at 602, a P7 primer is attached to a Read2 primer site, which is attached to a complimentary region. At 603, a linked PCR priming region is attached to a unique molecular identifier. As shown at 604, a P5 primer is attached to an index read primer site, and a seeding control site.

In some embodiments, multiple copies of a fragment are joined together. It should be appreciated that any number of fragments can be joined together, whether 2, 3, 4, etc. The joined copies may be referred to as a unit. Several units may then be joined together with a linking molecule. It should be appreciated that any number of units may be joined by a linking molecule. This increases the information density within a complex. When the complex is attached to a solid support, the complex is amplified. The amplification products may be attached to the solid support. By joining multiple copies of the fragment to the complex and then amplifying the complexes, information density on a solid support increases.

In certain embodiments, the nucleic acids may be amplified by two or more joined primers. Any known method of amplification may be used in conjunction with the linked primers. In certain embodiments, digital PCR or emulsion PCR may be used to create two or more linked nucleic acid fragments for seeding sequencing clusters or for use in other sequencing methods. In a preferred embodiment, a template nucleic acid may be created by ligating adapters to a nucleic acid fragment of interest to be sequenced. Adapters may optionally include universal priming sites, one or more sequencing primer sites, and unique cluster identifiers to ensure that all sequencing reads in a given cluster originated from the same starting template. For example, adapters may be used with varying stem regions such as y1: CCTACTCGCTAC (SEQ ID No. 1), y2: ATGCGAGCCTCT (SEQ ID No. 2), y3: GCACCT-CATCCA (SEQ ID No. 3), and y4: TGCAGGATGGTG (SEQ ID No. 4). Adapter sequences may include a unique cluster identifier (UCI) which may comprise a series of random bases (e.g., 2, 3, 4, 5, or more) to distinguish between neighboring clusters on a sequencing flow cell. Adapter sequences may include a phosphorothioate-linked T in order to reduce 3' exonuclease digestion that might remove T overhang and reduce ligation efficiency. A 3' phosphate blocker is optional but not essential for digital PCR methods of the invention.

Once adapters have been ligated to the nucleic acid fragment to be sequenced, an emulsion or droplet can be created. The droplets may be aqueous droplets surrounded by an immiscible carrier fluid. Methods of forming such droplets and conducting PCR amplification within the droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), and Anderson et al. (U.S. Pat. No. 7,041,481 and which reissued as RE41,780).

In preferred embodiments, a single template nucleic acid molecule is added to a droplet in order to ensure that eventual clusters are seeded with only one template molecule and to prevent the formation of hybrid linked nucleic acid complexes containing different nucleic acid fragments. Various multiplex primers that may be gene specific are also added to the droplet along with linked primers. The linked primers may be two or more primers linked together according to any of the methods described herein. Linked primers may include, for example, universal priming sites corresponding to the universal priming sites in the ligated adapters as well as sequencing primer sites (e.g., different index priming sites to identify when more than one molecule has seeded a cluster). In certain embodiments, the linked primers may include gene specific primers targeting specific regions of interest to be sequenced such that the initial ligation step may be avoided and an unmodified nucleic acid fragment may be added directly to the droplet for linked-primer digital PCR amplification. According to certain methods of the invention, the ligated template may comprise a priming site corresponding to the priming site of the linked universal primers and gene specific multiplex primers are used to create linked copies of the target nucleic acid.

Complexes of the invention may be attached to various solid supports such as microbeads, beads, channel walls, microchips, etc.

Sequencing the joined fragments may be by any method known in the art. The present invention has applications in various sequencing platforms, including the genome sequencers from Roche/454 Life Sciences (Margulies et al. (2005) Nature, 437:376-380; U.S. Pat. Nos. 6,274,320; 6,258,568; 6,210,891), the SOLiD system from Life Technologies Applied Biosystems (Grand Island, NY), the HELISCOPE system from Helicos Biosciences (Cambridge, MA) (see, e.g., U.S. Pub. 2007/0070349), and the Ion sequencers from Life Technologies Ion Torrent, Ion Torrent Systems, Inc. (Guilford, CT).

In preferred embodiments, sequencing is by methods where each base is determined sequentially. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

It should be appreciated that the linker may also be attached to adapters, primers, or binding molecules. The linker can be attached to these species in any orientation or arrangement. The linking molecule may be directly attached to an adapter or primer and indirectly linked to the nucleic acid fragments. In some aspects of the invention, the linking molecule is removed before or after amplification. In some embodiments, the linking molecule remains on the complex. In some embodiments, the linking molecule is removed prior to sequencing, where in other embodiments the linking molecule remains on the complex during sequencing.

A sequencing technique that can be used in the methods of the provided invention includes, for example, Helicos True Single Molecule Sequencing (tSMS) (Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm'. The flow cell is then loaded into an instrument, e.g., HeliScope sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. With the present invention, the linked fragments can be identified in tandem. Further description of tSMS is shown for example in Lapidus et al. (U.S. Pat. No. 7,169,560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety.

Another example of a DNA sequencing technique that can be used in the methods of the provided invention is 454 sequencing (Roche) (Margulies, M et al. 2005, Nature, 437, 376-380). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. Using the methods of the present invention, joined fragments as described above are captured on the beads. The joined fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is Ion Torrent sequencing (U.S. patent application numbers 2009/0026082, 2009/0127589, 2010/0035252, 2010/0137143, 2010/0188073, 2010/0197507, 2010/0282617, 2010/0300559, 2010/0300895, 2010/0301398, and 2010/0304982), the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Using the methods of the present invention, the joined fragments are attached to the surface. Addition of one or more nucleotides releases a proton (H+), which signal detected and recorded in a sequencing instrument. The signal strength is proportional to the number of nucleotides incorporated.

The invention also encompasses methods of sequencing amplified nucleic acids generated by solid-phase amplification. Thus, the invention provides a method of nucleic acid sequencing comprising amplifying a pool of nucleic acid templates using solid-phase amplification and carrying out a nucleic acid sequencing reaction to determine the sequence of the whole or a part of at least one amplified nucleic acid strand produced in the solid-phase amplification reaction. The initiation point for the sequencing reaction may be provided by annealing of a sequencing primer to a product of a solid-phase amplification reaction. In this connection, one or both of the adaptors added during formation of the template library may include a nucleotide sequence which permits annealing of a sequencing primer to amplified products derived by whole genome or solid-phase amplification of the template library.

The products of solid-phase amplification reactions wherein both forward and reverse amplification primers are covalently immobilized on the solid surface are so-called bridged structures formed by annealing of pairs of immobilized polynucleotide strands and immobilized complementary strands, both strands being attached to the solid support at the 5' end. Arrays comprised of such bridged structures provide inefficient templates for typical nucleic acid sequencing techniques, since hybridization of a conventional sequencing primer to one of the immobilized strands is not favored compared to annealing of this strand to its immobilized complementary strand under standard conditions for hybridization.

In order to provide more suitable templates for nucleic acid sequencing, it may be advantageous to remove or displace substantially all or at least a portion of one of the immobilized strands in the bridged structure in order to generate a template which is at least partially single-stranded. The portion of the template which is single-stranded will thus be available for hybridization to a sequencing primer. The process of removing all or a portion of one immobilized strand in a 'bridged' double-stranded nucleic acid structure may be referred to herein as linearization, and is described in further detail in U.S. Pub. 2009/0118128, the contents of which are incorporated herein by reference in their entirety.

Bridged template structures may be linearized by cleavage of one or both strands with a restriction endonuclease or by cleavage of one strand with a nicking endonuclease. Other methods of cleavage can be used as an alternative to restriction enzymes or nicking enzymes, including inter alia chemical cleavage (e.g. cleavage of a diol linkage with periodate), cleavage of abasic sites by cleavage with endonuclease (for example 'USER', as supplied by NEB, part number M55055), or by exposure to heat or alkali, cleavage of ribonucleotides incorporated into amplification products otherwise comprised of deoxyribonucleotides, photochemical cleavage or cleavage of a peptide linker Following the cleavage step, regardless of the method used for cleavage, the product of the cleavage reaction may be subjected to denaturing conditions in order to remove the portion(s) of the cleaved strand(s) that are not attached to the solid support. Suitable denaturing conditions, for example sodium hydroxide solution, formamide solution or heat, will be apparent to the skilled reader with reference to standard molecular biology protocols (Sambrook et al., supra; Ausubel et al. supra). Denaturation results in the production of a sequencing template which is partially or substantially single-stranded. A sequencing reaction may then be initiated by hybridization of a sequencing primer to the single-stranded portion of the template. Thus, the invention encompasses methods wherein the nucleic acid sequencing reaction comprises hybridizing a sequencing primer to a single-stranded region of a linearized amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand.

Another example of a sequencing technology that can be used in the methods of the provided invention is Illumina sequencing. Illumina sequencing workflow is based on three steps: libraries are prepared from virtually any nucleic acid sample, amplified to produce clonal clusters and sequenced using massively parallel synthesis. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. Using the methods of the present invention, the joined fragments are attached to the flow cell channels and extended and bridge amplified. In some embodiments, the linker is removed prior to bridge amplification. In some embodiments, the linker remains attached to the fragments during amplification. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pat. Nos. 7,960,120; 7,835,871; 7,232,656; 7,598,035; 6,911,345; 6,833,246; 6,828,100; 6,306,597; 6,210,891; U.S. Pub. 2011/0009278; U.S. Pub. 2007/0114362; U.S. Pub. 2006/0292611; and U.S. Pub. 2006/0024681, each of which are incorporated by reference in their entirety.

Methods of the present invention can be incorporated into the Illumina sequencing platform (commercially available from Illumina, Inc, San Diego, CA). Using the present invention, libraries of linked complexes comprising copies of both strands of a duplex fragment are prepared and then attached to the solid support. The complexes are amplified to produce clonal clusters and then sequenced using massively parallel synthesis. In this method, each cluster is seeded with one fragment. With the present invention, both strands of a duplex fragment seed a cluster. During sequencing, if there is a lack of agreement at a particular base between the amplicons, the error is detected.

The Illumina Genome Analyzer (detector, commercially available by Illumina) is based on parallel, fluorescence-based readout of millions of immobilized sequences that are iteratively sequenced using reversible terminator chemistry. In one example, up to eight DNA libraries are hybridized to an eight-lane flow cell. In each of the lanes, single-stranded library molecules hybridize to complementary oligonucleotides that are covalently bound to the flow cell surface. The reverse strand of each library molecule is synthesized and the now covalently bound molecule is then further amplified in a process called bridge amplification. This generates clusters each containing more than 1,000 copies of the starting molecule. One strand is then selectively removed, free ends are subsequently blocked and a sequencing primer is annealed onto the adapter sequences of the cluster molecules.

Although the fluorescent imaging system is not sensitive enough to detect the signal from a single template molecule, the detector is sensitive to detect the signal from each cluster. In this example of the invention, the signals from numerous clusters are analyzed. Each cluster is expected to fluoresce at a value, for example, approximate to one of the four bases. If the cluster does not fluoresce at a value approximate to one of the four bases, then it is determined that an error exists at that locus.

After sequencing, images are analyzed and intensities extracted for each cluster. The Illumina base caller, Bustard, has to handle two effects of the four intensity values extracted for each cycle and cluster: first, a strong correlation of the A and C intensities as well as of the G and T intensities due to similar emission spectra of the fluorophores and limited separation by the filters used; and second, dependence of the signal for a specific cycle on the signal of the cycles before and after, known as phasing and pre-phasing, respectively. Phasing and pre-phasing are caused by incomplete removal of the 3' terminators and fluorophores, sequences in the cluster missing an incorporation cycle, as well as by the incorporation of nucleotides without effective 3' terminators. Phasing and pre-phasing cause the extracted intensities for a specific cycle to consist of the signal of the current cycle as well as noise from the preceding and following cycles.

Another example of a sequencing technology that can be used in the methods of the provided invention includes the single molecule, real-time (SMRT) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated. Using methods of the present invention, the process is repeated in tandem, with two fragments being analyzed.

Another example of a sequencing technique that can be used in the methods of the provided invention is nanopore sequencing (Soni G V and Meller A. (2007) Clin Chem 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence. Using methods of the present invention, two fragments are analyzed simultaneously or sequentially, reducing the chance of an error.

The present invention can be used with nanopore technology, such as single molecule nanopore-based sequencing by synthesis (Nano-SBS). This strategy can distinguish four bases by detecting 4 different sized tags released from 5'-phosphate-modified nucleotides. As each nucleotide is incorporated into the growing DNA strand during the polymerase reaction, its tag is released and enters a nanopore in release order. This produces a unique ionic current blockade signature due to the tag's distinct chemical structure, thereby determining DNA sequence electronically at single molecule level with single base resolution. Using the methods of the invention, both strands of a duplex fragment can be analyzed simultaneously or sequentially. See Kumar, et al. Scientific Reports, Article number 684, doi:10.1038/srep00684.

Functions described above such as sequence read analysis or assembly can be implemented using systems of the invention that include software, hardware, firmware, hard-wiring, or combinations of any of these.

One sequencing method which can be used in accordance with the invention relies on the use of modified nucleotides having removable 3' blocks, for example as described in W004018497, US 2007/0166705A1 and U.S. Pat. No. 7,057,026, the contents of which are incorporated herein by reference in their entirety. Once the modified nucleotide has been incorporated into the growing polynucleotide chain complementary to the region of the template being sequenced there is no free 3'-OH group available to direct further sequence extension and therefore the polymerase cannot add further nucleotides. Once the nature of the base incorporated into the growing chain has been determined, the 3' block may be removed to allow addition of the next successive nucleotide. By ordering the products derived using these modified nucleotides, it is possible to deduce the DNA sequence of the DNA template. Such reactions can be done in a single experiment if each of the modified nucleotides has a different label attached thereto, known to correspond to the particular base, to facilitate discrimination between the bases added during each incorporation step. Alternatively, a separate reaction may be carried out containing each of the modified nucleotides separately.

Embodiments of the invention may incorporate modified nucleotides. The modified nucleotides may be labeled (e.g., fluorescent label) for detection. Each nucleotide type may thus carry a different fluorescent label, for example, as described in U.S. Pub. 2010/0009353, the contents of which are incorporated herein by reference in their entirety. The detectable label need not, however, be a fluorescent label. Any label can be used which allows the detection of an incorporated nucleotide. One method for detecting fluorescently labeled nucleotides comprises using laser light of a wavelength specific for the labeled nucleotides, or the use of other suitable sources of illumination. The fluorescence from the label on the nucleotide may be detected by a CCD camera or other suitable detection means. Suitable instrumentation for recording images of clustered arrays is described in WO07123744 and U.S. Pub. 2010/0111768, the contents of which are incorporated herein by reference in their entirety.

Figure 18:
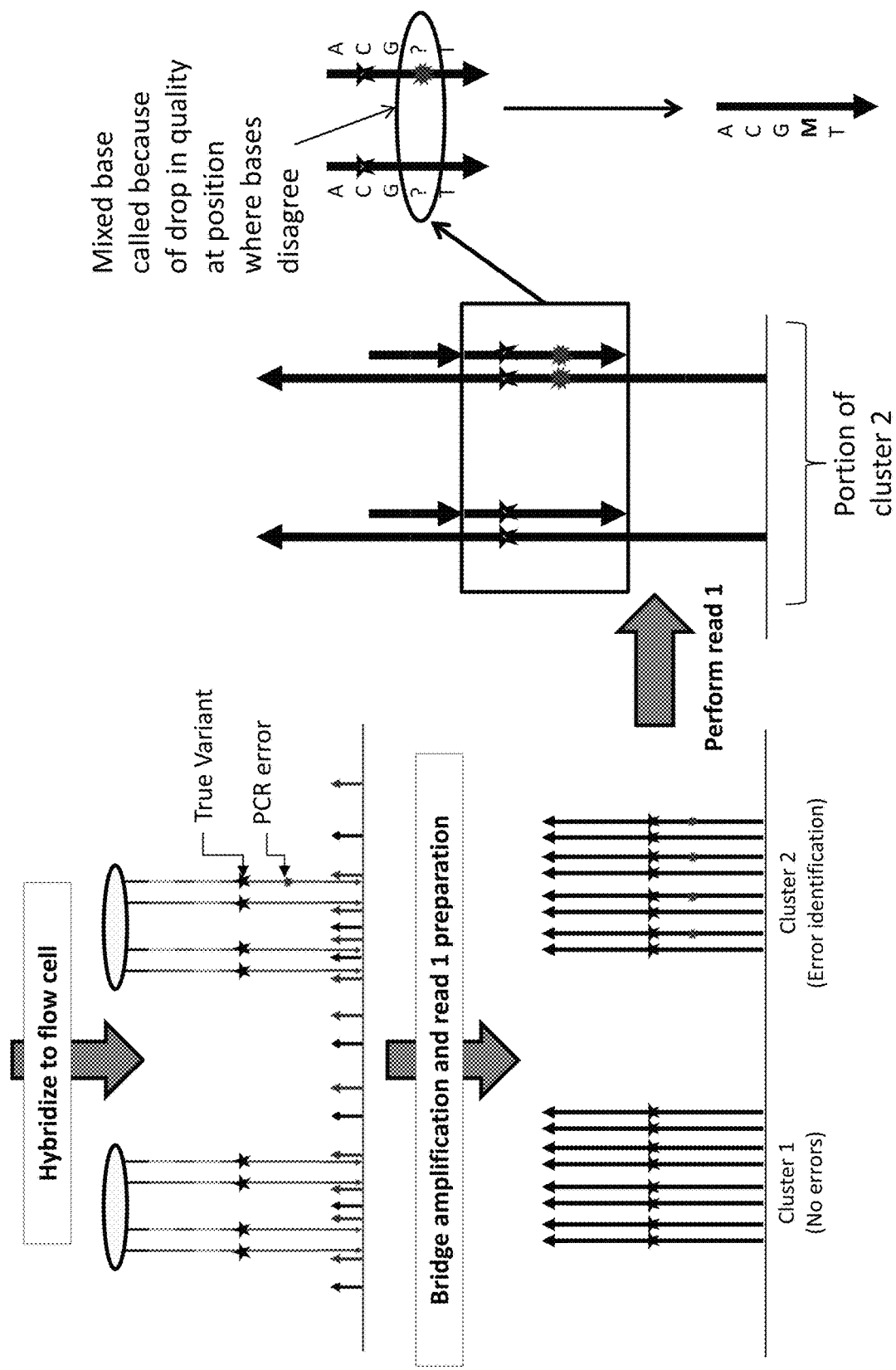
FIG. 18 illustrates a base calling method of the invention based on a single sequencing read and signal quality.
Figure 19:
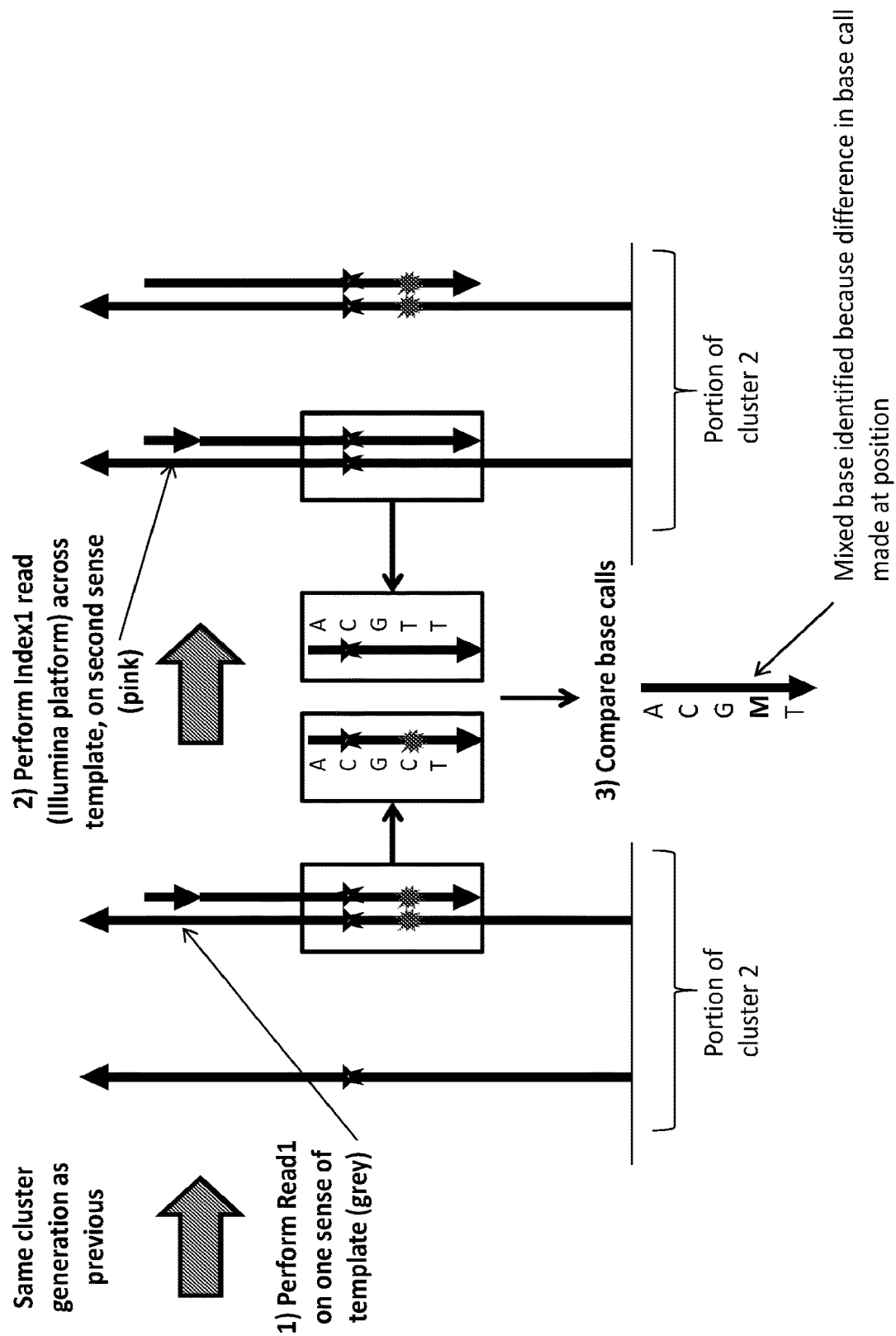
FIG. 19 shows a base calling method based on a comparison of a sense and anti-sense sequencing read.

FIGS. 18 and 19 illustrate alternative sequencing methods using systems and methods of the invention. As shown in FIG. 18, after seeding clusters with multiple template copies and amplifying, errors can be differentiated from true variants through a drop in sequencing quality in a single read at the position where the bases are not the same. Because all amplified strands in the cluster are all read at the same time, in the same direction, a drop in signal quality is the only way to determine a mixed base call within the cluster. In embodiments wherein a cluster is seeded with multiple fragments such as both a sense and antisense strand or templates having different sequencing primer sites, true variants and errors may be identified by comparing results from two different sequencing reads (e.g., reads from each sense or reads using the two different sequencing primers). FIG. 19 illustrates methods of the invention using two separate sequencing reads to compare base calls from a sense and antisense read. Sequencing or other introduced errors should only be seen on one of the reads while true variants should be observed on both reads.

Figure 20:
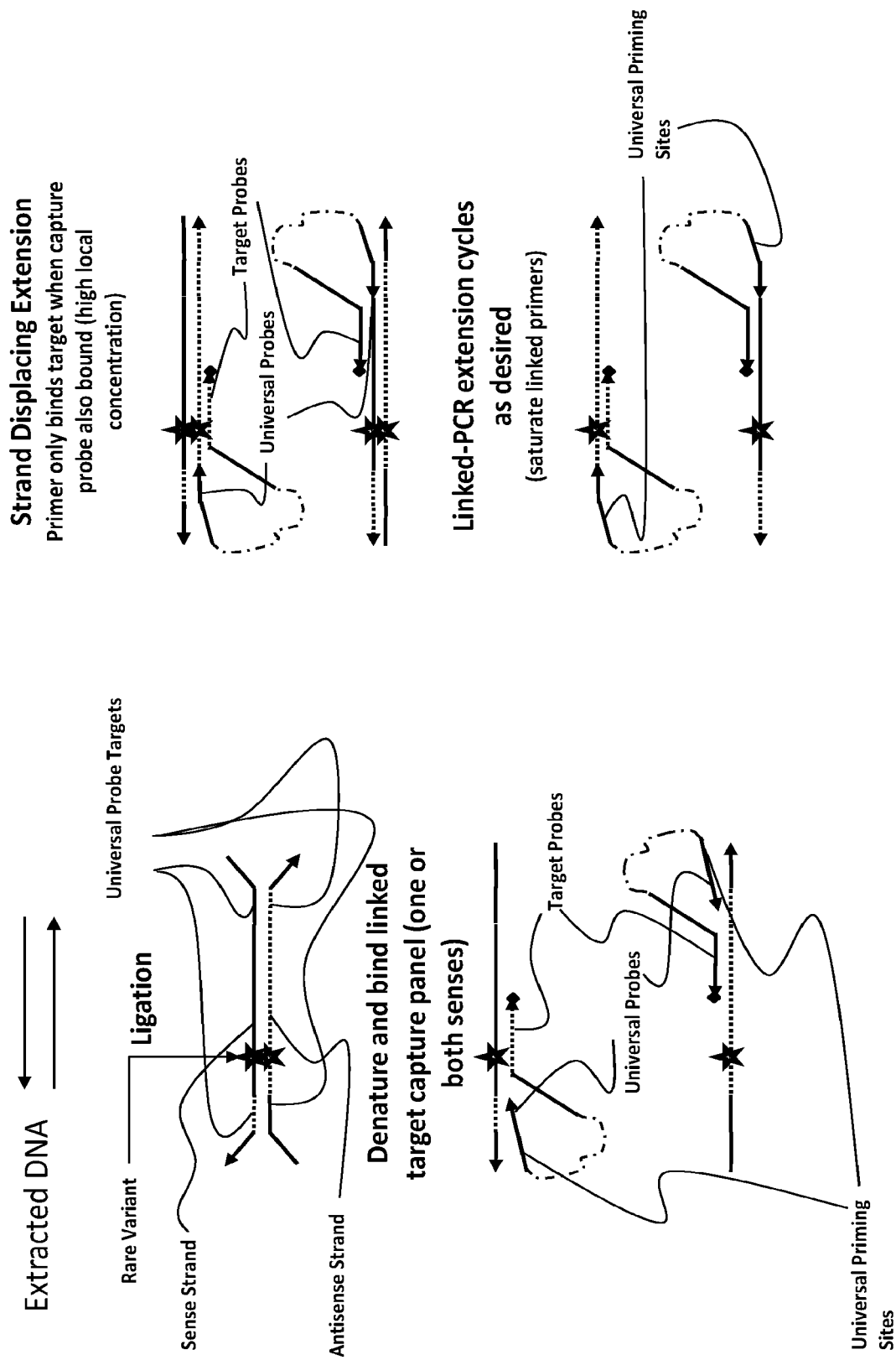
FIG. 20 illustrates exemplary methods of linked target capture of duplex nucleic acids.
Figure 21:
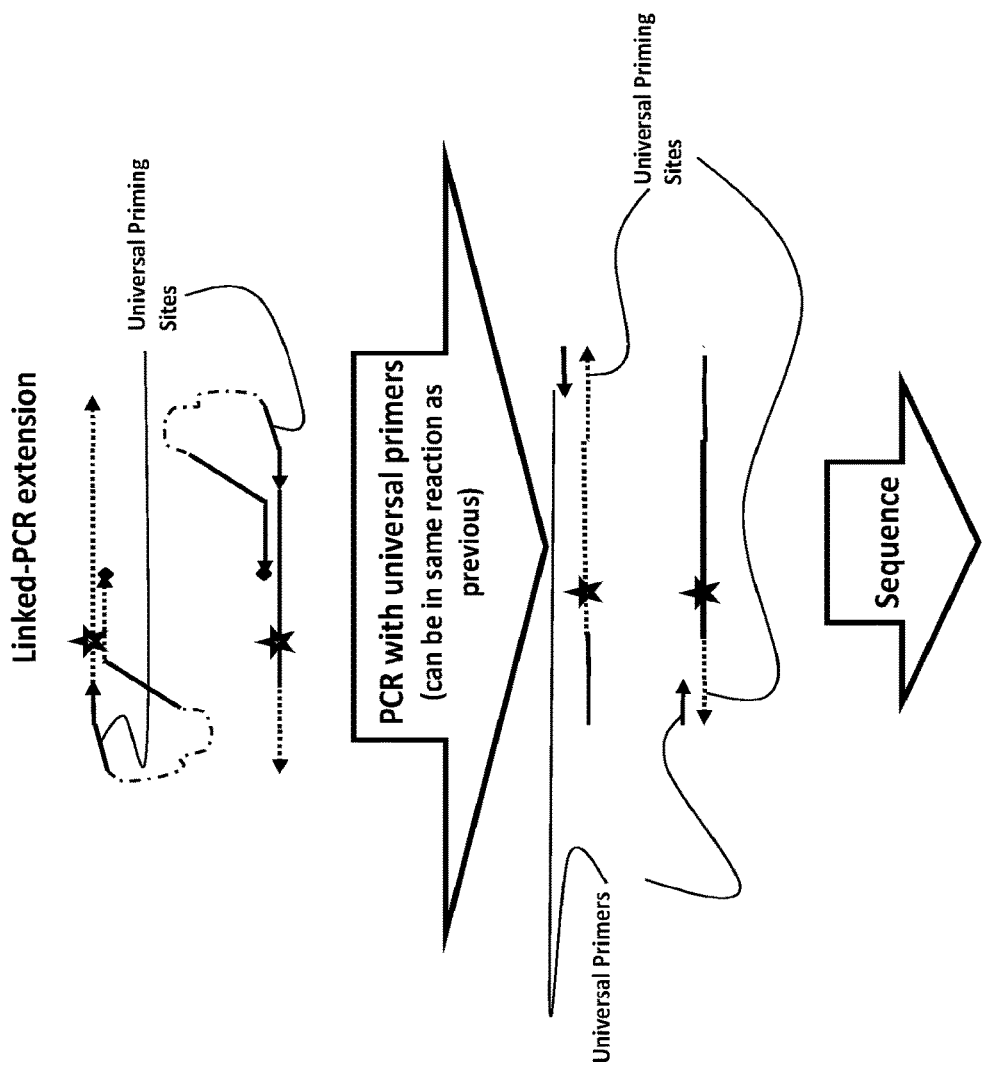
FIG. 21 illustrates amplification methods of linked target captured nucleic acids.

Linked target capture methods may include solution-based capture of genomic regions of interest for targeted DNA sequencing. FIGS. 20 and 21 illustrate exemplary methods of solution-based target capture. Universal probes and optional barcodes (which may be sense specific) are ligated to extracted DNA. The ligated DNA product is then denatured and bound with linked target capture probes comprising a universal priming site and universal probe linked to a target specific probe. Target capture is performed at a temperature where the universal probes cannot bind alone unless local concentration is high due to the binding of the target probe. Strand displacing polymerase (e.g., BST, phi29, or SD) is then used to extend the target-bound linked probes. The target probe is blocked from extension as indicated by the black diamond in FIGS. 20 and 21 so that extension only occurs along the bound universal probe, copying the bound target nucleic acid strand that remains linked to the target probe. A number of linked-PCR extension cycles can then be used to amplify the target sequences. PCR can then be performed using universal primers corresponding to the universal priming sites from the linked target capture probes to amplify one or both strands of the target nucleic acid. This PCR step can be performed in the same reaction without the need for a cleanup step. The amplified target sequence can then be sequenced as described above. No gap is required between the linked capture probes when used in opposite directions although a gap is possible. The capture probes may be produced using universal 5'-linkers by joining the universal linkers to a pre-made capture probe. The capture probes can be joined by streptavidin/biotin or other means as described above and the universal linker may be extended using the capture probe as a template.

Figure 22:
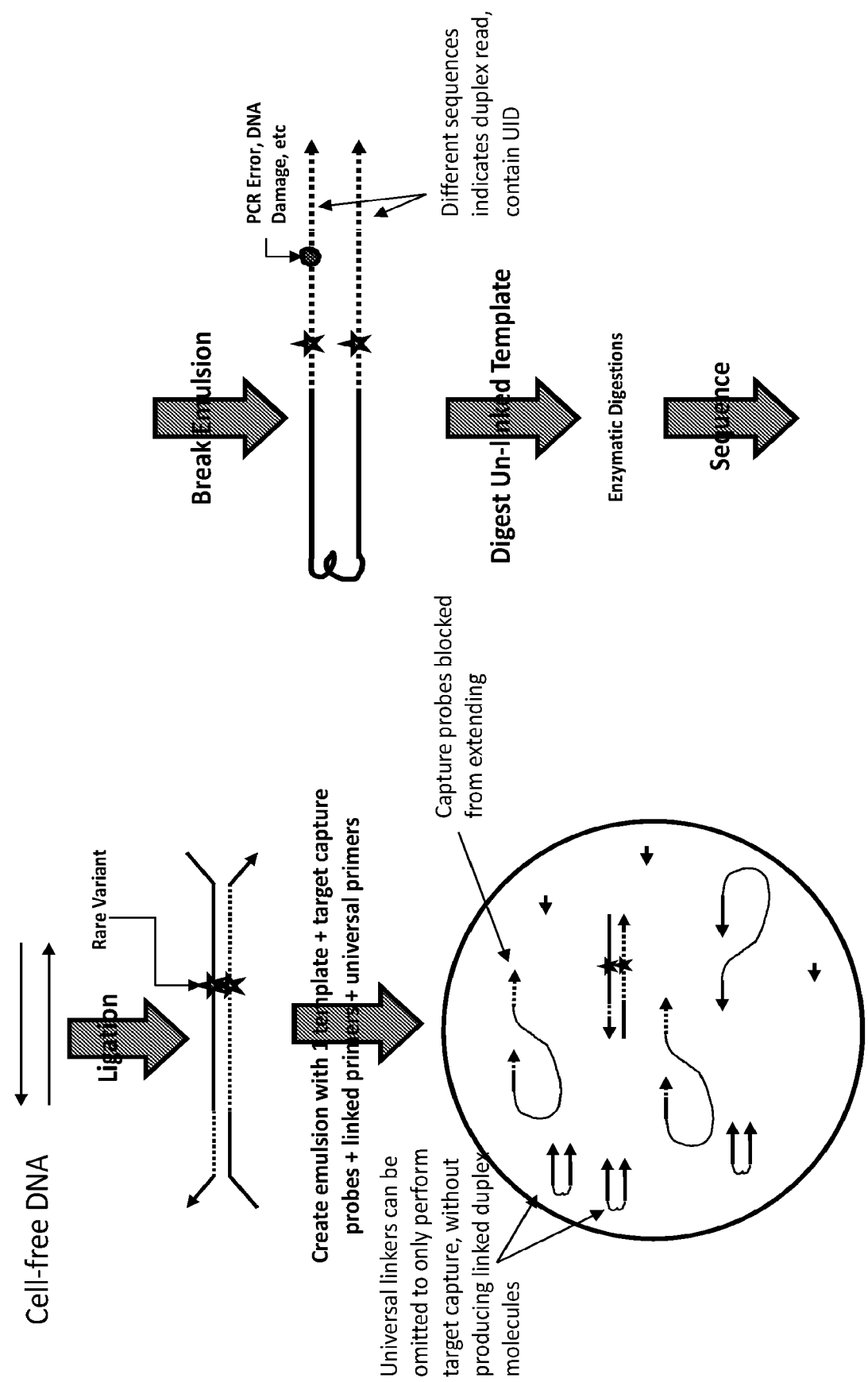
FIG. 22 shows methods of droplet based target capture and linked duplex nucleic acid production.

Methods of the invention include droplet based target capture, optionally using universal linked primers, to capture duplex molecules. The droplet based methods depicted in FIG. 22 are similar to those illustrated in FIG. 1 but use linked target capture probes as described above and depicted in FIGS. 20-21. Universal probes and optional barcodes (which may be sense specific) are ligated to extracted DNA (e.g., cell-free DNA). An emulsion is created as described above using a duplex template molecule and target capture probes comprising a universal priming site and universal probe linked to a target specific probe. As above, target capture is performed at a temperature where the universal probes cannot bind alone unless local concentration is high due to the binding of the target probe and the capture probes are blocked from extending themselves but include a universal priming site such that universal primers and linked universal primers included in the emulsion can be used to amplify the target nucleic acid to produce a linked duplex molecule comprising both sense and antisense strands of the target nucleic acid. Universal linkers may be omitted to perform target capture alone. The emulsion can then be broken and un-linked template can be digested enzymatically leaving only linked duplex molecules can then seed clusters or otherwise be sequenced as described above.

Figure 23A:
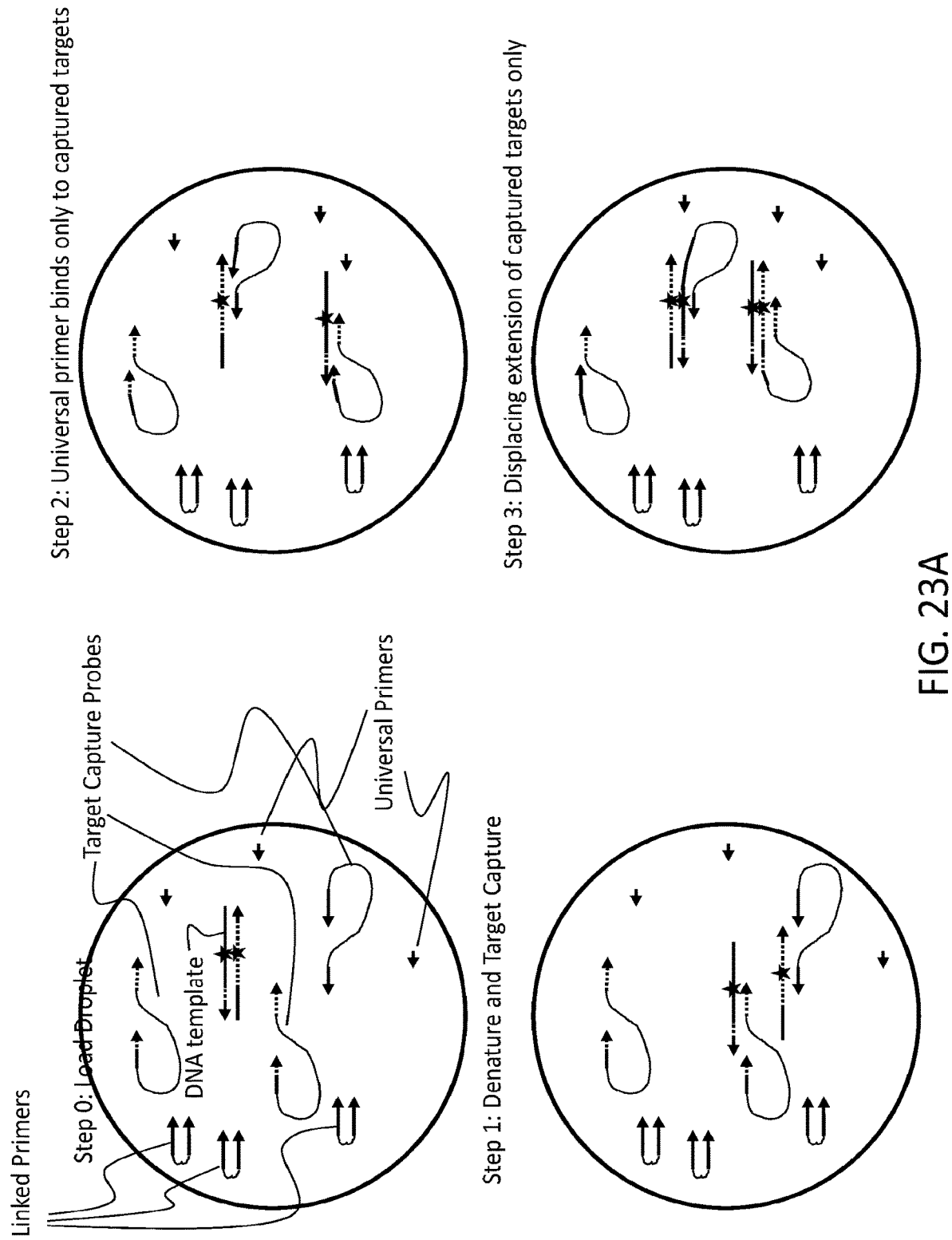
FIGS. 23A and B show steps of a droplet-based target capture method of the invention.
Figure 23B:
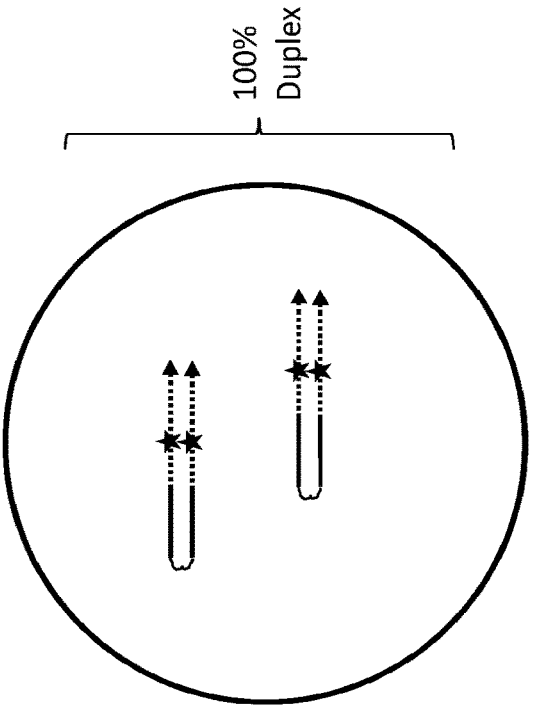
Figure 23B:
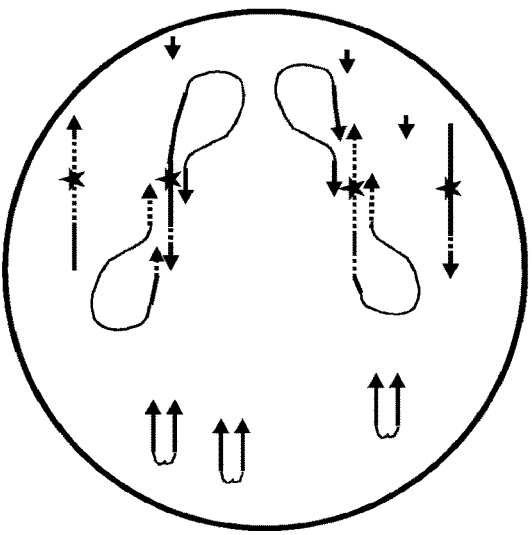
Figure 23B:
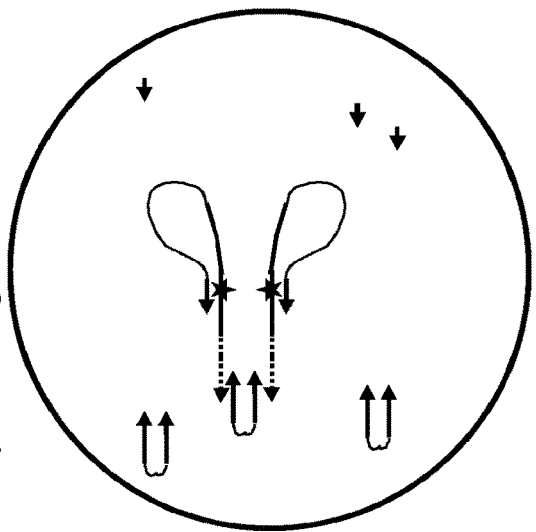

FIGS. 23A and B provide additional details of droplet-based target capture methods of the invention. Step 0 in FIG. 23A shows a duplex template molecule with universal probes and optional barcodes ligated to it is loaded into a droplet with linked and universal primers and target capture probes. The template DNA is denatured in the droplet and the target capture probes then bind the denatured template strands at a temperature where the universal probe will not bind alone unless the target probe is also bound. The universal primer then only binds to captured targets. Extension with strand displacing polymerase then occurs only on the captured targets. Moving to FIG. 23B, extension cycles are then run (e.g., 4-6 cycles) until the liked target capture probes and primers are exhausted. The resulting extension products are then amplified using the universal linked primers to produce linked duplex molecules with strand specific barcodes. As with the solution-based methods, no gap is required between the linked capture probes when in opposite directions. The linked capture probes can be used in one or both directions if omitting the universal linkers to perform target capture alone. Conventional polymerases can be mixed with strand displacing polymerases within the droplet to carry out the various extension and amplification steps of the method.

Figure 24:
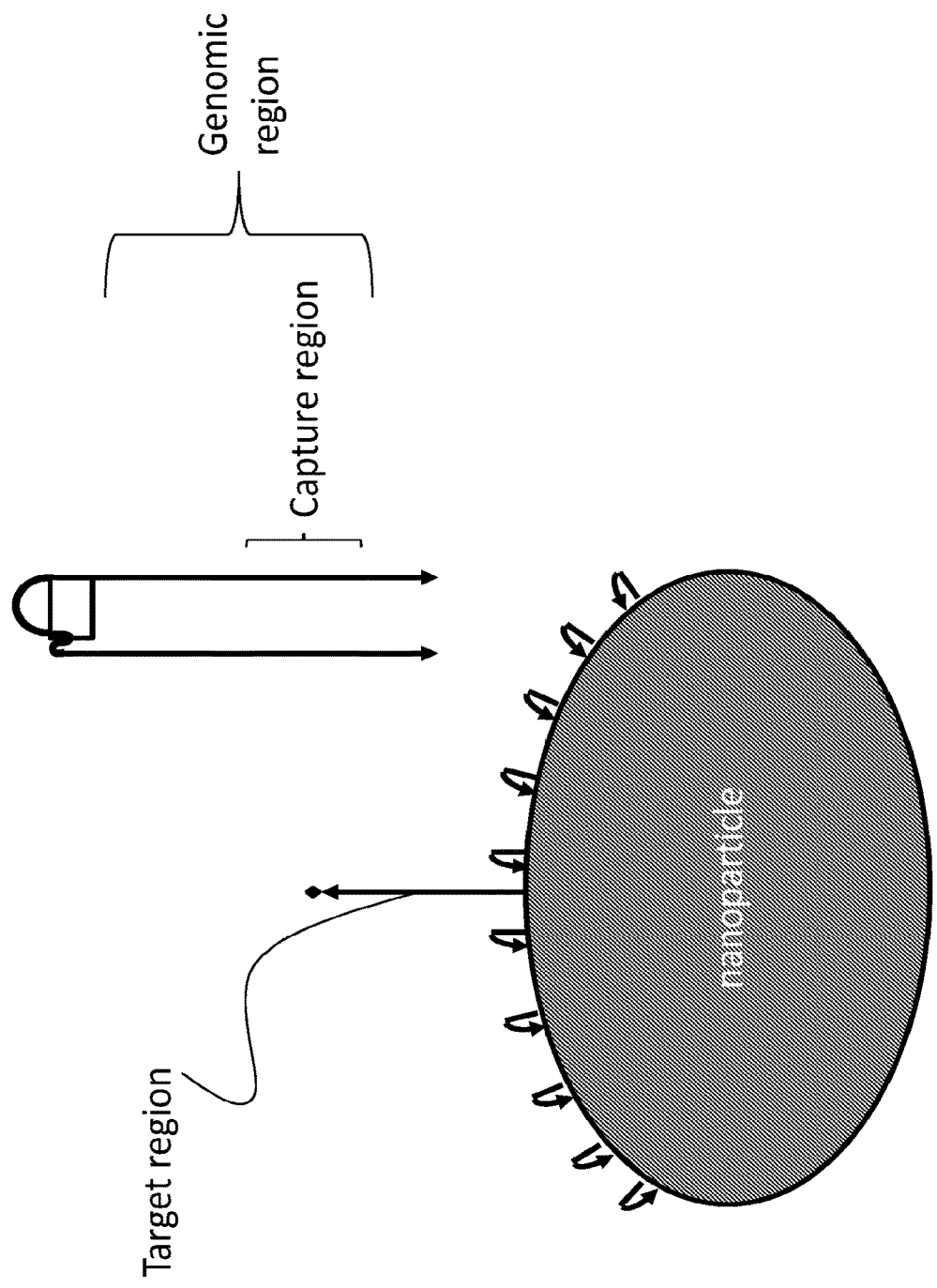
FIG. 24 shows a nanoparticle having universal primers and a strand comprising a target region complementary to a capture region of the linked molecule to be captured.
Figure 25:
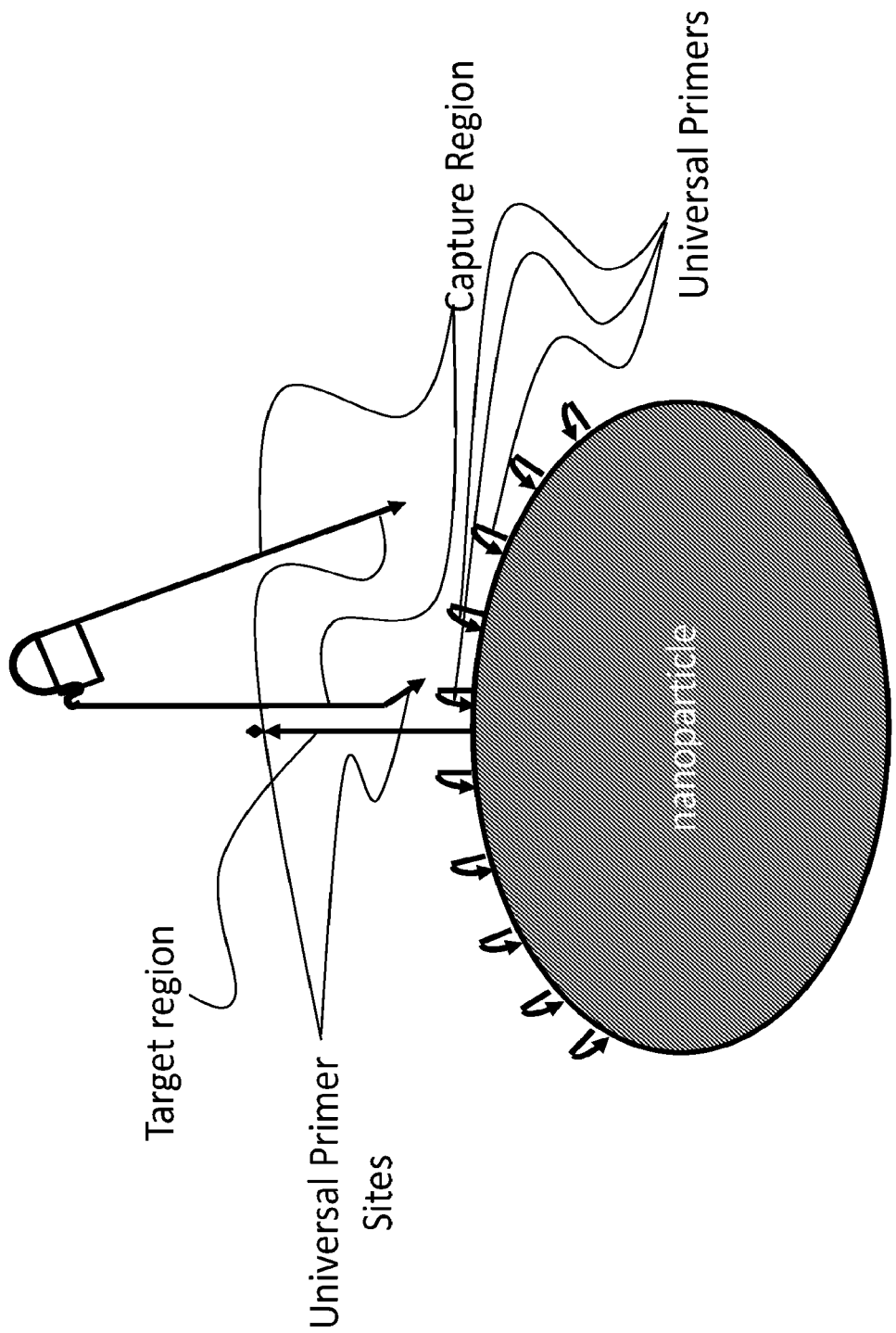
FIG. 25 illustrates binding of the capture region to the target region.
Figure 26:
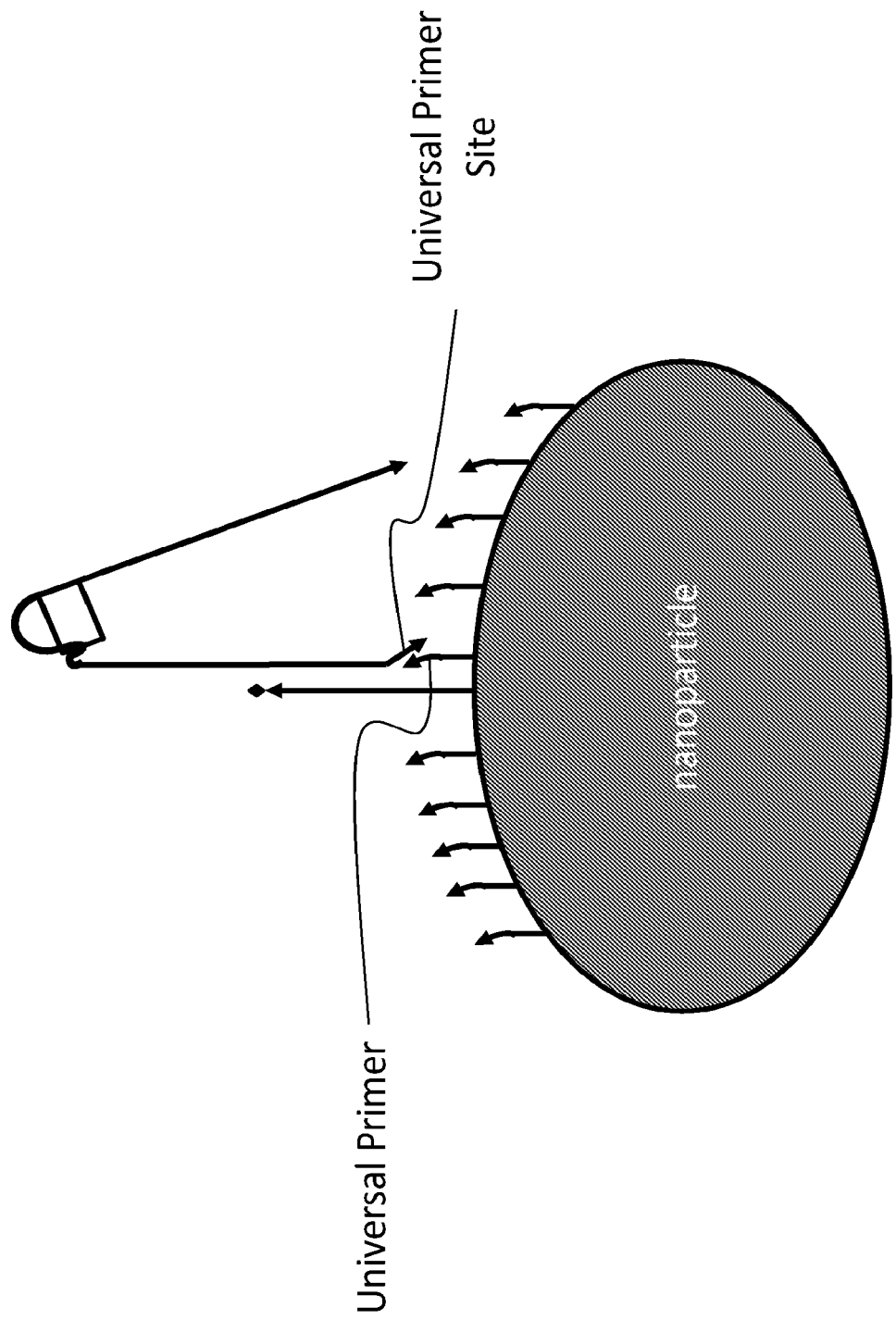
FIG. 26 shows binding of the universal primers to universal primer sites on the linked molecule.
Figure 27:
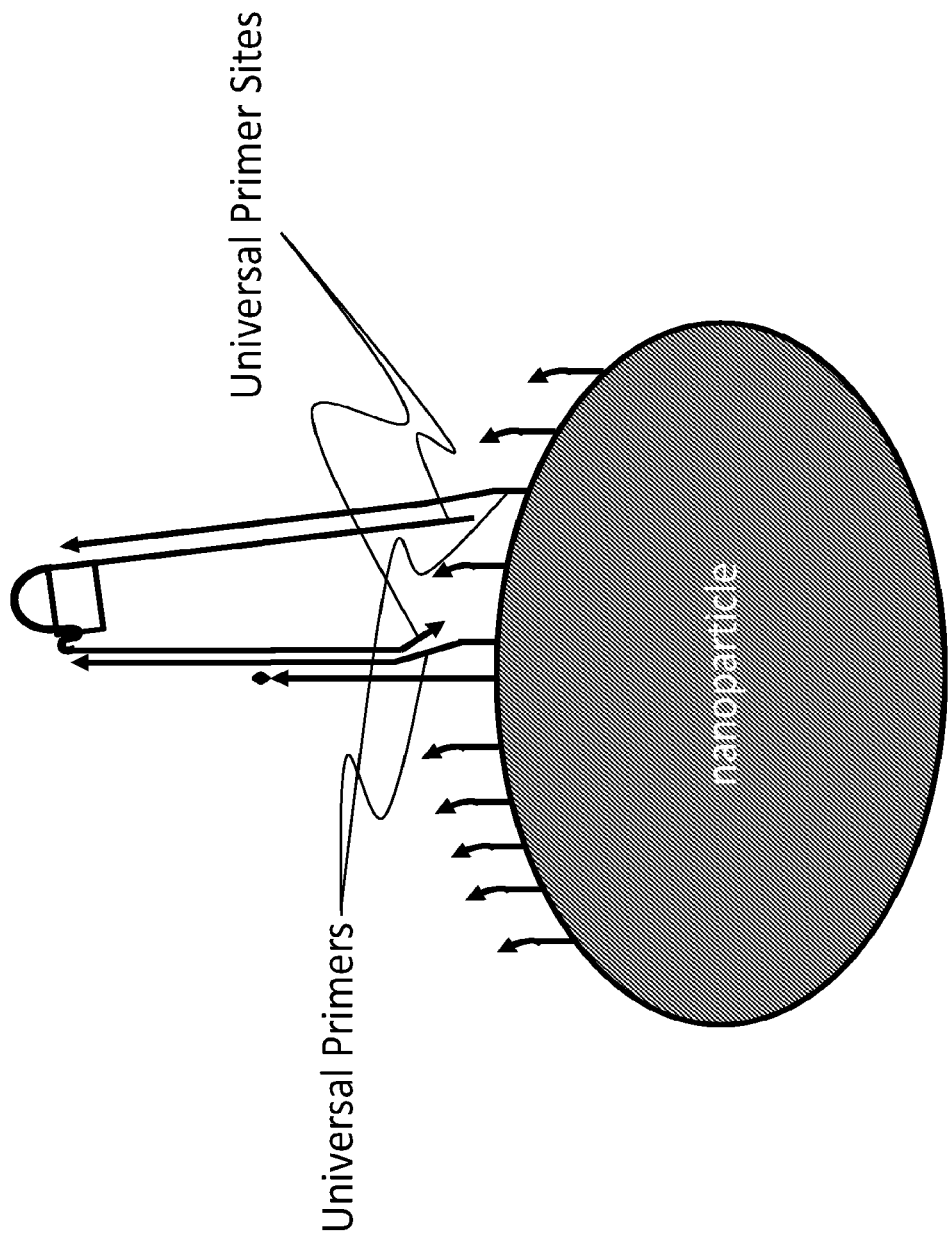
FIG. 27 shows universal primer extension by strand displacing polymerase to produce nanoparticle linked copies of the target molecule comprising both strands of the original linked molecule.
Figure 28:
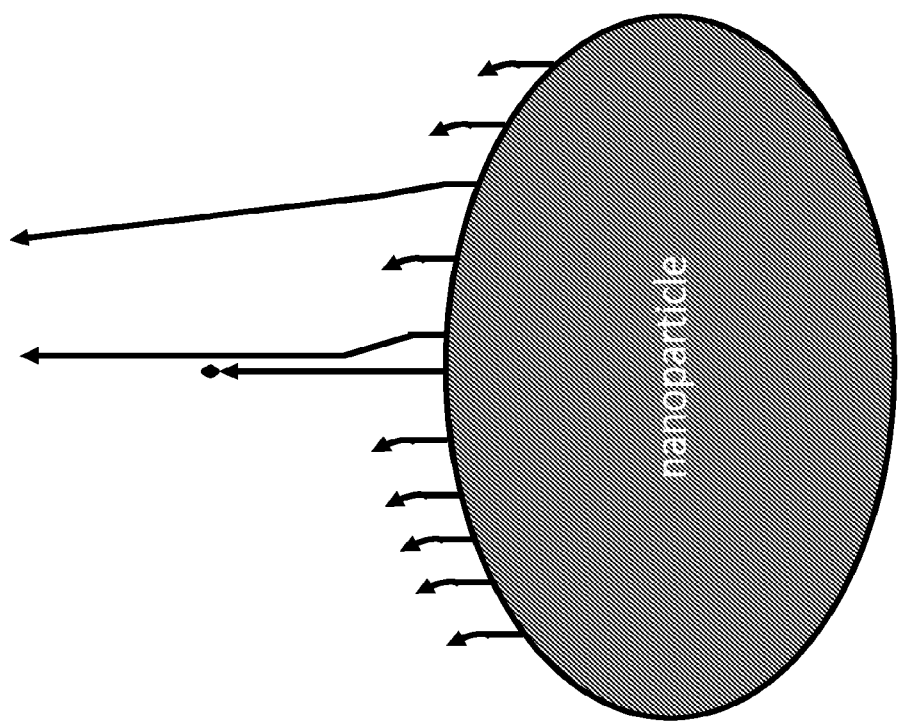
FIG. 28 shows a doubly seeded nanoparticle that may be used to seed a cluster on a flow cell sequencer as described elsewhere in the application.

Certain methods of the invention relate to target capture of linked molecules. Linked copies of molecules such as those created using the methods described above may be targeted and captured and converted to linked molecules for sequencing. FIGS. 24-28 illustrate exemplary methods of nanoparticle target capture of linked molecules. FIG. 24 shows a nanoparticle having universal primers and a strand comprising a target region complementary to a capture region of the linked molecule to be captured. FIG. 25 illustrates binding of the capture region to the target region. This step occurs at a temperature where the target/capture regions will bind but the universal primers will not bind unless the capture region is bound. Unbound templates may be washed away at this step. The temperature of the reaction may then be lowered to promote universal primer binding. FIG. 26 shows binding of the universal primers to universal primer sites on the linked molecule. FIG. 27 shows universal primer extension by strand displacing polymerase to produce nanoparticle linked copies of the target molecule comprising both strands of the original linked molecule. FIG. 28 shows a doubly seeded nanoparticle that may be used to seed a cluster on a flow cell sequencer as described elsewhere in the application.

Figure 16:
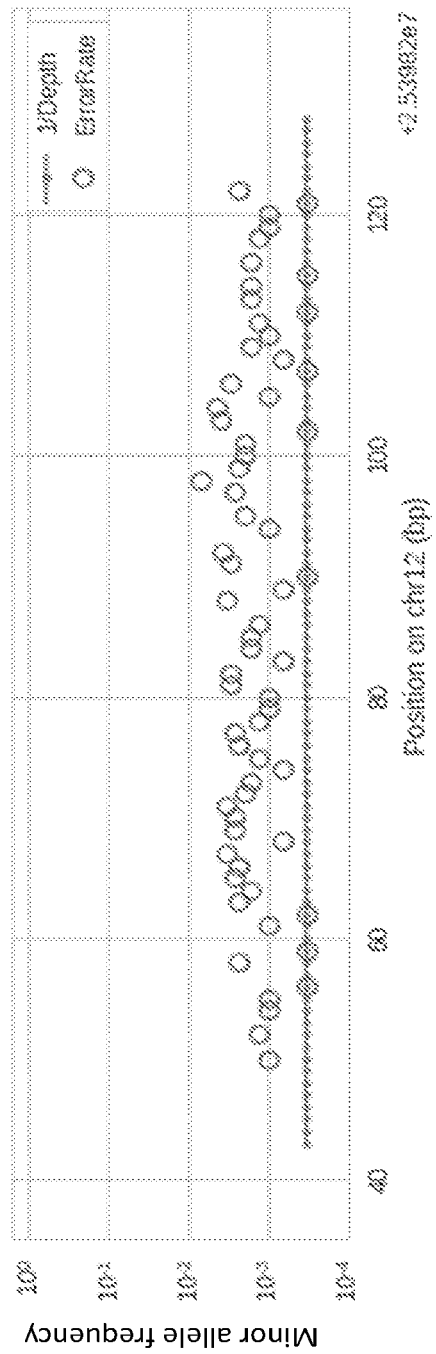
FIG. 16 shows sequencing error rates using singly seeded clusters that aligned to a KRAS amplicon.
Figure 17:
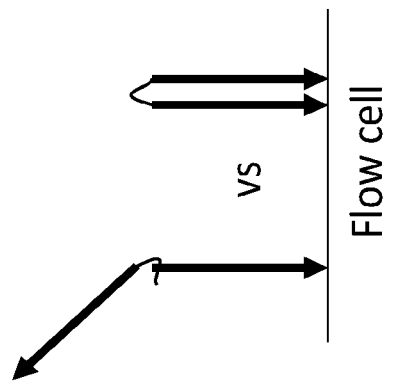
FIG. 17 depicts a singly seeded cluster of the sequencing methods used to produce the results in FIG. 16 and a doubly seeded cluster of the sequencing methods used in FIG. 29.

Example 1: Sequencing Error Reduction in KRAS Amplicon Using Double Seeded Clusters Flow cell clusters were seeded with single template molecules. The single template copies were from a library of linked templates where only one of the linked template molecules was bound to the flow cell as shown in FIG. 17. The first 3000 singly-seeded clusters that aligned to the KRAS amplicon were then analyzed for sequencing errors with an applied quality threshold of greater than 35. The singly-seeded clusters resulted in a mean error of 0.13% with mean depth of about 3000 as shown in FIG. 16. Because the singly-seeded flow cell used a linked template library, the results may represent a lower error rate than would be experienced using a standard single-seeding method with unlinked template molecules.

Figure 29:
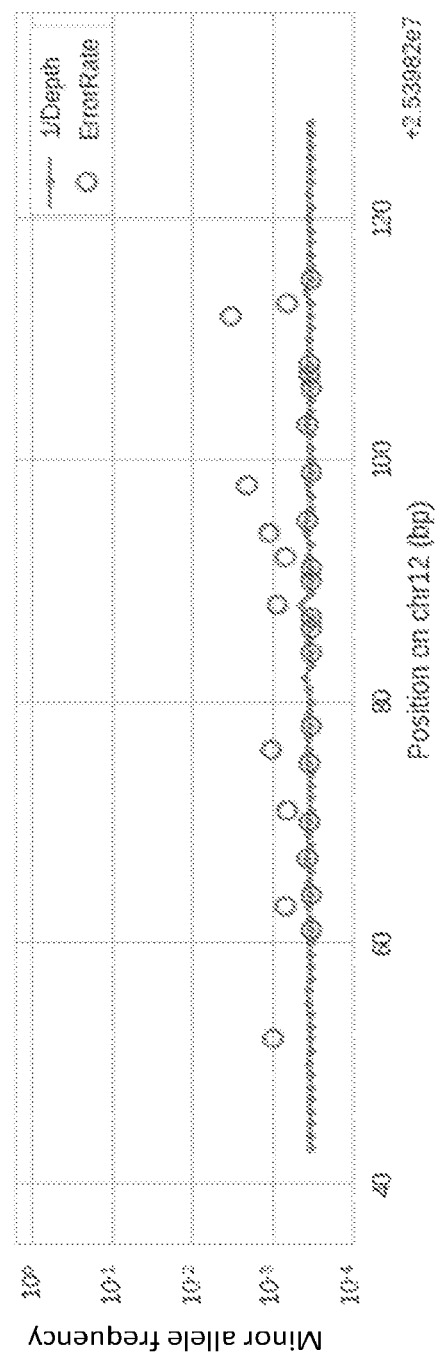
FIG. 29 shows sequencing error rates using doubly seeded clusters that aligned to a KRAS amplicon.

Flow cell clusters were then doubly seeded using linked template molecules where both of the linked molecules were bound to the flow cell to seed the cluster. The first 3000 doubly-seeded clusters that aligned to the chr12 amplicon were then analyzed for sequencing errors with the same applied quality threshold of greater than 35 and a fluorescent chastity filter of 0.8 or greater. The doubly-seeded clusters provided a 7-fold reduction in sequencing errors with less than 3% loss of analyzed bases over the singly-seeded clusters. The mean error rate for the doubly-seeded clusters was 0.02% with a mean depth of about 2920 as shown in FIG. 29.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be

What is claimed:

1. A method for of selectively ligating adapters to a target nucleic acid, the method comprising:
   providing one or more 5' linked ligation adapters each comprising (1) an adapter not complementary to the target nucleic acid and (2) a single-stranded probe complementary to a portion of the target nucleic acid,
   providing one or more 3' linked ligation adapters each comprising (1) an adapter not complementary to the target nucleic acid and (2) a single-stranded probe complementary to a portion of the target nucleic acid,
   combining a sample comprising different nucleic acid sequences with the one or more 5' linked ligation adapters and the one or more 3' linked ligation adapters under conditions in which the one or more 5' linked ligation adapters and the one or more 3' linked ligation adapters hybridize specifically to at least a first fragment in the heterogeneous mixture, wherein the first fragment comprises the target nucleic acid,
   ligating one of the 5' linked ligation adapters to the 5' terminus of the first fragment and
   ligating one of the 3' linked ligation adapters to the 3' terminus of the first fragment, thereby producing a ligation product comprising the target nucleic acid.

2. The method of claim 1, wherein the adapter of each of the linked ligation adapter comprises a universal priming site, a unique molecular identifier, a barcode, or any combination thereof.

3. The method of claim 1, wherein the target nucleic acid has a length from about 100 to about 500 nucleotides.

4. The method of claim 1, comprising combining said sample, said one or more linked ligation adapters, and a ligase under conditions in which said one or more linked ligation adapters specifically hybridize to the first fragment and said terminus of the linked ligation adapter and the terminus of the first fragment ligate together, thereby producing the ligation product.

5. The method of claim 1, wherein said one or more linked ligation adapters comprise multiple linked ligation adapters comprising different single-stranded probes complementary to different target nucleic acid portions.

6. The method of claim 1, wherein said one or more linked ligation adapters comprise a first linked ligation adapter comprising a first single-stranded probe complementary to a first portion of the target nucleic acid of interest and a second linked ligation adapter comprising a single-stranded probe complementary to a second portion of the target nucleic acid.

7. The method of claim 1, wherein at least one of the one or more linked ligation adapters comprises a modified DNA base.

8. The method of claim 1, wherein at least one of the one or more linked ligation adapters is blocked to prevent extension.

9. The method of claim 1, wherein at least one of the one or more linked ligation adapters comprises a cleavage site.

10. The method of claim 1, further comprising amplifying the target nucleic acid.

11. A method of enrichment of a target DNA fragment, the method comprising:
   (a) producing a mixture of ligation products by combining a mixture of nucleic acid fragments with one or more 5' linked ligation adapters and one or more 3' linked ligation adapters of the method of claim 1; and
   (b) removing fragments from the mixture that are not ligated to any one of the 5' and 3' linked ligation adapters.

* * * * *